(12) United States Patent
Okun et al.

(10) Patent No.: US 9,334,320 B2
(45) Date of Patent: *May 10, 2016

(54) METHODS OF TREATING MODERATE TO SEVERE HIDRADENITIS SUPPURATIVA WITH ANTI-TNFALPHA ANTIBODY

(71) Applicant: AbbVie Biotechnology, Ltd., Hamilton (BM)

(72) Inventors: Martin M. Okun, Wilmette, IL (US); Thomas C. Harris, Gurnee, IL (US)

(73) Assignee: AbbVie Biotechnology Ltd., Hamilton (BM)

( * ) Notice: Subject to any disclaimer, the term of this patent is extended or adjusted under 35 U.S.C. 154(b) by 42 days.

This patent is subject to a terminal disclaimer.

(21) Appl. No.: 14/289,115

(22) Filed: May 28, 2014

(65) Prior Publication Data

US 2015/0147335 A1 May 28, 2015

Related U.S. Application Data

(63) Continuation of application No. 13/153,131, filed on Jun. 3, 2011, now Pat. No. 8,747,854.

(60) Provisional application No. 61/474,764, filed on Apr. 13, 2011, provisional application No. 61/430,645, filed on Jan. 7, 2011, provisional application No. 61/351,125, filed on Jun. 3, 2010.

(51) Int. Cl.
*A61K 39/395* (2006.01)
*C07K 16/24* (2006.01)
*A61K 39/00* (2006.01)

(52) U.S. Cl.
CPC ............ *C07K 16/241* (2013.01); *A61K 39/3955* (2013.01); *C07K 16/244* (2013.01); *A61K 2039/505* (2013.01); *A61K 2039/545* (2013.01); *C07K 2317/51* (2013.01); *C07K 2317/515* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,090,382 A | 7/2000 | Salfeld et al. | |
| 6,177,077 B1 | 1/2001 | Tobinick | |
| 6,258,562 B1 | 7/2001 | Salfeld et al. | |
| 6,509,015 B1 | 1/2003 | Salfeld et al. | |
| 6,537,549 B2 | 3/2003 | Tobinick | |
| 7,223,394 B2 | 5/2007 | Salfeld et al. | |
| 7,541,031 B2 | 6/2009 | Salfeld et al. | |
| 7,588,761 B2 | 9/2009 | Salfeld et al. | |
| 7,863,426 B2 | 1/2011 | Wan et al. | |
| 7,919,264 B2 | 4/2011 | Maksymowych et al. | |
| 8,034,906 B2 | 10/2011 | Borhani et al. | |
| 8,092,998 B2 | 1/2012 | Stuhlmuller et al. | |
| 8,093,045 B2 | 1/2012 | Pla et al. | |
| 8,187,836 B2 | 5/2012 | Hsieh | |
| 8,197,813 B2 | 6/2012 | Salfeld et al. | |
| 8,206,714 B2 | 6/2012 | Salfeld et al. | |
| 8,216,583 B2 | 7/2012 | Kruase et al. | |
| 8,231,876 B2 | 7/2012 | Wan et al. | |
| 8,372,400 B2 | 2/2013 | Salfeld et al. | |
| 8,372,401 B2 | 2/2013 | Salfeld et al. | |
| 8,414,894 B2 | 4/2013 | Salfeld et al. | |
| 8,420,081 B2 | 4/2013 | Fraunhofer et al. | |
| 8,436,149 B2 | 5/2013 | Borhani et al. | |
| 8,636,704 B2 | 1/2014 | Shang et al. | |
| 8,663,945 B2 | 3/2014 | Pla et al. | |
| 8,679,061 B2 | 3/2014 | Julian et al. | |
| 8,715,664 B2 | 5/2014 | Hoffman et al. | |
| 8,747,854 B2 * | 6/2014 | Okun | C07K 16/244 424/130.1 |
| 8,753,633 B2 | 6/2014 | Salfeld et al. | |
| 8,753,839 B2 | 6/2014 | Fraunhofer et al. | |
| 8,846,046 B2 | 9/2014 | Kaymakcalan et al. | |
| 8,889,135 B2 | 11/2014 | Fischkoff et al. | |
| 8,889,136 B2 | 11/2014 | Hoffman et al. | |
| 2003/0012786 A1 | 1/2003 | Teoh et al. | |
| 2003/0161828 A1 | 8/2003 | Abdelghany et al. | |
| 2003/0206898 A1 | 11/2003 | Fischkoff et al. | |
| 2003/0219438 A1 | 11/2003 | Salfeld et al. | |
| 2004/0009172 A1 | 1/2004 | Fischkoff et al. | |
| 2004/0033228 A1 | 2/2004 | Krause et al. | |
| 2004/0126372 A1 | 7/2004 | Banerjee et al. | |
| 2004/0126373 A1 | 7/2004 | Banerjee et al. | |
| 2004/0131614 A1 | 7/2004 | Banerjee et al. | |
| 2004/0136989 A1 | 7/2004 | Banerjee et al. | |

(Continued)

FOREIGN PATENT DOCUMENTS

WO WO-92/16553 10/1992
WO WO-97/29131 8/1997

(Continued)

OTHER PUBLICATIONS

Dr. Martin Okun Declaration Under 37 CFR 1.132, filed Feb. 20, 2014 in Okun et al. U.S. Appl. No. 13/153,131.*
Resubmission of Amendment and Response to Final Office Action Request for Track 1 Prioritized Examination filed Feb. 27, 2014 in Okun et al. U.S. Appl. No. 13/153,131.*
Blanco et al., "Long-term successful adalimumab therapy in severe hidradenitis suppurativa," Arch Dermatol, 145(5):580-584 (2009).
Haslund et al., "Treatment of hidradenitis suppurativa with tumour necrosis factor-alpha inhibitors," Acta Derm Venereal, 89(6):595-600 (2009).
Adams et al., "Treatment of Hidradenitis Suppurativa With Etanercept Injection," Arch Dermatol, 146:501-505, (2010).

(Continued)

*Primary Examiner* — Phillip Gambel
(74) *Attorney, Agent, or Firm* — Foley Hoag LLP

(57) ABSTRACT

The invention provides methods, uses and compositions for the treatment of hidradenitis suppurativa. The invention describes methods and uses for treating hidradenitis suppurativa, wherein a TNFα inhibitor, such as a human TNFα antibody, or antigen-binding portion thereof, is used to treat hidradenitis suppurativa in a subject. Also described are methods for determining the efficacy of a TNFα inhibitor for treating hidradenitis suppurativa in a subject.

34 Claims, 3 Drawing Sheets

(56) References Cited

U.S. PATENT DOCUMENTS

| | | |
|---|---|---|
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0219142 A1 | 11/2004 | Banerjee et al. |
| 2006/0083741 A1 | 4/2006 | Hoffman et al. |
| 2007/0041905 A1 | 2/2007 | Hoffman et al. |
| 2007/0081996 A1 | 4/2007 | Hoffman et al. |
| 2007/0202104 A1 | 8/2007 | Banerjee et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0311043 A1 | 12/2008 | Hoffman et al. |
| 2009/0028794 A1 | 1/2009 | Medich et al. |
| 2009/0068172 A1 | 3/2009 | Kaymakcalan et al. |
| 2009/0110679 A1 | 4/2009 | Li et al. |
| 2009/0123378 A1 | 5/2009 | Wong et al. |
| 2009/0226530 A1 | 9/2009 | Lassner et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0021451 A1 | 1/2010 | Wong |
| 2010/0040630 A1 | 2/2010 | Elden et al. |
| 2010/0278822 A1 | 11/2010 | Fraunhofer et al. |
| 2011/0171227 A1 | 7/2011 | Okun et al. |
| 2012/0014956 A1 | 1/2012 | Kupper et al. |
| 2012/0039900 A1 | 2/2012 | Stuhlmuller et al. |
| 2012/0107783 A1 | 5/2012 | Julian et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0282262 A1 | 11/2012 | Okun et al. |
| 2012/0282270 A1 | 11/2012 | Krause et al. |
| 2013/0004507 A1 | 1/2013 | Fischkoff et al. |
| 2013/0122011 A1 | 5/2013 | Hoffman et al. |

FOREIGN PATENT DOCUMENTS

| | | |
|---|---|---|
| WO | WO-02/100330 | 12/2002 |
| WO | WO-2004/009776 A2 | 1/2004 |
| WO | WO-2005/110452 A2 | 11/2005 |

OTHER PUBLICATIONS

Amano et al., "A prospective open-label clinical trial of adalimumab for the treatment of hidradenitis suppurativa," Int J Dermatol, 49(8):950-955 (2010).
Baeten et al., "Immunomodulatory effects of anti-tumor necrosis factor alpha therapy on synovium in spondylarthropathy: histologic findings in eight patients from an open-label pilot study," Arthritis & Rheumatism, 44(1):186-195 (2001).
Baugh et al., "Mechanisms for modulating TNFa in immune and inflammatory disease," Current Opinion in Drug Discovery & Development, 4(5):635-650 (2001).
Bodmer et al., "Preclinical review of anti-tumor necrosis factor monoclonal antibodies," Critical Care Medicine, 21(10):S441-S446 (1993).
Bouma et al., "The immunological and genetic basis of inflammatory bowel disease," Nature Review Immunology 3:521-533 (2003).
Casset et al., "A peptide mimetic of an anti-CD4 monoclonal antibody by rational design," Biochemical and Biophysical Research Communications, 307:198-205 (2003).
Cavagna et al., "Infliximab in the treatment of adult Still's disease refractory to conventional therapy," Clin Exp Rheumatol, 19(3):329-332 (2001).
Chen et al., "Enhancement and destruction of antibody function by somatic mutation: unequal occurrence is controlled by V gene combinatorial associations," EMBO J., 14(12):2784-94 (1995).
Chikanza, "Juvenile rheumatoid arthritis: therapeutic perspectives," Pediatric Drugs 4(5):335-348 (2002).
Colman, "Effects of amino acid sequence changes on antibody-antigen interactions," Research in Immunology, 145(1):33-36 (1994).
Genovese et al., "Safety and efficacy of adalimumab in treatment of patients with psoriatic arthritis who had failed DMARD therapy," J Rheumatol, 34:1040-1050 (2007), abstract.
Gordon et al., "Clinical Response to Adalimumab Treatment in Patients with Moderate to Severe psoriasis: Double-Blind, Randomized Controlled Trial and Open-Label Extension Study," J. Am. Acad. Derm., 55(1):598-606 (2006).
Gorovoy et al., "Succesful Treatment of Recalcitrant Hidradenitis Suppurativa with Adalimumab," Case Rep. Dermatol., 1:71-77 (2009).
Grom et al., "Patterns of Expression of Tumor Necrosis Factor $\alpha$, Tumor Necrosis Factor $\beta$, and Their Receptors in Synovia of Patients with Juvenile Rheumatoid Arthritis and Juvenile Spondylarthropathy," Arthritis & Rheumatism, 39(10):1703-1710 (1996).
Harde et al., "Treatment of severe recalcitrant Hidradenitis Suppurativa with adalimumab," J. Deutsch. Dermatol. Gesell. 7:139-141 (2009).
Highlights of HUMIRA Prescribing Information, Abbott Laboratories, North Chicago, IL, USA, pp. 1-70, updated Mar. 2011.
http://www.marketwatch.com/story/biogen-slumps-cdp-571-studyresults-miss-endpoint (Jul. 30, 2002).
HUMIRA, Highlights of Prescribing Information, Abbott Laboratories, North Chicago, IL, USA, pp. 1-56, Nov. 2009.
HUMIRA Prescribing Information, Abbott Laboratories, North Chicago, IL, USA, pp. 1-13, Jan. 2003.
International Preliminary Examination Report for PCT/US2003/022566.
Jemec, "Hidradenitis Suppurativa," J. of Cutaneous Medicine and Surgery, 7:47-56 (2003).
Katsanos et al., "Axillary Hidradenitis Suppurativa Successfully Treated With Infliximab in a Crohn's Disease Patient," AJG 97:2155-2156 (2002).
Kempeni, "Preliminary Results of early clinical trials with the fully human anti-TNF$\alpha$ monoclonal antibody D2E7," Ann. Rheum. Dis., 58(1):170-172 (1999).
Keystone et al., "The Fully Human Anti-TNF Monoclonal Antibody, Adalimumab (D2E7), Dose Ranging Study: The 24-Week Clinical Results in Patients with Active RA on Methotrexate Therapy (The ARMADA Trial)," (EULAR), Prague, Czech Republic, (2001).
Kimball et al., "Adalimumab for the Treatment of Moderate to Severe Hidradenitis Suppurativa," Annals of Internal Medicine, 157:846-855 (2012).
Kraetsch et al., "Successful treatment of a small cohort of patients with adult onset of Still's disease with infliximab: first experiences," Annals of the Rheumatic Diseases, 60(3):iii55-iii57 (2001).
Kroesen et al., "Serious bacterial infections in patients with rheumatoid arthritis under anti-TNF alpha therapy," Rheumatology 42:617-621 (2003).
Kussie et al., "A Single Engineered Amino Acid Substitution Changes Antibody Fine Specificity," J. Immunol., 152(1):146-52 (1994).
Lapins et al., "Coagulase-negative staphylococci are the most common bacteria found in cultures from the deep portions of hidradenitis suppurativa lesions, as obtained by carbon dioxide laser surgery," Br. J. Dermatol., 140:90-95 (1999).
Lebwohl et al., "Infliximab for the treatment of hidradenitis suppurativa," J. Derm. Acad. Med., 49:S275-S276 (2003).
Lee et al., "A prospective clinical trial of open label etanercept for the treatment of hidradenitis suppurativa," J. Am. Acad. Dermatol., 60(4): 565-573 (2009).
Lorenz et al., "Perspectives for TNF-alpha-targeting therapies," Arthritis Research, 4(3):S17-24 (2002).
Martinez et al., "Hidradenitis Suppurativa and Crohn's disease: Response to Treatment with Infliximab," Inflammatory Bowel Diseases, 7(4):323-326 (2001).
Mease, "Adalimumab: an anti-TNF agent for the treatment of psoriatic arthritis," Expert Opin. Biol. Ther., 5(11):1491-1504 (2005).

(56) References Cited

OTHER PUBLICATIONS

Neuner et al., "Cytokine release by peripheral blood mononuclear cells is affected by 8-methoxypsoralen plus UV-A," Photochem Photobiol., 59(2):182-188 (1994).
Ogilvie et al., "Treatment of psoriatic arthritis with antitumor necrosis factor-α antibody clears skin lesions of psoriasis resistant to treatment with methotrexate," British Journal of Dermatology, 144(3):587-589, (2001).
Oh et al., "Treatment with anti-tumor necrosis factor alpha (TNF-alpha) monoclonal antibody dramatically decreases the clinical activity of psoriasis lesions," Journal of the American Academy of Dermatology, 42(5 Pt 1):829-30 (2000).
Parks et al., "Pathogenesis, clinical features and management of hidradenitis suppurativa," Ann R Coll Surg Engl., 79:83-89 (1997).
Paul, "Immunogenicity and Antigen Structure," Fundamental Immunology, 3(242): 292-295 (1993).
Remicade (infliximab) Product Label (Jun. 2002).
Roussomoustakaki et al., "Hidradenitis suppurativa associated with Crohn's disease and spondyloarthropathy: response to anti-TNF therapy," J. Gastroenterol, 38:1000-1004 (2003).
Rudikoff et al., "Single amino acid substitution altering antigen-binding specificity," Proc. Natl. Acad. Sci. USA, 79(6):1979-1983 (1982).
Ruperto, "48-Week Data From the Study of Adalimumab in Children With Juvenile Rheumatoid Arthritis (JRA)," Ann. Rheum. Dis., 65(2):56 (2006).
Sandborn et al., "CDP571, a humanised monoclonal antibody to tumour necrosis factor α, for moderate to severe Crohn's disease: a randomized, double blind, placebo controlled trial," Gut, 53:1485-1493 (2004).
Sandborn et al., "Etanercept for Active Crohn's Disease: A Randomized, Double-blind, Placebo-Controlled Trial," Gastroenterol, 121:1088-1094 (2001).
Slade et al., "Hidradenitis suppurativa: pathogenesis and management," Br. Assoc. Plast. Surg., 56:451-461 (2003).
Sullivan et al., "Infliximab for hidradenitis suppurativa," Br. J. Dermatol., 149:1046-1049 (2003).
Sun et al., "Individually Distinct Ig Homology Domains in PECAM-1 Regulate Homophilic Binding and Modulate Receptor Affinity," J. Biol. Chem., 271:11090-11098 (1996).
Takematsu, "Absence of tumor necrosis factor-alpha in suction blister fluids and stratum corneum from patients with psoriasis," Arch Dermatol Res., 281(6):398-400 (1989).
Ueda et al., "Two Mouse Monoclonal Antibodies Detecting Two Different Epitopes of an Activated Lymphocyte Antigen on Adult T-Cell Leukemia Cells," Cancer Res. 45:1314-1319 (1985).
Victor et al., "TNF-alpha and apoptosis: implications for the pathogenesis and treatment of psoriasis," J Drugs Dermatol, 1(3):264-75 (2002).
Yamauchi et al., "Adalimumab in the Management of Hidradenitis Suppurativa," J Am Acad. Derm., AB41:P504 (2007).

* cited by examiner

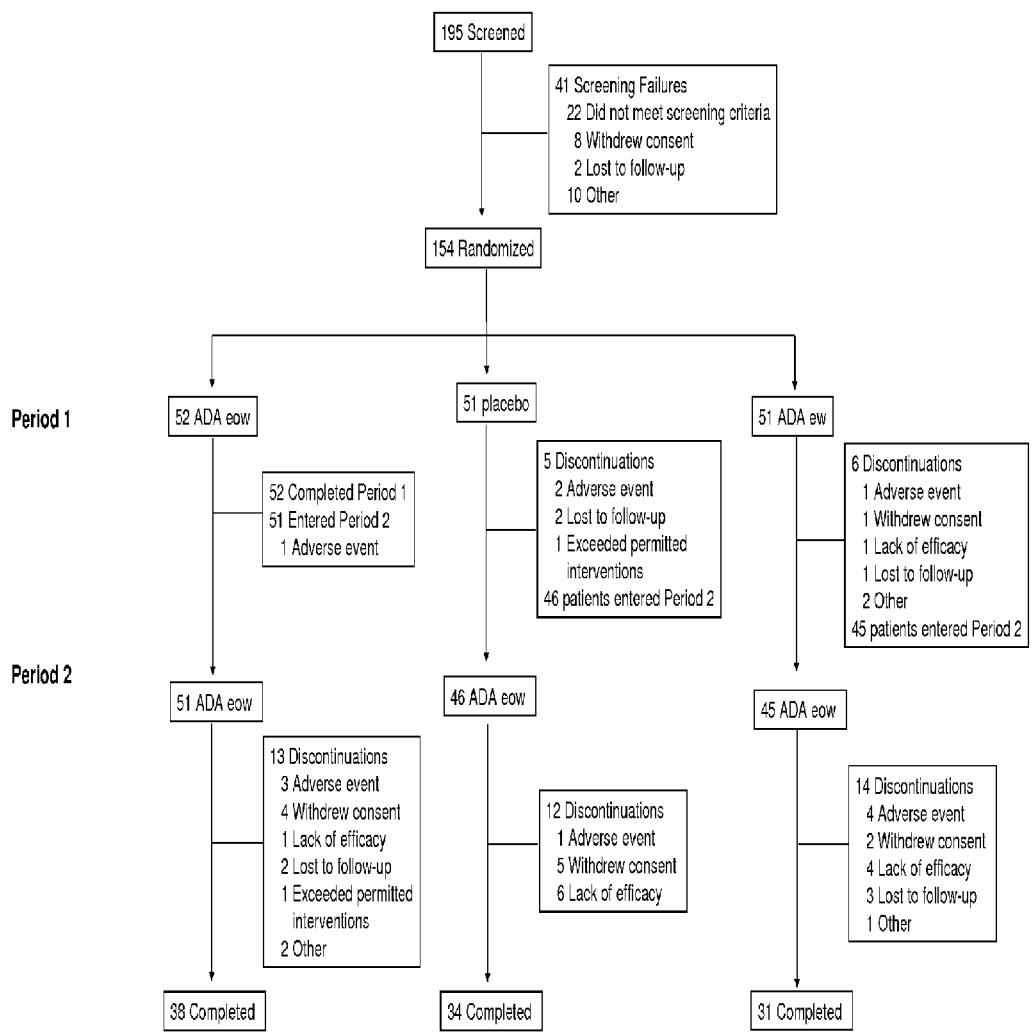

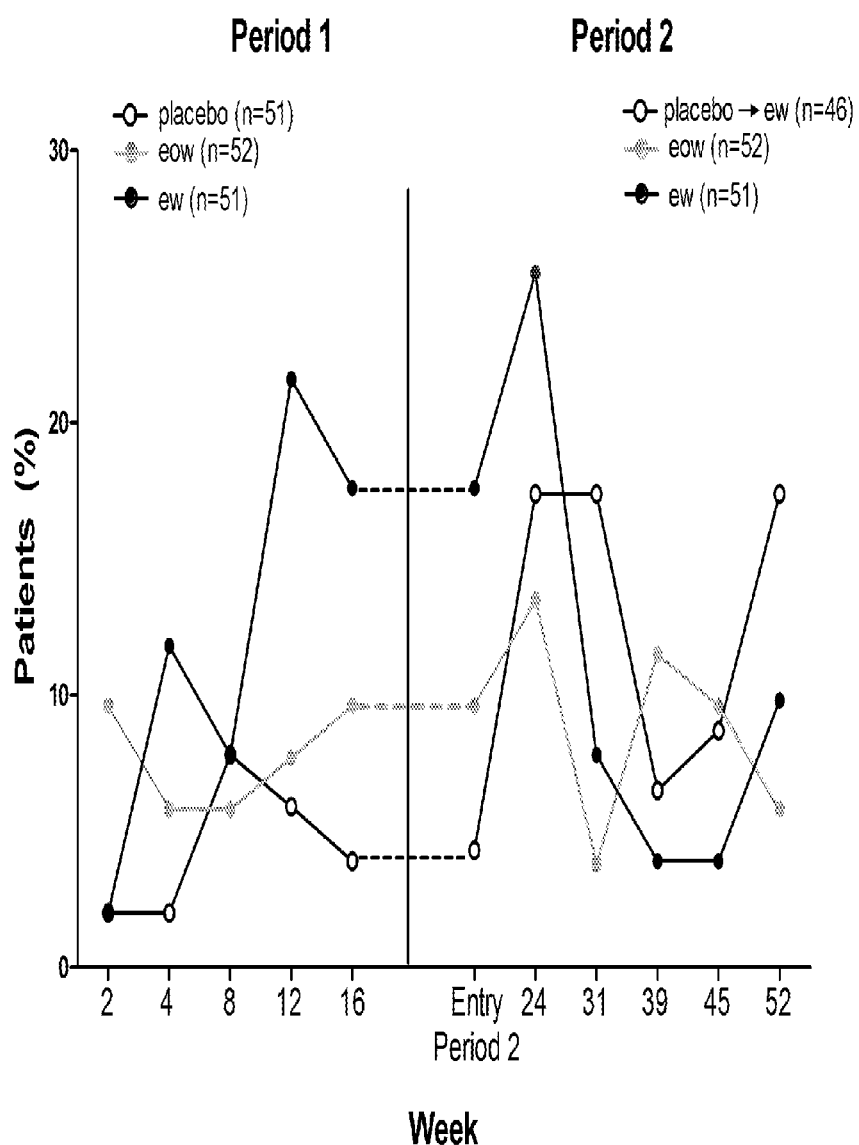

METHODS OF TREATING MODERATE TO SEVERE HIDRADENITIS SUPPURATIVA WITH ANTI-TNFALPHA ANTIBODY

RELATED APPLICATIONS

This application claims the benefit of the filing date under 35 U.S.C. §119(e) of U.S. Provisional Application No. 61/351,125, filed Jun. 3, 2010; U.S. Provisional Application No. 61/430,645, filed Jan. 7, 2011; and U.S. Provisional Application No. 61/474,764, filed Apr. 13, 2011. The entire contents of each of these provisional patent applications are incorporated herein by reference.

BACKGROUND OF THE INVENTION

Hidradenitis suppurativa (HS) refers to a skin disorder of the apocrine glands (sweat glands found on certain parts of the body) and hair follicles in which swollen, painful, chronically inflamed lesions or lumps develop in the groin and sometimes under the arms and under the breasts. Hidradenitis suppurativa is characterized by recurrent inflamed nodules, abscesses, and fistulas, and it occurs when apocrine gland outlets become blocked by perspiration or are unable to drain normally because of incomplete gland development. Secretions trapped in the glands force perspiration and bacteria into surrounding tissue, causing subcutaneous induration, inflammation, and infection. Hidradenitis suppurativa is confined to areas of the body that contain apocrine glands. These areas are the axillae, areola of the nipple, groin, perineum, circumanal, and periumbilical regions.

HS is a chronic inflammatory skin disease, particularly of young adults, and affects approximately 1% of the general population in the West, with women affected 2 to 5 times more commonly than men (Naldi L. Epidemiology. In: Hidradenitis Suppurativa (Jemec G, Revuz J, Leyden J, eds). Heidelberg: Springer. 2006), and with an average age of onset of 23 years. The poorly understood disease is believed to be under-reported by those who suffer from it. HS is also associated with obesity and smoking.

The disease is associated with significant morbidity. Given the pain and consequent physical impairment associated with the tender lesions of this disease, it has been reported that health-related quality of life is lower for patients with hidradenitis suppurativa than other dermatological diseases. In addition, a recent study estimated that up to 20% of patients with HS report the co-existence of depression, and HS patients report a high level of stigmatization. Use of emergency services and antibiotics for incision and drainage of painful abscesses are high when lesions flare.

It is speculated that immunological abnormalities of the hair follicle play a role in the etiology of this disease, and that the underlying mechanisms may be pathogenetically related to those of Crohn's disease (Kurzen et al., Exp Dermatol. 17: 455-456, 2008).

Treatment options have been largely disappointing. Some researchers also suggest that changes in diet, warm compresses and baths, and zinc gluconate supplements can relieve symptoms of HS, bring about remission, and/or minimize recurrence.

To date, no systemic therapy has been demonstrated to be effective for HS in a randomized, double-blind, placebo-controlled trial. Non-evidence-based approaches for moderate to severe HS include long-term antibiotic therapy to control inflammation; case reports or series have described corticosteroids, cyclosporine, or methotrexate as occasionally effective. Surgical intervention is utilized for more advanced HS cases (Alikhan et al., J Am Acad Dermatol. 60: 539-561, 2009). That is, the evidentiary basis behind current therapies for moderate-severe disease, including short- or long-term oral or topical antibiotics, retinoids, intralesional steroids, oral steroids, immunosuppressive agents, radiation, laser therapy, or disfiguring surgical removal of involved areas in more severe cases, is largely limited to anecdotal experience or open-label studies. Surgery is the preferred treatment option in Europe. Currently, there are no approved therapies for this disease in the US.

While some recent case reports have described successful use of tumor necrosis factor-α (TNF-α) antagonists in HS (Haslund et al., Acta Derm Venereol. 89: 595-600, 2009), TNFα antagonists have met with limited success in treating HS. For example, a study examining treatment of HS with etanercept failed to show improvement of HS over a 24-week treatment period (Adams et al., *Arch Dermatol.* 146(5): 501-504, 2010).

SUMMARY OF THE INVENTION

Given the limited success of treatments for hidradenitis suppurativa (HS), there remains a need for an effective treatment, especially in view of the debilitating nature of this disease.

The invention described herein provides a safe and effective treatment of hidradenitis suppurativa (HS) using TNFα inhibitors, particularly human anti-TNFa antibodies, such as adalimumab/D2E7.

Adalimumab is a monoclonal IgG antibody that contains only human peptide sequences. It binds with high specificity and affinity to soluble and membrane-bound TNFα, thereby neutralizing the biological activities of TNFα. Thus, the instant invention provides improved methods and compositions for treating hidradenitis suppurativa.

In one embodiment, the invention provides a means for treating patients suffering from moderate to severe chronic hidradenitis suppurativa.

In one embodiment, the invention provides a means for treating patients suffering from moderate to severe hidradenitis suppurativa.

The invention provides improved methods of treatment, including methods of improving disease reduction in patients having hidradenitis suppurativa and improvements in quality of life for the hidradenitis suppurativa patients.

In one embodiment, the invention provides a method for treating certain subpopulations of patients, including, for example, those who have failed prior therapy or have had a sub-therapeutic response, including, for example, a subject who has an inadequate response to or is intolerant to, or has a contraindication to, oral antibiotics. In certain embodiments, the invention is used to treat HS in a subject who was unresponsive or intolerant to oral antibiotics for treatment for their hidradenitis suppurativa.

In one embodiment, the invention includes the treatment of a subject who has an AN count of greater than or equal to 3 at baseline. In another embodiment, the subject is a female. In a further embodiment, the subject who is over 40 years old. In yet another embodiment, the subject is a smoker.

In yet a further embodiment, the subject may have any combination of the specific features recited herein. For example, the subject may be a female smoker who is over 40 years old and who may have a history of intolerance to antibiotics.

In one embodiment, the TNFα inhibitor, e.g., human TNFα antibody, or antigen-binding portion thereof, is administered weekly. In one embodiment, the TNFα inhibitor, e.g., human TNFα antibody, or antigen-binding portion thereof, is administered every other week (eow or biweekly).

In one embodiment, the invention provides a method of treating hidradenitis suppurativa (HS) in a subject having HS, comprising administering human TNFα antibody, or an antigen-binding portion thereof, such as adalimumab, to the subject as a fixed dose, e.g., about 40 mg, according to a weekly dosing regimen. In one embodiment, the dosing regimen includes an induction dose or doses, followed by weekly dosing of the antibody to treat HS.

In one embodiment, the subject being treated is first selected as having HS and is subsequently treated with a human TNFα antibody, or an antigen-binding portion thereof, according to the methods described herein, e.g., weekly.

In one aspect, the invention provides a method of achieving a clinical response in a subject suffering from hidradenitis suppurativa, comprising administering an effective amount of a human TNFα antibody, or antigen-binding portion thereof, to the subject such that the clinical response in hidradenitis suppurativa is achieved.

In one embodiment, the TNFα inhibitor, e.g., human TNFα antibody, or antigen-binding portion thereof, is administered to the subject on a multiple variable dosing regimen.

In one embodiment, the invention provides a method for treating a subject having hidradenitis suppurativa (HS), the method comprising administering an isolated human anti-TNFa antibody, or an antigen binding portion thereof, to the subject according to a multiple variable dose regimen, such that HS is treated, wherein the multiple variable dose regimen comprises administering a first loading dose, administering a second loading dose which is less than the first loading dose, and administering a treatment dose which is less than the second loading dose, wherein the treatment dose is administered to the subject weekly.

In one embodiment, the invention provides a method for treating a subject having hidradenitis suppurativa (HS), the method comprising administering an isolated human anti-TNFα antibody, or an antigen binding portion thereof, to the subject according to a multiple variable dose regimen, such that HS is treated, wherein the multiple variable dose regimen comprises administering a first loading dose, administering a second loading dose which is less than the first loading dose, and administering a treatment dose which is less than the second loading dose, wherein the treatment dose is administered to the subject biweekly.

In one embodiment, the maintenance dose is administered on a weekly dosing regimen, followed by a biweekly dosing regimen.

In one embodiment, the second loading dose is about 40-60% of the first loading dose. In one embodiment, the treatment dose is about 40-60% of the second loading dose.

In one embodiment, the first loading dose is about 140-180 mg, e.g., about 160 mg.

In one embodiment, the second loading dose is about 60-100 mg, e.g., about 80 mg.

In one embodiment, the treatment dose is about 30-50 mg, e.g., about 40 mg.

In a further embodiment, the invention provides a method for decreasing the number of inflammatory lesions (AN count) in a subject having HS, said method comprising systemically administering an isolated human anti-TNFα antibody, or an antigen binding portion thereof, to the subject, such that the AN count is decreased.

In one embodiment, the AN count is reduced by at least a 50% reduction in the subject relative to baseline AN count.

In one embodiment, the subject has no increase in an abscess count and/or no increase in a draining fistula count following administration with the anti-TNFα antibody, or an antigen binding portion thereof.

In one embodiment, the anti-TNFα antibody, or antigen binding portion thereof, is administered to the subject on a weekly basis.

In yet a further embodiment of the invention, the subject has HS lesions in at least two distinct anatomic areas prior to treatment.

In one embodiment, the TNFα inhibitor, e.g., human TNFα antibody, or antigen-binding portion thereof, is administered to the subject on a weekly or a biweekly dosing regimen, including at a dose of about 40 mg administered weekly or biweekly, respectively.

In yet another embodiment, the TNFα inhibitor, e.g., human TNFα antibody, or antigen-binding portion thereof, is administered to the subject via subcutaneous administration.

In certain embodiments, the clinical response is measured by reduction in pain.

In certain embodiments, the reduction in pain is greater than 30% or greater than 10 mm reduction from a baseline measured at the beginning of the treatment, after 2, 4, 8, 12, or 16 weeks of treatment.

In another aspect, the invention further provides a method of treating hidradenitis suppurativa in a subject comprising administering an initial loading dose of a human TNFα antibody or antigen-binding portion thereof, to the subject, then administering subsequent doses, e.g., maintenance or treatment doses, of the human TNFα antibody or antigen-binding portion thereof, to the subject, wherein the maintenance doses are about one-half to one-fourth of the dose amount of the loading dose. In certain embodiments, the loading dose may comprise one or more doses. In certain embodiments, the loading dose comprises a first dose of about 160 mg and a second dose of about 80 mg, optionally administered 2 weeks apart. In certain other embodiments, the loading dose comprises a single dose of about 80 mg.

In one embodiment, the initial dose is given in its entirety on Day 1 (of week 0), or is given twice, once each at week 0 and week 2. In one embodiment, the second dose, e.g., maintenance or treatment dose, is administered to the subject about one week or two weeks after the last loading dose, and is given on a weekly or biweekly dosing regimen.

In certain embodiments, the loading dose comprises about 160 mg of adalimumab administered at week 0 and about 80 mg of adalimumab administered at week 2, and the maintenance dose comprises weekly administration of about 40 mg of adalimumab starting from week 4.

In certain embodiments, the loading dose comprises about 80 mg of adalimumab administered at week 0, and the maintenance dose comprises biweekly/every-other-week (eow) administration of about 40 mg of adalimumab starting from week 1.

In one embodiment, the invention provides a method of improving (i.e., reducing) a Hidradenitis Suppurativa-Physician's Global Assessment (HS-PGA) score of a subject having hidradenitis suppurativa from a high score (e.g., an HS-PGA score of 3 or more) to a no or small impact score (e.g., an HS-PGA score of 0-2), comprising administering a TNFα inhibitor, e.g., human TNFα antibody, or antigen-binding portion thereof, to the subject, such that the HS-PGA score improves from the high score to the no or small impact score. The invention also provides a method of decreasing an HS-PGA score of a subject having hidradenitis suppurativa by at least about 2 grades, comprising administering a TNFα inhibitor, e.g., human TNFα antibody, or antigen-binding portion thereof, to the subject, such that the HS-PGA score is decreased by at least about 2 grades.

In one aspect, the invention provides a method of decreasing an HS-PGA score of a subject having hidradenitis suppurativa from a high score (e.g., a score of 3 or more) to a no or small impact score (e.g., a score of 0-2), comprising administering a human TNFα antibody to the subject, such that the HS-PGA score is decreased from the high score to the no or small impact score.

In one aspect, the invention provides a method of decreasing an HS-PGA score of a subject having hidradenitis suppurativa by at least about 2 grades, comprising administering a human TNFα antibody to the subject, such that the HS-PGA score is decreased by at least about 2 grades.

The invention also includes administering an effective TNFα inhibitor, e.g., human TNFα antibody, or antigen-binding portion thereof, to a subject or patient population having hidradenitis suppurativa.

In one embodiment, the TNFα inhibitor, e.g., human TNFα antibody, or antigen-binding portion thereof, is administered to the patient population or subject on a weekly or biweekly dosing regimen.

In still another embodiment, the TNFα inhibitor is administered in a multiple variable dose regimen. In one embodiment, the multiple variable dose regimen comprises one or more induction or loading doses, which are at least double or quadruple the treatment or maintenance doses. In certain embodiments, the TNFα inhibitor is administered weekly or biweekly to the patient population or subject. In one embodiment, the induction dose comprises about 160 or 80 mg. In one embodiment, the treatment dose comprises about 40 mg.

In one embodiment, the TNFα inhibitor, e.g., human TNFα antibody, or antigen-binding portion thereof, is administered to the patient population or subject at a dose of about 40 mg on a weekly or biweekly dosing regimen.

In another embodiment, the TNFα inhibitor, e.g., human TNFα antibody, or antigen-binding portion thereof, is administered to the patient population or subject via subcutaneous administration.

The invention provides an article of manufacture comprising: a human TNFα antibody, or antigen-binding portion thereof, and a label or package insert contained within the packaging material indicating that an adverse event which has been reported in the use of the human TNFα antibody is super infection of hidradenitis suppurativa lesions and/or pilonidal cyst flare.

The invention includes a package comprising a TNFα inhibitor and instructions for administering the TNFα inhibitor to a human subject for the treatment of adults with hidradenitis suppurativa, e.g., moderate to severe chronic hidradenitis suppurativa, who have been unresponsive or intolerant to oral antibiotics for treatment for their hidradenitis suppurativa. The invention also includes a package comprising a TNFα inhibitor, wherein the package contains, on the label and in a position which is visible to a subject, including a prospective purchaser, a printed statement which informs a subject, including a prospective purchaser, that the TNFα inhibitor is indicated for the treatment of adults with moderate to severe chronic hidradenitis suppurativa who have been unresponsive or intolerant to oral antibiotics for treatment for their hidradenitis suppurativa.

The invention further provides a package comprising a TNFα inhibitor, wherein the package contains, on the label and in a position which is visible to a subject, including a prospective purchaser, a printed statement which informs a subject, including a prospective purchaser, that the recommended dose of the TNFα inhibitor for patients with hidradenitis suppurativa is 40 mg TNFα inhibitor administered every week or every other week, as a single dose via subcutaneous injection.

In one aspect, the invention provides an article of manufacture comprising a human TNFα antibody and a package insert, wherein the package insert indicates the recommended human TNFα antibody dose regimen for adult patients with hidradenitis suppurativa is about 160 mg at week 0, about 80 mg at week 2, followed by 40 mg every week beginning at week 4.

In one aspect, the invention provides an article of manufacture comprising a human TNFα antibody and a package insert, wherein the package insert indicates the recommended human TNFα antibody dose regimen for adult patients with hidradenitis suppurativa is about 80 mg at week 0, followed by about 40 mg every other week beginning at week 1.

In one aspect, the invention provides an article of manufacture which comprising adalimumab and a package insert, wherein the package insert indicates that the adalimumab may be used to treat hidradenitis suppurativa in patients who have been unresponsive or intolerant to oral antibiotics for treatment for their hidradenitis suppurativa.

The invention also provides a means for determining the efficacy of a TNFα inhibitor for the treatment of hidradenitis suppurativa.

The invention further provides a method of determining the efficacy of a TNFα inhibitor, e.g., a human TNFα antibody, or an antigen-binding portion thereof, for treating hidradenitis suppurativa in a subject, comprising determining a proportion of treated subjects achieving Hidradenitis Suppurativa Clinical Response (HiSCR) within a patient population having hidradenitis suppurativa who was administered the human TNFα antibody, or antigen-binding portion thereof, wherein a statistically significant (e.g., $p<0.05$, or $p<0.01$, or $p<0.005$, or $p<0.001$) increase in the proportion achieving clinical response in the treatment group compared to placebo indicates that the TNFα inhibitor, e.g., human TNFα antibody, or antigen-binding portion thereof, is an effective TNFα inhibitor, e.g., human TNFα antibody, or antigen-binding portion thereof, for the treatment of hidradenitis suppurativa in the subject.

In one embodiment, at least about 5, 6, 7, 8, 9, 10, 11, 12, 13, 14, 15, 16, 17, 18, 19, 20, 21, 22, 23, 24, 25% or more of the patient population achieve statistically significant Hidradenitis Suppurativa Clinical Response (HiSCR) indicates that the TNFα inhibitor, e.g., human TNFα antibody, or antigen-binding portion thereof, is an effective human TNFα antibody, or antigen-binding portion thereof, for the treatment of hidradenitis suppurativa in the subject.

In one embodiment, the invention includes a method for determining the efficacy of a TNFα inhibitor, e.g., human TNFα antibody, or an antigen-binding portion thereof, for improving the functional limitations of a subject having hidradenitis suppurativa comprising determining an improvement in an HS-PGA score from a patient population administered with the TNFα inhibitor, e.g., human TNFα antibody, or antigen-binding portion thereof, wherein a statistically significant difference in reduction of the HS-PGA score (e.g., by at least 2 grades, and/or to an HS-PGA score of 0-2) for the patient population indicates that the human TNFα antibody, or antigen-binding portion thereof, is an effective TNFα inhibitor, e.g., human TNFα antibody, or antigen-binding portion thereof, for improving the functional limitations of a subject having hidradenitis suppurativa.

The invention further provides a method of determining the efficacy of a TNFα inhibitor, e.g., a human TNFα antibody, or an antigen-binding portion thereof, for treating hidradenitis suppurativa in a subject, comprising determining a proportion of treated subject achieving clinical response (e.g., as defined by HS-PGA score reduction) within a patient population having hidradenitis suppurativa who was administered the human TNFα antibody, or antigen-binding portion thereof, wherein a statistically significant (e.g., p<0.05, or p<0.01, or p<0.005, or p<0.001) increase in the proportion achieving clinical response in the treatment group compared to placebo indicates that the TNFα inhibitor, e.g., human TNFα antibody, or antigen-binding portion thereof, is an effective TNFα inhibitor, e.g., human TNFα antibody, or antigen-binding portion thereof, for the treatment of hidradenitis suppurativa in the subject.

In one embodiment, at least about 5, 6, 7, 8, 9, 10, 11, 12, 13, 14, 15, 16, 17, 18, 19, 20, 21, 22, 23, 24, 25% or more of the patient population achieve statistically significant clinical response (e.g., as measured by reduction of HS-PGA score as defined herein) indicates that the TNFα inhibitor, e.g., human TNFα antibody, or antigen-binding portion thereof, is an effective human TNFα antibody, or antigen-binding portion thereof, for the treatment of hidradenitis suppurativa in the subject.

The invention also provides a method of treating hidradenitis suppurativa in a subject comprising administering an effective amount of a TNFα inhibitor, e.g., human TNFα antibody, or antigen-binding portion thereof, to the subject, wherein the effective amount of the TNFα inhibitor, e.g., human TNFα antibody, or antigen-binding portion thereof, has previously been identified as achieving a statistically significant clinical response in at least about 5, 6, 7, 8, 9, 10, 11, 12, 13, 14, 15, 16, 17, 18, 19, 20, 21, 22, 23, 24, 25% or more of a patient population having hidradenitis suppurativa. Ranges of values using a combination of any of the above recited values as upper and/or lower limits are intended to be included in the scope of the invention.

In one embodiment, the efficacy of a TNFα inhibitor for treating hidradenitis suppurativa in a patient population may be evaluated by determining the percentage of the patient population achieving Hidradenitis Suppurativa Clinical Response (HiSCR). HiSCR is defined as at least a 50% reduction in the total inflammatory lesion (abscess and nodule) count (AN count) relative to baseline with no increase in abscess count and no increase in draining fistula count.

In one embodiment, the efficacy of a TNFα inhibitor for treating hidradenitis suppurativa in a patient population may be evaluated by determining the percentage of the patient population achieving clinical response (as defined by HS-PGA score reduction) for whom the TNFα inhibitor has been effective for treating hidradenitis suppurativa.

In one embodiment, the invention provides a kit for the treatment of HS in a subject, said kit comprising containers providing the loading dose(s) and/or treatment dose(s), e.g., at least seven containers, of an isolated human anti-TNFa antibody, or an antigen binding portion thereof. The kit may also further provide instructions for administration of the anti-TNFa antibody, or antigen binding portion thereof, to a subject having HS. In one embodiment, the container is a preloaded syringe. In one embodiment, the container is an autoinjector. In one embodiment, each container in the kit contains about 40 mg of the anti-TNFa antibody, or antigen binding portion thereof.

In one embodiment, the TNFα inhibitor is selected from the group consisting of an anti-TNFα antibody, or an antigen-binding portion thereof, a TNF fusion protein, or a recombinant TNF binding protein.

In one embodiment, the TNF fusion protein is etanercept.

In one embodiment, the TNFα antibody, or antigen-binding portion thereof, is selected from the group consisting of a chimeric antibody, a humanized antibody, and a multivalent antibody.

In one embodiment of the invention, the TNFα antibody, or antigen-binding portion thereof, is a human antibody.

In another embodiment, the TNFα antibody, or antigen-binding portion thereof, is an isolated human antibody that dissociates from human TNFα with a $K_d$ of $1 \times 10^{-8}$ M or less and a $k_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less.

In certain embodiments, the TNFα antibody is an isolated human antibody, or antigen-binding portion thereof, with the following characteristics: a) dissociates from human TNFα with a $k_{off}$ rate constant of $1 \times 10^{-3}$ s$^{-1}$ or less, as determined by surface plasmon resonance; (b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9; (c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In one embodiment, the TNFα antibody is an isolated human antibody, or an antigen binding portion thereof, comprising a light chain variable region comprising CDRs having the amino acid sequences described in SEQ ID NOs: 3, 5, and 7, and a heavy chain variable region comprising CDRs having the amino acid sequences described in SEQ ID NOs: 4, 6, and 8.

In one embodiment, the TNFα antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2.

In one embodiment, the anti-TNFα antibody, or antigen-binding portion thereof, is adalimumab.

In one embodiment, the anti-TNFα antibody, or antigen-binding portion thereof, is an adalimumab biosimilar antibody or an adalimumab interchangeable antibody.

In one embodiment, the TNFα antibody, or antigen-binding portion thereof, is a 40 mg dose.

In another embodiment, the TNFα antibody, or antigen-binding portion thereof, is administered subcutaneously.

In certain embodiments, the TNFα antibody, or antigen-binding portion thereof, is infliximab or golimumab. In yet another embodiment, the TNFα antibody, or antigen-binding portion thereof, is certolizumab.

In one embodiment, the TNFα inhibitor is administered weekly to the patient population or subject having hidradenitis suppurativa. In another embodiment, TNFα inhibitor is administered biweekly to the patient population or subject having hidradenitis suppurativa.

In is contemplated that, all embodiments described herein, including those described under different aspects of the invention, can be combined with one another where not specifically prohibited.

BRIEF DESCRIPTION OF THE DRAWINGS

FIG. 2 shows disposition of patients screened for the study. ADA: adalimumab; eow: every other week; ew: every week.

FIG. 3 shows efficacy of adalimumab over 52 weeks. A significantly greater proportion of patients in the ew group achieved the primary endpoint, a clinical response at Week 16, compared with patients allocated to the placebo group; *p<0.05, ew vs. placebo, ITT analysis.

DETAILED DESCRIPTION OF THE INVENTION

I. Definitions

Figure 1:
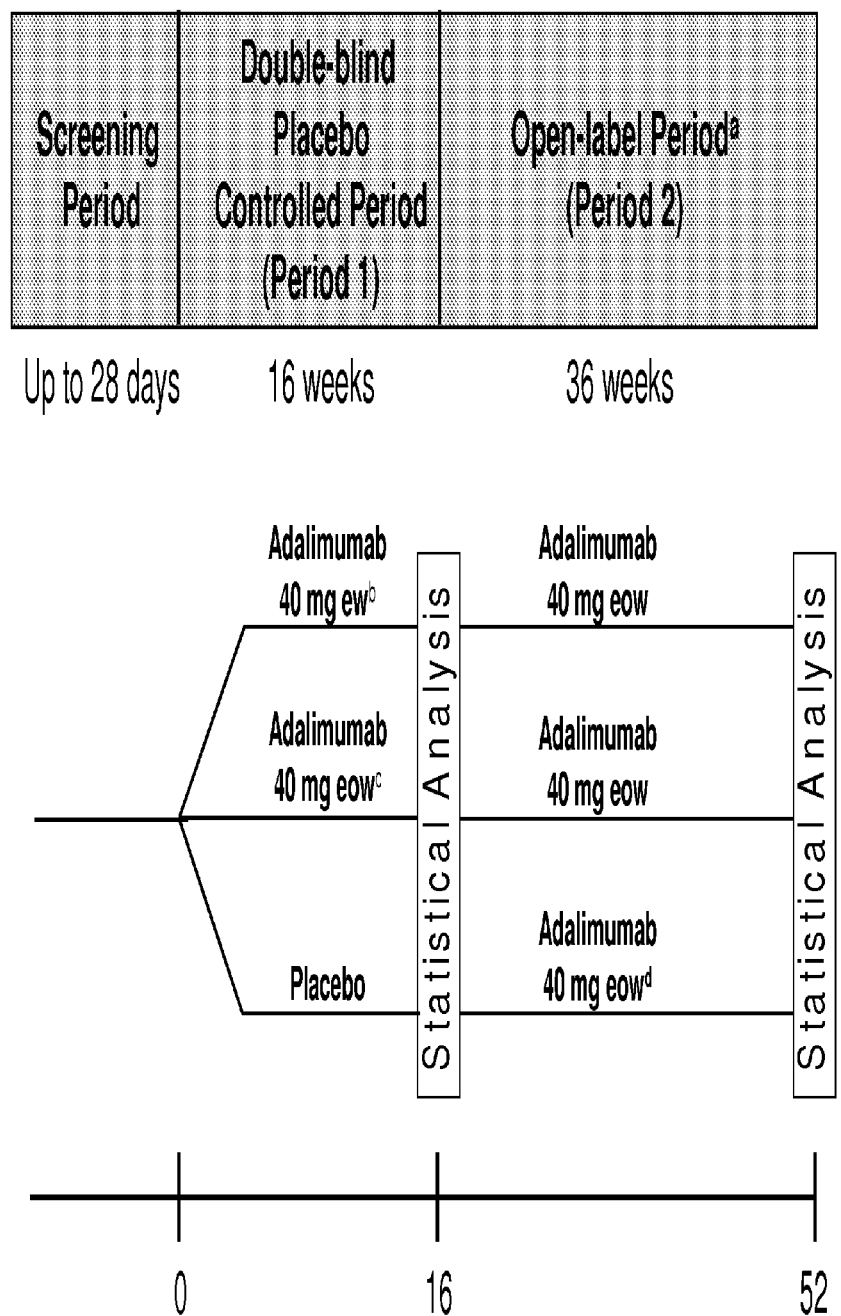
FIG. 1 shows the study design for the Phase II clinical trial described in Examples 1-5. a: Dose escalation to ew dosing for patients with PGA≥3 at Weeks 28 or 31. b: From Week 4, after 160 mg dose at Week 0, 80 mg at Week 2. c: From Week 1, after 80 mg dose at Week 0. d: From Week 17, after 80 mg dose at Week 16.

The term "human TNFα" (abbreviated herein as hTNFα, or simply hTNF), as used herein, is intended to refer to a human cytokine that exists as a 17 kDa secreted form and a 26 kDa membrane associated form, the biologically active form of which is composed of a trimer of non-covalently bound 17 kDa molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF. In addition, the terms "TNFα antibody" and "anti-TNFα antibody" are used interchangeably throughout.

The term "TNFα inhibitor" includes agents which interfere with TNFα activity. The term also includes each of the anti-TNFα human antibodies and antibody portions described herein as well as those described in U.S. Pat. Nos. 6,090,382; 6,258,562; 6,509,015, and in U.S. patent application Ser. Nos. 09/801,185 and 10/302,356. In one embodiment, the TNFα inhibitor used in the invention is an anti-TNFα antibody, or a fragment thereof, including infliximab (REMICADE®, Centocor; described in U.S. Pat. No. 5,656,272, incorporated by reference herein), CDP571 (a humanized monoclonal anti-TNF-alpha IgG4 antibody), CIMZIA® (certolizumab (or CDP870) a humanized monoclonal anti-TNF-alpha antibody fragment; UCB), an anti-TNF dAb (Peptech), SIMPONI® (golimumab; also referred to as CNTO 148; Centocor Ortho Biotech, see WO 02/12502), and adalimumab (HUMIRA®, Abbott Laboratories, a human anti-TNFα mAb, described in U.S. Pat. No. 6,090,382 as D2E7). Additional TNFα antibodies which may be used in the invention are described in U.S. Pat. Nos. 6,593,458; 6,498,237; 6,451,983; and 6,448,380, each of which is incorporated by reference herein. In another embodiment, the TNFα inhibitor is a TNF-R fusion protein, e.g., etanercept (ENBREL®, Amgen; described in WO 91/03553 and WO 09/406476, incorporated by reference herein). In another embodiment, the TNFα inhibitor is a recombinant TNF binding protein (r-TBP-I) (Serono).

The term "antibody," as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety.

The term "antigen-binding portion" or "antigen-binding fragment" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Binding fragments include Fab, Fab', F(ab')$_2$, Fabc, Fv, single chains, and single-chain antibodies. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382, 6,258,562, 6,509,015, each of which is incorporated herein by reference in its entirety. Still further, an antibody or antigen-binding portion thereof may be part of a larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

A "clinical response" as used herein is refers to an indicator of therapeutic effectiveness of an agent. In one embodiment, a clinical response is defined by whether or not a subject achieves an HiSCR. In another embodiment, a clinical response is defined as achieving an Hidradenitis Suppurativa Physician's Global Assessment (HS-PGA) score, or HS-PGA score, as defined below in Table 1, of clear (0), minimal (1), or mild (2), with an improvement (i.e., reduction) from baseline HS-PGA score of at least 2 grades. The baseline HS-PGA score is the HS-PGA score measured just prior to the commence of treatment, to which the HS-PGA score obtained after a period of treatment is compared. Both the baseline HS-PGA score and the HS-PGA score obtained after a treatment period are assessed based on the system and criteria in Table 1.

The term "Hidradenitis Suppurativa Clinical Response" or "HiSCR" as used herein is defined as at least a 50% reduction in the total inflammatory lesion (abscess and nodule) count (AN count) relative to baseline with no increase in abscess count and no increase in draining fistula count.

A "conservative amino acid substitution," as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Chimeric antibodies" refers to antibodies wherein one portion of each of the amino acid sequences of heavy and light chains is homologous to corresponding sequences in antibodies derived from a particular species or belonging to a particular class, while the remaining segment of the chains is homologous to corresponding sequences from another species. In one embodiment, the invention features a chimeric antibody or antigen-binding fragment, in which the variable regions of both light and heavy chains mimics the variable regions of antibodies derived from one species of mammals, while the constant portions are homologous to the sequences in antibodies derived from another species. In one embodiment of the invention, chimeric antibodies are made by grafting CDRs from a mouse antibody onto the framework regions of a human antibody.

"Humanized antibodies" refer to antibodies which comprise at least one chain comprising variable region framework residues substantially from a human antibody chain (referred to as the acceptor immunoglobulin or antibody) and at least one complementarity determining region (CDR) substantially from a non-human-antibody (e.g., mouse). In addition to the grafting of the CDRs, humanized antibodies typically undergo further alterations in order to improve affinity and/or immmunogenicity.

The term "multivalent antibody" refers to an antibody comprising more than one antigen recognition site. For example, a "bivalent" antibody has two antigen recognition sites, whereas a "tetravalent" antibody has four antigen recognition sites. The terms "monospecific," "bispecific," "trispecific," "tetraspecific," etc. refer to the number of different antigen recognition site specificities (as opposed to the number of antigen recognition sites) present in a multivalent antibody. For example, a "monospecific" antibody's antigen recognition sites all bind the same epitope. A "bispecific" or "dual specific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "human antibody," as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173, 494; PCT International Publication No. WO 86/01533; U.S. Pat. No. 4,816,567; European Patent Application No. 125, 023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314: 446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141: 4053-4060, Queen et al., *Proc. Natl. Acad. Sci. USA*

86:10029-10033 (1989), U.S. Pat. Nos. 5,530,101, 5,585,089, 5,693,761, 5,693,762, Selick et al., WO 90/07861, and Winter, U.S. Pat. No. 5,225,539.

An "isolated antibody," as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

A "neutralizing antibody," as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance," as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198: 268.

The term "$k_{off}$," as used herein, is intended to refer to the off rate constant for dissociation of an antibody from the antibody/antigen complex.

The term "$K_d$," as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "dose," as used herein, refers to an amount of TNFα inhibitor (e.g., an anti-TNFα antibody) which is administered to a subject.

The term "dosing," as used herein, refers to the administration of a TNFα inhibitor (e.g., an anti-TNFα antibody) to achieve a therapeutic objective (e.g., treatment of hidradenitis suppurativa).

A "dosing regimen" describes a treatment schedule for a TNFα inhibitor (e.g., an anti-TNFα antibody, or an antigen-binding portion thereof), e.g., a treatment schedule over a prolonged period of time or throughout the course of treatment, e.g. administering a first dose of a TNFα inhibitor (e.g., an anti-TNFα antibody, or an antigen-binding portion thereof) at week 0 followed by a second dose of a TNFα inhibitor (e.g., an anti-TNFα antibody, or an antigen-binding portion thereof) on a weekly or biweekly dosing regimen.

The term "multiple-variable dose" includes different doses of a TNFα inhibitor (e.g., an anti-TNFα antibody, or an antigen-binding portion thereof) which are administered to a subject for therapeutic treatment. "Multiple-variable dose regimen" or "multiple-variable dose therapy" describes a treatment schedule which is based on administering different amounts of TNFα inhibitor (e.g., an anti-TNFα antibody, or an antigen-binding portion thereof) at various time points throughout the course of treatment. Exemplary multiple-variable dose regimens are described in PCT application no. PCT/US05/12007 and US 20060009385, which is incorporated by reference herein.

The term "induction dose" or "loading dose," used interchangeably herein, refers to the first dose(s) of TNFα inhibitor (e.g., an anti-TNFα antibody, or an antigen-binding portion thereof) which is initially used to treat hidradenitis suppurativa. The loading dose may be larger in comparison to the subsequent maintenance or treatment dose. The induction dose can be a single dose or, alternatively, a set of doses. For example, a 160 mg dose may be administered as a single 160 mg dose, as two doses of 80 mg each, or four doses of 40 mg each. In one embodiment, an induction dose is subsequently followed by administration of smaller doses of TNFα inhibitor (e.g., an anti-TNFα antibody, or an antigen-binding portion thereof), e.g., the treatment or maintenance dose(s). The induction dose is administered during the induction or loading phase of therapy. In one embodiment of the invention, the induction dose is at least twice the given amount of the treatment dose. In one embodiment of the invention, the induction dose is 80 mg. In one embodiment of the invention, the induction dose comprise a 160 mg dose followed by an 80 mg dose, wherein the two induction doses are administered 2 weeks apart.

The term "maintenance therapy" or "maintenance dosing regimen" refers to a treatment schedule for a subject or patient diagnosed with a disorder/disease, e.g., hidradenitis suppurativa, to enable them to maintain their health in a given state, e.g., reduced number of inflammatory lesions or achieving a clinical response. In one embodiment, a maintenance therapy of the invention is used for a subject or patient diagnosed with a disorder/disease, e.g., hidradenitis suppurativa to enable them to maintain their health in a state which is completely free of symptoms or a reduction in symptoms associated with the disease. In one embodiment, a maintenance therapy of the invention is used for a subject or patient diagnosed with a disorder/disease, e.g., hidradenitis suppurativa, to enable them to maintain their health in a state which is substantially free of symptoms associated with the disease. In one embodiment, a maintenance therapy of the invention is used for a subject or patient diagnosed with a disorder/disease, e.g., hidradenitis suppurativa, to enable them to maintain their health in a state where there is a significant reduction in symptoms associated with the disease.

The term "treatment phase" or "maintenance phase," as used herein, refers to a period of treatment comprising administration of a TNFα inhibitor (e.g., an anti-TNFα antibody) to a subject in order to maintain a desired therapeutic effect, e.g., improved symptoms associated with hidradenitis suppurativa.

The term "maintenance dose" or "treatment dose" is the amount of TNFα inhibitor (e.g., an anti-TNFα antibody, or an antigen-binding portion thereof) taken by a subject to maintain or continue a desired therapeutic effect. A maintenance dose can be a single dose or, alternatively, a set of doses. A maintenance dose is administered during the treatment or maintenance phase of therapy. In one embodiment, a maintenance dose(s) is smaller than the induction dose(s) and may be equal to each other when administered in succession. In one embodiment, the invention provides a maintenance dose of 40 mg of adalimumab administered subcutaneously to a subject weekly or biweekly. In one embodiment, the maintenance dose is administered every week or every other week beginning 1 ot 2 weeks after the last loading dose. In one embodiment, a maintenance dose is administered about 4 weeks following the initial loading dose.

The terms "biweekly dosing regimen," "biweekly dosing," and "biweekly administration," as used herein, refer to the time course of administering a substance (e.g., an anti-TNFα antibody, or an antigen-binding portion thereof) to a subject to achieve a therapeutic objective, e.g., throughout the course of treatment. The biweekly dosing regimen is not intended to include a weekly dosing regimen. Preferably, the substance is administered every 9-19 days, or $10^{-18}$ days, more preferably, every 11-17 days, or 12-16 days, even more preferably, every 13-15 days, and most preferably, every 14 days. In one embodiment, the biweekly dosing regimen is initiated in a subject at week 0 of treatment. In another embodiment, a maintenance dose is administered on a biweekly dosing regimen. In one embodiment, both the loading and maintenance doses are administered according to a biweekly dosing regimen. In one embodiment, biweekly dosing includes a dosing regimen where doses of a TNFα inhibitor (e.g., an anti-TNFα antibody, or an antigen-binding portion thereof) are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing methods are also described in US 20030235585, incorporated by reference herein. Biweekly administration is also referred to as "eow" or "every other week".

The terms "qwk," "qw," or "ew," as used interchangeably herein, refer to a weekly dosing regimen, where a substance (e.g., a human anti-TNFα antibody, or an antigen-binding portion thereof) is administered to a subject once a week (or every week) to achieve a therapeutic objective, e.g., treating HS. A "weekly dosing regimen" as used herein, refers to the time course of administering a substance (e.g., an anti-TNFα antibody) to a subject to achieve a therapeutic objective, e.g., throughout the course of treatment. Weekly administration is more frequent than biweekly, e.g, every 6-8 days, every 5-8 days, or every 7 days.

The term "fixed dose" or "total body dose" refers to a dose which is a constant amount delivered with each administration and is not dependent on the weight of the subject being treated. The term "fixed dose" dose not include weight-based dosing, i.e., mg/kg dosing determinations. In one embodiment, a human TNFα antibody, or antigen-binding portion thereof, is administered to the subject at a fixed dose ranging from 10-180 mg. In one embodiment, a human TNFα antibody, or antigen-binding portion thereof, is administered to the subject in a fixed dose of 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg etc. Ranges of values between any of the aforementioned recited values are also intended to be included in the scope of the invention, e.g., 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 85 mg, 95 mg, as are ranges based on the aforementioned doses, e.g., 30-50 mg, 20-80 mg, 20-70 mg, 20-60 mg, and 20-50 mg.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy," as used herein, refers to the administration of two or more therapeutic substances, e.g., an anti-TNFα antibody and another drug. The other drug(s) may be administered concomitant with, prior to, or following the administration of an anti-TNFα antibody.

The term "treatment," as used within the context of the present invention, is meant to include therapeutic treatment, as well as prophylactic or suppressive measures, for the treatment of hidradenitis suppurativa. For example, the term treatment may include administration of a TNFα inhibitor prior to or following the onset of hidradenitis suppurativa thereby preventing or removing signs of the disease or disorder. As another example, administration of a TNFα inhibitor after clinical manifestation of hidradenitis suppurativa to combat the symptoms and/or complications and disorders associated with hidradenitis suppurativa comprises "treatment" of the disease. Further, administration of the agent after onset and after clinical symptoms and/or complications have developed where administration affects clinical parameters of the disease or disorder and perhaps amelioration of the disease, comprises "treatment" of the hidradenitis suppurativa.

Those "in need of treatment" include mammals, such as humans, already having hidradenitis suppurativa, including those in which the disease or disorder is to be prevented.

The terms "subject" and "patient", as used herein, are used interchangeably. In one embodiment, a subject refers to an individual who may be treated therapeutically with a TNFa inhibitor, e.g., a human TNFα antibody, or an antigen-binding portion thereof.

Various aspects of the invention are described in further detail herein.

The invention provides improved uses and compositions for treating hidradenitis suppurativa disease with a TNFα inhibitor, e.g., a human TNFα antibody, or an antigen-binding portion thereof. Compositions and articles of manufacture, including kits, relating to the methods and uses for treating hidradenitis suppurativa are also contemplated as part of the invention.

II. TNF Inhibitors

A TNFα inhibitor which is used in the methods and compositions of the invention includes any agent which interferes with TNFα activity. In a preferred embodiment, the TNFα inhibitor can neutralize TNFα activity, particularly detrimental TNFα activity which is associated with hidradenitis suppurativa, and related complications and symptoms.

In one embodiment, the TNFα inhibitor used in the invention is an TNFα antibody (also referred to herein as a TNFα antibody), or an antigen-binding fragment thereof, including chimeric, humanized, and human antibodies. Examples of TNFα antibodies which may be used in the invention include, but not limited to, infliximab (REMICADE®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), SIMPONI (golimumab) (also referred to as CNTO 148; Centocor Ortho Biotech, see WO 02/12502), CIMZIA (certolizumab) (UCB), and adalimumab (HUMIRA®, Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein.

Other examples of TNFα inhibitors which may be used in the methods and compositions of the invention include etanercept (ENBREL™, described in WO 91/03553 and WO 09/406476), soluble TNF receptor Type I, a PEGylated soluble TNF receptor Type I (PEGs TNF-R1), p55 TNFRIgG (Lenercept), and recombinant TNF binding protein (r-TBP-I) (Serono).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

In one embodiment, the invention features uses and composition for treating or determining the efficacy of a TNFα antibody, or antigen binding portion thereof, for the treatment of hidradenitis suppurativa, wherein the TNFα antibody, or antigen binding portion thereof, is an isolated human antibody, or antigen-binding portion thereof, that binds to human TNFα with high affinity and a low off rate, and also has a high neutralizing capacity. Preferably, the human antibodies used in the invention are recombinant, neutralizing human anti-hTNFα antibodies. The most preferred recombinant, neutralizing antibody of the invention is HUMIRA® (adalimumab; also referred to as D2E7 (the amino acid sequence of the adalimumab VL region is shown in SEQ ID NO: 1; the amino acid sequence of the adalimumab VH region is shown in SEQ ID NO: 2). The properties and sequences of adalimumab/HUMIRA® (also referred to as D2E7) have been described in Salfeld et al., U.S. Pat. Nos. 6,090,382, 6,258,562, and 6,509,015, which are each incorporated by reference herein.

The methods of the invention may also be performed using chimeric and humanized murine anti-hTNFα antibodies which have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

In one embodiment, the method of the invention includes determining the efficacy of adalimumab and antibody portions, adalimumab-related antibodies and antibody portions, or other human antibodies and antibody portions with equivalent properties to adalimumab, such as high affinity binding to hTNFα with low dissociation kinetics and high neutralizing capacity, for the treatment of hidradenitis suppurativa. In one embodiment, the invention provides treatment with an isolated human antibody, or an antigen-binding portion thereof, that dissociates from human TNFα with a $K_d$ of $1\times10^{-8}$ M or less and a $k_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less. More preferably, the isolated human antibody, or antigen-binding portion thereof, dissociates from human TNFα with a $k_{off}$ of $5\times10^{-4}$ s$^{-1}$ or less, or even more preferably, with a $k_{off}$ of $1\times10^{-4}$ s$^{-1}$ or less. More preferably, the isolated human antibody, or antigen-binding portion thereof, neutralizes human TNFα cytotoxicity in a standard in vitro L929 assay with an $IC_{50}$ of $1\times10^{-8}$ M or less, even more preferably with an $IC_{50}$ of $1\times10^{-9}$ M or less and still more preferably with an $IC_{50}$ of $1\times10^{-10}$ M or less. Notably, the aforementioned characteristics are all properties of adalimumab. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to treating hidradenitis suppurativa by administering human antibodies that have slow dissociation kinetics for association with hTNFα and that have light and heavy chain CDR3 domains that structurally are identical to or related to those of adalimumab. Position 9 of the adalimumab VL CDR3 can be occupied by Ala or Thr without substantially affecting the $K_{off}$. Accordingly, a consensus motif for the adalimumab VL CDR3 comprises the amino acid sequence: Q-R-Y-N-R-A-P-Y-(T/A) (SEQ ID NO: 3). Additionally, position 12 of the adalimumab VH CDR3 can be occupied by Tyr or Asn, without substantially affecting the $K_{off}$. Accordingly, a consensus motif for the adalimumab VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the adalimumab heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $k_{off}$. Still further, the skilled artisan will appreciate that, given the amenability of the adalimumab VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the adalimumab VL and/or VH CDR3 domains. More preferably, no more than one to three conservative amino acid substitutions are made within the adalimumab VL and/or VH CDR3 domains. Additionally, conservative amino acid substitutions should not be made at amino acid positions critical for binding to hTNFα. Positions 2 and 5 of the adalimumab VL CDR3 and positions 1 and 7 of the adalimumab VH CDR3 appear to be critical for interaction with hTNFα and thus, conservative amino acid substitutions preferably are not made at these positions (although an alanine substitution at position 5 of the adalimumab VL CDR3 is acceptable, as described above) (see U.S. Pat. No. 6,090,382).

Accordingly, in another embodiment, the antibody or antigen-binding portion thereof preferably contains the following characteristics:

a) dissociates from human TNFα with a $k_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $k_{off}$ of $5\times10^{-4}$ s$^{-1}$ or less. Even more preferably, the antibody, or antigen-binding portion thereof, dissociates from human TNFα with a $k_{off}$ of $1\times10^{-4}$ s$^{-1}$ or less.

In yet another embodiment, the antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. In one embodiment, the LCVR further has a CDR2 domain comprising the amino acid sequence of SEQ ID NO: 5 (i.e., the adalimumab VL CDR2) and the HCVR further has a CDR2 domain comprising the amino acid sequence of SEQ ID NO: 6 (i.e., the adalimumab VH CDR2). In one embodiment, the LCVR further has CDR1 domain comprising the amino acid sequence of SEQ ID NO: 7 (i.e., the adalimumab VL CDR1) and the HCVR has a CDR1 domain comprising the amino acid sequence of SEQ ID NO: 8 (i.e., the adalimumab VH CDR1). The framework regions for VL preferably are from the $V_\kappa I$ human germline family, more preferably from the A20 human germline Vk gene and most preferably from the D2E7 VL framework sequences shown in FIGS. 1A and 1B of U.S. Pat. No. 6,090,382. In one embodiment, the framework regions for VH are from the VH3 human germline family, from the DP-31 human germline VH gene, or from the adalimumab VH framework sequences shown in FIGS. 2A and 2B of U.S. Pat. No. 6,090,382.

In one embodiment, the anti-TNFα antibody, or antigen binding portion thereof, used in the methods and compositions of the invention comprises the six CDRs of adalimumab (i.e., SEQ ID NOs: 3 to 8).

Accordingly, in another embodiment, the antibody or antigen-binding portion thereof preferably contains a light chain variable region (LCVR) comprising the amino acid sequence of SEQ ID NO: 1 (i.e., the adalimumab VL) and a heavy chain variable region (HCVR) comprising the amino acid sequence of SEQ ID NO: 2 (i.e., the adalimumab VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In one embodiment, the anti-TNFα antibody, or antigen binding portion thereof, used in the methods and compositions of the invention comprises the variable light and/or heavy chain as described in SEQ ID NOs: 9 and 10, respectively.

Also included in the methods and compositions of the invention are antibodies that are bioequivalent to adalimumab. In one embodiment, the methods and compositions of the invention include an antibody that is a biosimilar antibody to adalimumab, also referred to as an "adalimumab biosimilar antibody". An adalimumab biosimilar antibody is highly similar to adalimumab notwithstanding minor differences in clinically inactive components, and for which there are no clinically meaningful differences between the adalimumab biosimilar antibody and adalimumab in terms of the safety, purity and potency. In another embodiment, the methods and compositions of the invention include an antibody that is an interchangeable antibody to adalimumab, also referred to as an "adalimumab interchangeable antibody". An adalimumab interchangeable antibody is an adalimumab biosimilar antibody (as defined above) that is also expected to produce the same clinical result as adalimumab in any given patient. Furthermore, with respect to an adalimumab interchangeable antibody, the risk in terms of safety or diminished efficacy in alternating or switching between the use of the adalimumab interchangeable antibody and adalimumab must not be greater than the risk of using adalimumab without such alteration or switch.

In one embodiment, the invention is directed to an antibody having a light and/or heavy chain variable region having an amino acid sequence which is 85%, 86%, 87%, 88%, 89%, 90%, 91%, 92%, 93%, 94%, 95%, 96%, 97%, 98%, or 99% identical to SEQ ID NO: 1 or SEQ ID NO: 2 (adalimumab light and heavy chain sequences, respectively). Preferably, the antibody is an IgG, such as an IgG1 or IgG4 antibody.

In still other embodiments, the invention includes uses of an isolated human antibody, or an antigen-binding portions thereof, containing adalimumab-related VL and VH CDR3 domains. For example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

The TNFα antibody used in the methods and compositions of the invention may be modified for improved treatment of hidradenitis suppurativa. In some embodiments, the TNFα antibody or antigen binding fragments thereof, is chemically modified to provide a desired effect. For example, PEGylation of antibodies and antibody fragments of the invention may be carried out by any of the PEGylation reactions known in the art, as described, for example, in the following references: *Focus on Growth Factors* 3:4-10 (1992); EP 0 154 316; and EP 0 401 384 (each of which is incorporated by reference herein in its entirety). Preferably, the PEGylation is carried out via an acylation reaction or an alkylation reaction with a reactive polyethylene glycol molecule (or an analogous reactive water-soluble polymer). A preferred water-soluble polymer for PEGylation of the antibodies and antibody fragments of the invention is polyethylene glycol (PEG). As used herein, "polyethylene glycol" is meant to encompass any of the forms of PEG that have been used to derivatize other proteins, such as mono (C1-C10) alkoxy- or aryloxy-polyethylene glycol.

Methods for preparing PEGylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

PEGylated antibodies and antibody fragments may generally be used to treat hidradenitis suppurativa by administration of the TNFα antibodies and antibody fragments described herein. Generally the PEGylated antibodies and antibody fragments have increased half-life, as compared to the nonpegylated antibodies and antibody fragments. The PEGylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion used in the methods of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, non-covalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, used in the methods and compositions of the invention, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express adalimumab (D2E7) or an adalimumab (D2E7)-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of Proteins of Immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H 3$ family of human germline VH genes is amplified by standard PCR. Most preferably, the DP-31 VH germline sequence is amplified. To obtain a DNA fragment encoding the light chain variable region of adalimumab, or a adalimumab-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods. The variable light and heavy chain nucleic acid sequences of adalimumab are described in SEQ ID NOs: 36 and 37, respectively.

Once the germline VH and VL fragments are obtained, these sequences can be mutated to encode the adalimumab or adalimumab-related amino acid sequences disclosed herein. The amino acid sequences encoded by the germline VH and VL DNA sequences are first compared to the adalimumab or adalimumab-related VH and VL amino acid sequences to identify amino acid residues in the adalimumab or adalimumab-related sequence that differ from germline. Then, the appropriate nucleotides of the germline DNA sequences are mutated such that the mutated germline sequence encodes the adalimumab or adalimumab-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Moreover, it should be noted that if the "germline" sequences obtained by PCR amplification encode amino acid differences in the framework regions from the true germline configuration (i.e., differences in the amplified sequence as compared to the true germline sequence, for example as a result of somatic mutation), it may be desirable to change these amino acid differences back to the true germline sequences (i.e., "backmutation" of framework residues to the germline configuration).

Once DNA fragments encoding adalimumab or adalimumab related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions used in the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the adalimumab or adalimumab-related light or heavy chain sequences, the expression vector may already carry antibody constant region sequences. For example, one approach to converting the adalimumab or adalimumab-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in DHFR-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by cross-linking an antibody of the invention to a second antibody by standard chemical cross-linking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of the foregoing, nucleic acid, vector and host cell compositions that can be used for recombinant expression of the antibodies and antibody portions used in the invention include nucleic acids, and vectors comprising said nucleic acids, comprising the human TNFα antibody adalimumab (D2E7). The nucleotide sequence encoding the adalimumab light chain variable region is shown in SEQ ID NO: 36. The CDR1 domain of the LCVR encompasses nucleotides 70-102, the CDR2 domain encompasses nucleotides 148-168 and the CDR3 domain encompasses nucleotides 265-291. The nucleotide sequence encoding the adalimumab heavy chain variable region is shown in SEQ ID NO: 37. The CDR1 domain of the HCVR encompasses nucleotides 91-105, the CDR2 domain encompasses nucleotides 148-198 and the CDR3 domain encompasses nucleotides 295-330. It will be appreciated by the skilled artisan that nucleotide sequences encoding D2E7-related antibodies, or portions thereof (e.g., a CDR domain, such as a CDR3 domain), can be derived from the nucleotide sequences encoding the adalimumab LCVR and HCVR using the genetic code and standard molecular biology techniques.

Recombinant human antibodies of the invention in addition to adalimumab or an antigen binding portion thereof, or adalimumab-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-65; Huse et al. (1989)

Science 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy & light chain sequences having similar binding activity toward hTNFα, using the epitope imprinting methods described in Hoogenboom et al., WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be re-screened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human neutralizing antibodies with high affinity and a low off rate constant for hTNFα are described in U.S. Pat. Nos. 6,090,382, 6,258,562, and 6,509,015, each of which is incorporated by reference herein.

Antibodies, antibody-portions, and other TNFα inhibitors for use in the methods of the invention, can be incorporated into pharmaceutical compositions suitable for administration to a subject. Typically, the pharmaceutical composition comprises an antibody, antibody portion, or other TNFα inhibitor, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, e.g., sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods and compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In one embodiment, the antibody or other TNFα inhibitor is administered by intravenous infusion or injection. In another embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, the invention includes pharmaceutical compositions comprising an effective TNFα inhibitor (e.g., an anti-TNFα antibody, or an antigen-binding portion thereof) and a pharmaceutically acceptable carrier, wherein the effective TNFα inhibitor (e.g., an anti-TNFα antibody, or an antigen-binding portion thereof) may be used to treat hidradenitis suppurativa.

In one embodiment, the antibody or antibody portion for use in the methods of the invention is incorporated into a pharmaceutical formulation as described in PCT/IB03/04502 and U.S. Appln. No. 20040033228, incorporated by reference herein. This formulation includes a concentration 50 mg/ml of adalimumab, wherein one pre-filled syringe contains 40 mg of antibody for subcutaneous injection. Alternative low-ionic formulations of adalimumab are described in US20090291062, incorporated by reference herein.

The antibodies, antibody-portions, and other TNFα inhibitors of the present invention can be administered by a variety of methods known in the art, although for many therapeutic applications, the preferred route/mode of administration is parenteral, e.g., subcutaneous injection. In another embodiment, administration is via intravenous injection or infusion.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, Robinson, ed., Dekker, Inc., New York, 1978.

In one embodiment, the TNFα antibodies and inhibitors used in the invention are delivered to a subject subcutaneously. In one embodiment, the subject administers the TNFα inhibitor, including, but not limited to, a TNFα antibody, or antigen-binding portion thereof, to himself/herself. The TNFα antibodies and inhibitors used in the invention may also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. Appln. No. 20040033228, incorporated by reference herein, are used to treat rheumatoid arthritis using the treatment methods of the invention.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion for use in the methods of the invention is co-formulated with and/or co-administered with one or more additional therapeutic agents, including an hidradenitis suppurativa inhibitor or antagonist. For example, an anti-hTNFα antibody or antibody portion of the invention may be co-formulated and/or co-administered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Additional description regarding methods and uses of the invention comprising administration of a TNFα inhibitor are described in Part III of this specification.

The invention also pertains to packaged pharmaceutical compositions or kits for administering the anti-TNF antibodies of the invention for the treatment of hidradenitis suppurativa. In one embodiment of the invention, the kit comprises a TNFα inhibitor, such as an antibody, and instructions for administration of the TNFα inhibitor for treatment of hidradenitis suppurativa. The instructions may describe how, e.g., subcutaneously, and when, e.g., at week 0, week 2, week 4, etc., the different doses of TNFα inhibitor (e.g., an anti-TNFα antibody, or an antigen-binding portion thereof) shall be administered to a subject for treatment.

Another aspect of the invention pertains to kits containing a pharmaceutical composition comprising a TNFα inhibitor, such as an antibody, and a pharmaceutically acceptable carrier and one or more pharmaceutical compositions each comprising an additional therapeutic agent useful for treating hidradenitis suppurativa, and a pharmaceutically acceptable carrier. Alternatively, the kit comprises a single pharmaceutical composition comprising an anti-TNFα antibody, one or more drugs useful for treating hidradenitis suppurativa, and a pharmaceutically acceptable carrier. The instructions may describe how, e.g., subcutaneously, and when, e.g., at week 0, week 2, week 4, etc., the different doses of TNFα inhibitor (e.g., an anti-TNFα antibody, or an antigen-binding portion thereof) and/or the additional therapeutic agent shall be administered to a subject for treatment.

The kit may contain instructions for dosing of the pharmaceutical compositions for the treatment of hidradenitis suppurativa. Additional description regarding articles of manufacture of the invention are described in subsection III.

The package or kit alternatively can contain the TNFα inhibitor (e.g., an anti-TNFα antibody, or an antigen-binding portion thereof) and it can be promoted for use, either within the package or through accompanying information, for the uses or treatment of the disorders described herein. The packaged pharmaceuticals or kits further can include a second agent (as described herein) packaged with or co-promoted with instructions for using the second agent with a first agent (as described herein).

III. Uses and Compositions for Treating Hidradenitis Suppurativa with a TNFα Inhibitor Hidradenitis suppurativa (HS) is a skin disorder of the apocrine glands (sweat glands found on certain parts of the body) and hair follicles in which swollen, painful, inflamed lesions or lumps develop in the groin and sometimes under the arms and under the breasts. Hidradenitis suppurativa occurs when apocrine gland outlets become blocked by perspiration or are unable to drain normally because of incomplete gland development. Secretions trapped in the glands force perspiration and bacteria into surrounding tissue, causing subcutaneous induration, inflammation, and infection. Hidradenitis suppurativa is confined to areas of the body that contain apocrine glands. These areas are the axillae, areola of the nipple, groin, perineum, circumanal, and periumbilical regions.

TNFα is an important cytokine in the pathogenesis of hidradenitis suppurativa, with elevated concentrations of TNFα playing a role in the hidradenitis suppurativa pathologic condition. The methods and uses described herein provide a means of determining the efficacy of a TNFα inhibitor for treating hidradenitis suppurativa, and the use of such TNFα inhibitor for treating hidradenitis suppurativa. Thus in one embodiment, the invention provides a method for treating hidradenitis suppurativa in a subject having hidradenitis suppurativa.

Certain subtypes of hidradenitis suppurativa may be treated in accordance with the invention. In one embodiment, moderate to severe hidradenitis suppurativa, is treated by administering a TNFα inhibitor, e.g., antibody, or antigen-binding portion thereof, to a subject suffering therefrom. In one embodiment, chronic HS, e.g., moderate to severe chronic HS, is treated by administering a TNFα inhibitor, e.g., antibody, or antigen-binding portion thereof, to a subject suffering therefrom.

The invention also provides a method for treating certain subpopulations of hidradenitis suppurativa patients who may be especially difficult to treat (described in more detail below). For example, in one embodiment, the invention provides a method for treating patients who have a subtherapeutic response to a therapy, such as those who have been unresponsive or intolerant to oral antibiotics for treatment for their hidradenitis suppurativa.

The invention also provides methods for improving hidradenitis suppurativa symptoms in a subject based on indices used to measure the disease state.

Treatment of HS using a TNFα inhibitor, such as a human anti-TNFα antibody or antigen binding portion thereof, may also be determined using measures known in the art.

Treatment of HS may be determined using any of the measures described herein, e.g., improvement in Hurley Staging or the Sartorius scale, or any measure known to those in the art.

For example, in one embodiment, an improvement in the Hurley stage of the subject having HS, or any of the measures described herein, is evidence of effective HS treatment. In one embodiment, the severity of HS is determined according to the Hurley staging system. Hurley staging is based on assigning the subject having HS one of three different "Stages" depending on the disease level. More specifically, Stage I refers to abscess formation, single or multiple, without sinus tracts and cicatrisation; Stage II refers to recurrent abscesses with tract formation and cicatrisation, as well as single or multiple, widely separated lesions; and Stage III, which refers to diffuse or near-diffuse involvement, or multiple interconnected tracts and abscesses across the entire area. Hurley Stage III is the most severe form. In one embodiment, the subject having HS has HS lesions that are present in at least two distinct anatomic areas (e.g. left and right axilla; or left axilla and left inguinal-crural fold), one of which is at least Hurley Stage II. In another embodiment, the subject being treated has at least one lesion that is at least a Hurley Stage II.

In one embodiment, treatment of HS with a TNFα inhibitor, such as a human anti-TNFα antibody or antigen binding portion thereof, is determined by an improved Hurley score relative to a given baseline, e.g., the Hurley stage of the subject prior to treatment with the TNFα inhibitor. In one embodiment, improvement in a Hurley score indicates that the Hurley score of the subject has either improved or been maintained following treatment with a TNFα inhibitor, such as a human anti-TNFα antibody or antigen binding portion thereof. Severity of hidradenitis suppurativa may be determined according to standard clinical definitions. See, for example, Hurley staging {III vs. (I or II)} for hidradenitis suppurativa (Poli F, Jemec G B E, Revuz J., Clinical Presentation. In: Jemec G B E, Revuz J, Leyden J J, editors. Hidradenitis Suppurativa. Springer, New York, 2006, pp 11-24, incorporated herein by reference). Hurley stage III disease is the most severe stage of hidradenitis suppurativa, reflecting diffuse or near-diffuse involvement of affected areas.

In one embodiment, the Sartorius scale may be used as an index for measuring efficacy of a TNFa inhibitor, e.g., a human anti-TNFa antibody, for treating hidradenitis suppurativa. The Sartorius scale is described by Sartorius et al. in British Journal of Dermatology, 149: 211-213 (incorporated herein by reference). Briefly, the following outcome variables are explicitly mentioned in reports based on the Sartorius scale: (1) anatomical region involved (axilla, groin, gluteal or other region or inframammary region left and/or right: 3 points per region involved); (2) number and scores of lesions (abscesses, nodules, fistulas, scars: points per lesion of all regions involved: nodules 2; fistulas 4; scars 1; others 1); (3) the longest distance between two relevant lesions, i.e., nodules and fistulas, in each region, or size if only one lesion (<5 cm, 2; <10 cm, 4; >10 cm, 8); and (4) are all lesions clearly separated by normal skin? In each region (yes 0/no 6). By assigning numerical scores to these variables, disease intensity can be quantified in a more clinically meaningful way on an open-ended scale. A total score as well as scores of selected regions chosen for surgical or other intervention can be calculated and followed over time.

In one embodiment, treatment of HS with a TNFα inhibitor, such as a human anti-TNFα antibody or antigen binding portion thereof, is determined according to an achieving an HiSCR (Hidradenitis Suppurativa Clinical Response) of the subject being treated. The HisSCR is defined as at least a 50% reduction in the total inflammatory lesion (abscess and inflammatory nodule) count (AN count) in a subject relative to baseline, with no increase in abscess count and no increase in draining fistula count. In one embodiment, treatment of HS in a subject is defined as an at least 50% reduction in the inflammatory lesion (abscess and nodule) count.

The HiSCR scoring system was designed to assess hidradenitis suppurativa activity in an affected subject before and after a treatment. It is described in more detail in Example 5 below.

In another embodiment, treatment of HS with a TNFα inhibitor, such as a human anti-TNFα antibody or antigen binding portion thereof, is defined as achieving an Hidradenitis Suppurativa Physician's Global Assessment (HS-PGA) score, or HS-PGA score, as defined below, of clear (0), minimal (1), or mild (2), with an improvement (i.e., reduction) from baseline HS-PGA score of at least 2 grades, optionally, at the end of a treatment period (such as week 16). The baseline HS-PGA score is the HS-PGA score measured just prior to the commencement of treatment, to which the HS-PGA score obtained after a period of treatment is compared. Both the baseline HS-PGA score and the HS-PGA score obtained after a treatment period are assessed based on the following system and criteria:

| HS-PGA Scoring System | | |
| --- | --- | --- |
| Score | Rating | Description |
| 0 | Clear | No abscesses, no draining fistulas, no nodules |
| 1 | Minimal | No abscesses, no draining fistulas, no inflammatory nodules, presence of non-inflammatory nodules |
| 2 | Mild | No abscesses or draining fistulas, and less than 5 inflammatory nodules, or Single abscess or draining fistula, and no inflammatory nodules |
| 3 | Moderate | No abscesses or draining fistulas, and at least 5 inflammatory nodules, or Single abscess or draining fistula in the presence of inflammatory nodules, or Between 2 and 5 abscesses or draining fistulas with or without inflammatory nodules, up to 10 |
| 4 | Severe | Between 2 and 5 abscesses and draining fistulas with or without inflammatory nodules that are greater than 10 |
| 5 | Very severe | More than 5 abscesses or draining fistulas |

The HS-PGA scoring system was designed for use in assessing hidradenitis suppurativa activity before and after a treatment. It is a six-point score that partly depends on the presence/absence of abscesses, draining fistulas, and/or nodules (inflammatory or non-inflammatory), and, if present, the extent of such presence.

The invention also includes a method of decreasing an HS-PGA score of a subject comprising administering a human TNFα antibody, or antigen-binding portion thereof, to the subject, such that partial remission of hidradenitis suppurativa is induced. In one embodiment, the invention provides an improvement of at least about 2 grades in the HS-PGA score of a subject having hidradenitis suppurativa.

In one embodiment, the invention provides a method for improving the DLQI score of a subject. In one embodiment, the improvement in the DLQI score is determined by achieving a score, e.g., a statistically significant score, correlating with a "no" or "small impact" of the disease state on the subject. In one embodiment, the improvement in the DLQI score is determined by achieving an improvement in the DLQI score of the subject. Examples of such improvements are provided in the examples described herein.

Methods of treatment described herein may include administration of a TNFα inhibitor, e.g., antibody, or antigen-binding portion thereof, to a subject to achieve a therapeutic goal, e.g., treatment of hidradenitis suppurativa, or achievement of a clinical response as defined herein. Also included in the scope of the invention are uses of a TNFα inhibitor, e.g., antibody, or antigen-binding portion thereof, in the manufacture of a medicament to achieve a therapeutic goal, e.g., treatment, of hidradenitis suppurativa, increase in clinical response as defined herein, and/or maintenance or improvement (reduction) of a HiSCR. Thus, where methods are described herein, it is also intended to be part of this invention that the use of the TNFα inhibitor in the manufacture of a medicament for the purpose of the method is also considered within the scope of the invention. Likewise, where a use of a TNFα inhibitor, e.g., antibody, or antigen-binding portion thereof, in the manufacture of a medicament for the purpose of achieving a therapeutic goal is described, methods of treatment resulting in the therapeutic goal are also intended to be part of the invention.

In one embodiment, the invention provides a method for treating a subject having hidradenitis suppurativa (HS) comprising administering an isolated human anti-TNFα antibody, or an antigen binding portion thereof, to the subject according to a multiple variable dose regimen, such that HS is treated, wherein the multiple variable dose regimen comprises administering a first loading dose, administering a second loading dose which is less than the first loading dose, and administering a treatment dose which is less than the second loading dose, wherein the treatment dose is administered to the subject weekly.

In one embodiment, the invention provides a method for treating a subject having hidradenitis suppurativa (HS) comprising administering an isolated human anti-TNFα antibody, or an antigen binding portion thereof, to the subject according to a multiple variable dose regimen, such that HS is treated, wherein the multiple variable dose regimen comprises administering a first loading dose, administering a second loading dose which is less than the first loading dose, and administering a treatment dose which is less than the second loading dose, wherein the treatment dose is administered to the subject biweekly.

In one embodiment, the invention provides a method for decreasing the number of inflammatory lesions (AN count) in a subject having HS, said method comprising systemically administering an isolated human anti-TNFα antibody, or an antigen binding portion thereof, to the subject, such that the AN count is decreased. The decrease in AN count may be anything greater than 10%, e.g., the AN count may be reduced by at least a 50% reduction in the subject relative to baseline AN count. The subject may also exhibit other improvements in HS following treatment with a TNFα inhibitor, e.g., anti-TNFα antibody. For example the subject may have no increase in an abscess count and/or no increase in a draining fistula count following administration with the anti-TNFα antibody, or an antigen binding portion thereof.

In one embodiment, treatment of hidradenitis suppurativa is achieved by administering a human TNFα antibody, or an antigen-binding portion thereof, to a subject having hidradenitis suppurativa, wherein the human TNFα antibody, or an antigen-binding portion thereof, is administered on a weekly or biweekly dosing regimen, or any combination thereof. Biweekly dosing regimens can be used to treat disorders in which TNFα activity is detrimental, and are further described in U.S. application Ser. No. 10/163,657 (US 20030235585), incorporated by reference herein. In one embodiment, biweekly dosing includes a dosing regimen wherein doses of a TNFα inhibitor are administered to a subject every other week, e.g., beginning at week 1. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks or more, etc. Biweekly or weekly dosing is preferably administered parenterally, including subcutaneously. In one embodiment, the human TNFα antibody, or an antigen-binding portion thereof, is administered in a dose of about 40 mg for each weekly or biweekly dosing. In one embodiment, the human TNFα antibody, or an antigen-binding portion thereof, is adalimumab. Additional examples of dosing regimens within the scope of the invention are provided herein in the Examples.

In one embodiment, treatment of hidradenitis suppurativa is achieved using multiple variable dosing methods of treatment. Examples of such multiple variable dosing regimens are described in PCT appln. no. PCT/US05/12007, incorporated by reference herein. For example, a loading dose of about 160 and/or 80 mg of a TNFα inhibitor, e.g., TNFα antibody, or an antigen-binding portion thereof, may first be administered to a subject having hidradenitis suppurativa, followed by a maintenance or treatment dose of about 40 mg.

In one embodiment, the invention provides a method of treating hidradenitis suppurativa in a subject comprising administering a loading dose(s) of a TNFα inhibitor, e.g., TNFα antibody, or an antigen-binding portion thereof, to the subject at week 0, optionally another loading dose at week 2. In one embodiment, the loading dose(s) is given in its entirety on one day or is divided over multiple days (e.g., divided over two days). In one embodiment, the loading dose(s) is administered subcutaneously. Following administration of the loading dose(s), one or more maintenance or treatment dose(s) of the TNFα inhibitor, e.g., TNFα antibody, or an antigen-binding portion thereof, may be administered to the subject, wherein the maintenance or treatment dose is about half or ¼ of the dose amount of the loading dose(s). In one embodiment, the maintenance or treatment dose is administered to the subject about one or two weeks after the last loading dose(s). In one embodiment, the maintenance or treatment dose is administered subcutaneously. Subsequent doses may be administered following the same or different maintenance or treatment dosing regimen.

In one embodiment, two loading doses are administered to the subject. In one embodiment, the second loading dose is about 40-60% of the first or initial loading dose. In one embodiment, the treatment dose is about 40-60% of the second loading dose.

In one embodiment, the first loading dose is about 140-180 mg. Numbers intermediate to the stated range are also included in the invention, e.g., 145-175 mg, 150-170 mg, and 155-165 mg. In one embodiment, the first loading dose is about 160 mg.

In one embodiment, the second loading dose is about 60-100 mg. Numbers intermediate to the stated range are also included in the invention, e.g., 70-90 mg, 75-85 mg, and 65-95 mg. In one embodiment, the second loading dose is about 80 mg.

In one embodiment, the treatment dose is about 30-50 mg. Numbers intermediate to the stated range are also included in the invention, e.g., 35-45 mg. In one embodiment, the treatment dose is about 40 mg.

In another embodiment, the loading dose(s) of the human TNFα antibody, or antigen-binding portion thereof, comprises about 80 mg, and may be given at week 0, followed by at least one maintenance dose of the human TNFα antibody, or antigen-binding portion thereof, comprising about 40 mg, administered on a biweekly dosing regimen, optionally from week 1. Alternatively, in another embodiment, the loading dose(s) of the human TNFα antibody, or antigen-binding portion thereof, comprises a first dose of about 160 mg administered on week 0, and a second loading dose of about 80 mg administered on week 2, followed by at least one maintenance dose of the human TNFα antibody, or antigen-binding portion thereof, comprising about 40 mg, administered weekly thereafter. In one embodiment, the maintenance dose is administered to the subject starting at about week 4 (wherein week 0 is the initial loading dose).

In one embodiment, the subject is first selected for having HS and is then administered a TNFα inhibitor, e.g., TNFα antibody, or an antigen-binding portion thereof, in accordance with the methods described herein.

Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. Such dosage unit forms may be a tablet or pill with a pre-determined amount of therapeutic agents, or a vial with therapeutic agents to be reconstituted by a solution to produce a drug product of a pre-determined final concentration. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Dosage regimens described herein may be adjusted (e.g., in individual patients) to provide the optimum desired response, e.g., maintaining remission of hidradenitis suppurativa, in consideration of the teachings herein.

It is to be noted that dosage values can vary with the type and severity of hidradenitis suppurativa. It is to be further understood that for any particular subject, specific dosage regimens may be adjusted over time according to the teachings of the specification and the individual need and the professional judgment of the person administering or supervising the administration of the compositions, and that dosage amounts and ranges set forth herein are exemplary only and are not intended to limit the scope or practice of the claimed invention.

Subpopulations

The invention provides uses and methods for treating certain subpopulations of hidradenitis suppurativa patients with a TNFα inhibitor, e.g., TNFα antibody, or an antigen-binding portion thereof.

In one embodiment, the subject has HS lesions in at least two distinct anatomic areas prior to treatment.

In one embodiment, the subject had an inadequate response to or was intolerant to oral antibiotics for treatment of their HS.

In one embodiment, the subject has an AN count of greater than or equal to 3 at baseline, a female, a subject who is over 40 years old, a subject who is a smoker, or any combination thereof.

In one embodiment, the invention provides a method of treating moderate to severe hidradenitis suppurativa in a subject comprising administering to the subject a TNFα inhibitor, e.g., TNFα antibody, or an antigen-binding portion thereof, such that moderate to severe hidradenitis suppurativa is treated. Subjects having moderate to severe hidradenitis suppurativa may be administered a TNFα inhibitor, e.g., TNFα antibody, or an antigen-binding portion thereof, such that moderate to severe hidradenitis suppurativa is treated and advancement of the disease is prevented. The invention also provides use of a TNFα inhibitor, e.g., TNFα antibody, or an antigen-binding portion thereof, in the manufacture of a medicament for the treatment of moderate to severe hidradenitis suppurativa in a subject who has moderate to severe hidradenitis suppurativa. In one embodiment, a patient having moderate to severe hidradenitis suppurativa is defined as a patient having a HS-PGA score no less than 3. In one embodiment, such patients have been unresponsive or intolerant to oral antibiotics for treatment for their hidradenitis suppurativa. In one embodiment, such patients have had a diagnosis of moderate to severe hidradenitis suppurativa for at least 6 months prior to Baseline HS-PGA measurement, and involve at least two distinct anatomic areas (e.g. left and right axilla; or left axilla and left inguinal-crural fold).

In one embodiment, the invention provides an article of manufacture comprising adalimumab and a package insert, wherein the package insert indicates that adalimumab may be used to treat hidradenitis suppurativa in patients who have a HS-PGA score no less than 3, who have been unresponsive or intolerant to oral antibiotics for treatment for their hidradenitis suppurativa, and/or who have had a diagnosis of moderate to severe hidradenitis suppurativa for at least 6 months prior to Baseline HS-PGA measurement, and involve at least two distinct anatomic areas (e.g. left and right axilla; or left axilla and left inguinal-crural fold).

Articles of Manufacture

The invention also provides a packaged pharmaceutical composition wherein the TNFα inhibitor, e.g., human TNFα antibody, is packaged within a kit or an article of manufacture. The kit or article of manufacture of the invention contains materials useful for the treatment, including induction and/or remission, prevention and/or diagnosis of hidradenitis suppurativa. The kit or article of manufacture comprises a container and a label or package insert or printed material on or associated with the container which provides information regarding use of the TNFα inhibitor, e.g., a TNFα antibody, for the treatment of hidradenitis suppurativa.

A kit or an article of manufacture refers to a packaged product comprising components with which to administer a TNFα inhibitor for treatment of a hidradenitis suppurativa. The kit preferably comprises a box or container that holds the components of the kit. The box or container is affixed with a label or a Food and Drug Administration approved label, including a protocol for administering the TNFα inhibitor. The box or container holds components of the invention which are preferably contained within plastic, polyethylene, polypropylene, ethylene, or propylene vessels. The vessels can be capped-tubes or bottles. The kit can also include instructions for administering the TNFα antibody of the invention. In one embodiment the kit of the invention includes the formulation comprising the human antibody adalimumab (or D2E7), as described in PCT/IB03/04502 and U.S. application Ser. No. 10/222,140, incorporated by reference herein.

The term "package insert" is used to refer to instructions customarily included in commercial packages of therapeutic products, that contain information about the indications, usage, dosage, administration, contraindications and/or warnings concerning the use of such therapeutic products.

In one embodiment, the article of manufacture of the invention comprises (a) a first container with a composition contained therein, wherein the composition comprises a TNFα antibody; and (b) a package insert indicating that the TNFα antibody may be used for reducing signs and symptoms and inducing and maintaining remission of hidradenitis suppurativa. In a preferred embodiment, the label or package insert indicates that the TNFα inhibitor, e.g., a TNFα antibody, is used for treating hidradenitis suppurativa.

In one embodiment, the invention features a kit comprising a sufficient number of containers to provide both loading and treatment doses of the TNFa inhibitor, e.g., anti-TNFa antibody. For example, the kit may contain at least seven containers containing about 40 mg of an isolated human anti-TNFa antibody, or an antigen binding portion thereof. Seven containers each containing 40 mg of an anti-TNFa antibody could, for example, provide enough antibody for a loading dose of about 160 mg (4×40 mg), a loading dose of about 80 mg (2×40 mg), and one treatment dose of about 40 mg.

Suitable containers for the TNFα inhibitor, e.g., a TNFα antibody, include, for example, bottles, vials, syringes, including preloaded syringes, pens, including autoinjector pens, etc. The containers may be formed from a variety of materials such as glass or plastic. The container holds a composition which is by itself or when combined with another composition effective for treating, preventing and/or diagnosing the condition and may have a sterile access port.

In one embodiment, the article of manufacture comprises a TNFα inhibitor, e.g., a human TNFα antibody, and a label or package insert which indicates to a subject who will be administering the TNFα inhibitor about using the TNFα inhibitor for the treatment of hidradenitis suppurativa. The label may be anywhere within or on the article of manufacture. In one embodiment, the article of manufacture comprises a container, such as a box, which comprises the TNFα inhibitor and a package insert or label providing information pertaining to use of the TNFα inhibitor for the treatment of hidradenitis suppurativa. In another embodiment, the information is printed on a label which is on the outside of the article of manufacture, in a position which is visible to prospective purchasers.

In one embodiment, the label or package insert of the invention informs a reader, including a subject, e.g., a purchaser, who will be administering the TNFα inhibitor for treatment, that the TNFα inhibitor, e.g., a TNFα antibody such as adalimumab, is an indicated treatment of hidradenitis suppurativa, including of moderately to severely active disease in adult patients.

In one embodiment, the label or package insert describes certain patient populations who may respond favorably to the TNFα inhibitor within the article of manufacture. For example, the label or package insert may indicate that the TNFα antibody, e.g., adalimumab, may be used to treat hidradenitis suppurativa in patients who have been unresponsive or intolerant to oral antibiotics for treatment for their hidradenitis suppurativa.

In one embodiment, the label or package insert of the invention describes certain therapeutic benefits of the TNFα antibody, e.g., adalimumab, including specific symptoms of hidradenitis suppurativa which may be reduced by using the TNFα antibody, e.g., adalimumab. It should be noted that the package insert may also contain information pertaining to other disorders which are treatable using the TNFα antibody, e.g., adalimumab. Information described herein which is provided in a label or package insert and pertains to other disorders, i.e., diseases other than hidradenitis suppurativa, is also included within the scope of the invention. The package insert of the invention may indicate that extra TNFα in the body can attack normal healthy body tissues and cause inflammation especially in the tissues in your bones, cartilage, joints and digestive tract. The package insert of the invention may also indicate that adalimumab helps reduce the signs and symptoms of immune diseases, including rheumatoid and psoriatic arthritis (pain and swollen joints), ankylosing spondylitis (morning stiffness and back pain), and psoriasis (abdominal pain and diarrhea).

In another embodiment, the package insert of the invention describes the dose and administration of adalimumab, for the treatment of hidradenitis suppurativa. The label may indicate that the initiation of therapy includes a loading dose of about 160 mg and 80 mg administered at weeks 0 and 2, respectively. The label may also indicate that the maintenance dosing for the treatment of hidradenitis suppurativa with adalimumab is about 40 mg every week thereafter, such as starting from week 4. Alternatively, the label may indicate that the initiation of therapy includes a loading dose of about 80 mg administered at week 0, followed by maintenance doses of about 40 mg every other week thereafter, such as starting from week 1. Regardless of the initial treatment dosing regimen, the label may also indicate that additional maintenance doses are administered at about 40 mg every other week. In another embodiment, the label or package insert of the invention indicates that the TNFa inhibitor (e.g., adalimumab) is administered by subcutaneous injection.

The label or the package insert of the invention may also provide information to subjects who will be receiving adalimumab regarding combination uses with other hidradenitis suppurativa therapeutic agents for both safety and efficacy purposes.

The label or the package insert of the invention may contain warnings and precautions regarding the use of the TNFa inhibitor, e.g., a TNFa antibody such as adalimumab. In one embodiment, the information provided in the label or the package insert describes super infection of hidradenitis suppurativa lesions and/or pilonidal cyst flare.

The label or the package insert of the invention may contain information regarding the use of the TNFα inhibitor, e.g., a TNFα antibody such as adalimumab, in clinical studies for hidradenitis suppurativa. In one embodiment, the label of the invention describes the studies described herein as Examples 1 to 2, either as a whole or in portion. The label of the invention may also indicate that the safety profile for patients with hidradenitis suppurativa treated with HUMIRA® was similar to the safety profile seen in patients with other indications treatable by HUMIRA®, such as rheumatoid arthritis.

The label of the invention may contain information regarding the pharmacodynamics of the TNFα inhibitor, e.g., a TNFα antibody such as adalimumab.

In one embodiment of the invention, the kit comprises a TNFα inhibitor, such as an antibody, an second pharmaceutical composition comprising an additional therapeutic agent, and instructions for administration of both agents for the treatment of hidradenitis suppurativa. The instructions may describe how, e.g., subcutaneously, and when, e.g., at week 0, week 2, and weekly or biweekly thereafter, doses of TNFα antibody and/or the additional therapeutic agent shall be administered to a subject for treatment.

Another aspect of the invention pertains to kits containing a pharmaceutical composition comprising an anti-TNFα antibody and a pharmaceutically acceptable carrier and one or more additional pharmaceutical compositions each comprising a drug useful for treating a TNFα related disorder (such as hidradenitis suppurativa) and a pharmaceutically acceptable carrier. Alternatively, the kit comprises a single pharmaceutical composition comprising an anti-TNFα antibody, one or more drugs useful for treating a TNFα related disorder (such as hidradenitis suppurativa) and a pharmaceutically acceptable carrier. The kits further contain instructions for dosing of the pharmaceutical compositions for the treatment of a TNFα related disorder (such as hidadenitis suppurativa).

The package or kit alternatively may contain the TNFα inhibitor and it may be promoted for use, either within the package or through accompanying information, for the uses or treatment of hidradenitis suppurativa. The packaged pharmaceuticals or kits further can include a second agent (as described herein) packaged with or co-promoted with instructions for using the second agent with a first agent (as described herein).

Additional Therapeutic Agents

TNFα inhibitors, including TNFα antibodies, or antigen binding portions thereof, may be used in the methods, uses, and compositions of the invention either alone or in combination with an additional therapeutic agent. It should be understood that the TNFα inhibitors can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the TNFα inhibitors. The additional agent also can be an agent that imparts a beneficial attribute to the therapeutic composition, e.g., an agent which effects the viscosity of the composition.

It should further be understood that the combinations which are to be included within this invention are those combinations useful for their intended purpose. The agents set forth below are illustrative for purposes and not intended to be limited. The combinations, which are part of this invention, can be the TNFα inhibitors of the present invention and at least one additional agent selected from the lists below. The combination can also include more than one additional agent, e.g., two or three additional agents if the combination is such that the formed composition can perform its intended function.

TNFα inhibitors described herein may be used in combination with additional therapeutic agents such as a Disease Modifying Anti-Rheumatic Drug (DMARD) or a Non-steroidal Anti-inflammatory Drug (NSAID) or a steroid or any combination thereof.

Preferred examples of a DARED are hydroxychloroquine, leflunomide, methotrexate, parenteral gold, oral gold and sulfasalazine. Preferred examples of non-steroidal anti-inflammatory drug(s) also referred to as NSAIDS include drugs like ibuprofen. Other preferred combinations are corticosteroids including prednisolone; the well known side effects of steroid use can be reduced or even eliminated by tapering the steroid dose required when treating patients in combination with TNFα inhibitors of this invention.

Preferred combinations of therapeutic agents may interfere at different points in the autoimmune and subsequent inflammatory cascade; preferred examples include TNF antagonists such as soluble p55 or p75 TNF receptors, derivatives, thereof, (p75 TNFRIgG (ENBREL™) or p55 TNFRIgG (Lenercept), chimeric, humanized or human TNF antibodies, or a fragment thereof, including infliximab (REMICADE®, Johnson and Johnson; described in U.S. Pat. No. 5,656,272, incorporated by reference herein), PSORIASIS P571 (a humanized monoclonal anti-TNF-alpha IgG4 antibody), PSORIASIS P 870 (a humanized monoclonal anti-TNF-alpha antibody fragment), an anti-TNF dAb (Peptech), SIMPONI®(golimumab; also referred to as CNTO 148; Centocor Ortho Biotech, see WO 02/12502), and adalimumab (HUMIRA®, Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498,237; 6,451,983; and 6,448,380, each of which is incorporated by reference herein. Other combinations including TNFα converting enzyme (TACE) inhibitors; IL-1 inhibitors (Interleukin-1-converting enzyme inhibitors, IL-IRA etc.) may be effective for the same reason. Other preferred combinations include Interleukin 11. Yet another preferred combination are other key players of the autoimmune response which may act parallel to, dependent on or in concert with TNFα inhibitors function; especially preferred are IL-18 antagonists including IL-18 antibodies or soluble IL-18 receptors, or IL-18 binding proteins. Yet another preferred combination are non-depleting anti-PSORIASIS 4 inhibitors. Yet other preferred combinations include antagonists of the co-stimulatory pathway PSORIASIS 80 (B7.1) or PSORIASIS 86 (B7.2) including antibodies, soluble receptors or antagonistic ligands.

The TNFα inhibitors used in the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g. IRAK, NIK, IKK, p38 or MAP kinase inhibitors), IL-1β converting enzyme inhibitors, TNFα converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75 TNFRIgG (Enbrel™ and p55 TNFRIgG (Lenercept)), sIL-1RI, sIL-1RII, sIL-6R), anti-inflammatory cytokines (e.g. IL-4, IL-10, IL-12, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, PSORIASIS C-801, and Mesopram.

Non-limiting examples of therapeutic agents for hidradenitis suppurativa with which TNFα inhibitor of the invention can be combined include the following: antiseptic and antiperspirant agents (e.g., 6.25% aluminum chloride hexahydrate in absolute ethanol), anti-inflammatory or anti-antiandrogen therapy such as tetracycline, intralesional triamcinolone, or finasteride.

The antibodies of the invention, or antigen binding portions thereof, may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors, TNFα converting enzyme inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and anti-inflammatory cytokines (e.g., IL-4, IL-10, IL-12, IL-13 and TGFβ).

Additional examples of therapeutic agents for hidradenitis suppurativa in which a TNFα inhibitor can be combined include the following: combinations of TNF antagonists, for example, anti-TNF antibodies, D2E7 (PCT Publication No. WO 97/29131; HUMIRA®), Ca2 (REMICADE®), PSORIASIS P 571, TNFR-Ig constructs, (p75 TNFRIgG (ENBREL™) and p55 TNFRIgG (LENERCEPT) inhibitors and PDE4 inhibitors. TNFα inhibitors of the invention can be combined with corticosteroids, for example, budenoside and dexamethasone. TNFα inhibitors of the invention may also be combined with agents such as sulfasalazine, 5-aminosalicylic acid and olsalazine, and agents which interfere with synthesis or action of proinflammatory cytokines such as IL-1, for example, IL-1β converting enzyme inhibitors and IL-1ra. TNFα inhibitors may also be used with T cell signaling inhibitors, for example, tyrosine kinase inhibitors 6-mercaptopurines. TNFα inhibitors can be combined with IL-12. TNFα inhibitors can be combined with mesalamine, prednisone, azathioprine, mercaptopurine, infliximab, methylprednisolone sodium succinate, diphenoxylate/atrop sulfate, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab and interferon-gamma.

The TNFα inhibitors may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists, and the humanized IL-6 antibody tocilizumab.

In yet another embodiment, the invention includes an article of manufacture or a method comprising the combination of a TNFα inhibitor and an antibiotic or anti-infective agent. Anti-infective agents include those agents known in the art to treat viral, fungal, parasitic or bacterial infections. The term, "antibiotic," as used herein, refers to a chemical substance that inhibits the growth of, or kills, microorganisms. Encompassed by this term are antibiotic produced by a microorganism, as well as synthetic antibiotics (e.g., analogs) known in the art. Antibiotics include, but are not limited to, clarithromycin (BIAXIN®), ciprofloxacin (CIPRO®), and metronidazole (FLAGYL®).

Any one of the above-mentioned therapeutic agents, alone or in combination therewith, can be administered to a subject suffering from hidradenitis suppurativa, in combination with the TNFα antibody using a multiple variable dose treatment regimen. In one embodiment, any one of the above-mentioned therapeutic agents, alone or in combination therewith, can be administered to a subject suffering from hidradenitis suppurativa in addition to a TNFα antibody to treat another TNFα-related disorder, such as rheumatoid arthritis. It should be understood that the additional therapeutic agents can be used in combination therapy as described above, but also may be used in other indications described herein wherein a beneficial effect is desired.

The combination of agents used within the methods and pharmaceutical compositions described herein may have a therapeutic additive or synergistic effect on the condition(s) or disease(s) targeted for treatment. The combination of agents used within the methods or pharmaceutical compositions described herein also may reduce a detrimental effect associated with at least one of the agents when administered alone or without the other agent(s) of the particular pharmaceutical composition. For example, the toxicity of side effects of one agent may be attenuated by another agent of the composition, thus allowing a higher dosage, improving patient compliance, and improving therapeutic outcome. The additive or synergistic effects, benefits, and advantages of the compositions apply to classes of therapeutic agents, either structural or functional classes, or to individual compounds themselves.

IV. Efficacy of TNFα Inhibitor

The invention also provides methods for determining whether a TNFα inhibitor (e.g., an anti-TNFα antibody, or an antigen-binding portion thereof) is effective at treating hidradenitis suppurativa in a subject. Such methods may be used to determine the efficacy of a TNFα inhibitor, including those which are unknown or unconfirmed to have such efficacy. Using the methods described herein, effective TNFα inhibitors (e.g., an anti-TNFα antibody, or an antigen-binding portion thereof) may be determined or confirmed and, subsequently, used in the method of treating hidradenitis suppurativa.

The efficacy of a TNFα inhibitor (e.g., an anti-TNFα antibody, or an antigen-binding portion thereof) for treatment of hidradenitis suppurativa in a patient or patient population who has hidradenitis suppurativa, may be evaluated by determining the percentage of the patient population in whom a clinical response has been achieved following administration of the TNFα inhibitor (e.g., a test or candidate TNFα inhibitor).

In one embodiment, the invention provides a method for determining the efficacy of a TNFα inhibitor, including a human TNFα antibody, for treating hidradenitis suppurativa in a subject, using the HS-PGA score to assess the proportion of treated subjects who have achieved clinical response defined above. Alternatively, or in addition, the HiSCR scoring system, the DLQI, the Sartorius scale may also be used to determine efficacy.

In certain embodiments, a candidate TNFα inhibitor (e.g., an anti-TNFα antibody, or an antigen-binding portion thereof) is efficacious for treating hidradenitis suppurativa if at least about 5, 6, 7, 8, 9, 10, 11, 12, 13, 14, 15, 16, 17, 18, 19, 20, 21, 22, 23, 24, 25% or more treated patients achieve statistically significant (as compared to placebo treatment) clinical response, as defined herein based on HS-PGA score. Ranges of values using a combination of any of the above recited values as upper and/or lower limits are intended to be included in the scope of the invention.

The DLQI is an additional validated instrument used to assess dermatologic-related functional limitations. Characteristics of the DLQI include: (1) ten items on an overall scoring range of 0-30; higher scores represent greater quality of life impairment and lower scores represent lower quality of life impairment; (2) well-established properties of reliability and validity for the DLQI total score in a dermatology setting (see Badia et al. (1999) *Br J Dermatol* 141:698; Finlay et al. (1994) *Clin Exp Dermatol* 19:210; and Shikiar et al. (2003) *Health and Quality of Life Outcomes* 1:53); (3) six subcategories: symptoms and feelings; daily activities; leisure; work/school; personal relationships; and treatment; and, (4) all data are observed values. Patients who discontinued before the time point were not included in this analysis.

Ranges of DLQI scores can be evaluated for their correspondence to categories of disease impact.

In certain embodiments, the DLQI score may also be used as an index for measuring efficacy of a TNFα inhibitor in a patient or patient population having hidradenitis suppurativa, where mean improvement within a population of treated patients in their DLQI scores that is statistically significant (as compared to placebo) indicates that the TNFa inhibitor (e.g., an anti-TNFα antibody, or an antigen-binding portion thereof) is effective for treating hidradenitis suppurativa. In one embodiment, the invention provides a method for determining whether a human TNFα antibody is effective for treating hidradenitis suppurativa.

In certain embodiments, the Pain VAS score may also be used as an index for measuring efficacy of a TNFα inhibitor (e.g., an anti-TNFα antibody, or an antigen-binding portion thereof) in a patient or patient population having hidradenitis suppurativa, where mean statistically significant (as compared to placebo) improvement within a population of treated patients in their Pain VAS scores that is at least 30% indicates that the TNFα inhibitor is effective for treating hidradenitis suppurativa. In one embodiment, the invention provides a method for determining whether a human TNFα antibody is effective for treating hidradenitis suppurativa based on improvement in Pain VAS score.

In one embodiment, the invention provides a method of treating hidradenitis suppurativa in a subject, comprising administering an effective amount of a TNFα inhibitor, e.g., a human TNFα antibody, to the subject such that hidradenitis suppurativa is treated, wherein the effective TNFα inhibitor, e.g., human TNFα antibody, is previously identified as achieving a statistically significant clinical response within a patient or patient population.

In one embodiment, at least about 5, 6, 7, 8, 9, 10, 11, 12, 13, 14, 15, 16, 17, 18, 19, 20, 21, 22, 23, 24, 25% or more of the treated patients achieve a clinical response as defined herein.

Time points for determining efficacy will be understood by those of skill in the art to depend on the type of efficacy being determined, e.g., treatment of hidradenitis suppurativa. In one embodiment, measurements in scores, e.g., the HS-PGA score of a subject, may be measured against a subject's baseline score. Generally, a baseline refers to a measurement or score of a patient before treatment, i.e. week 0. In certain embodiments, however, other time points may also be included as a starting point in determining efficacy.

Patients or patient populations described in the methods of the invention are generally selected based on common characteristics, such as, but not limited to, subjects diagnosed with hidradenitis suppurativa. Such a patient or patient population would be appropriate for determining the efficacy of the TNFα inhibitor (e.g., an anti-TNFα antibody, or an antigen-binding portion thereof) for treating hidradenitis suppurativa in the given patient population. In one embodiment, the patient or patient population is an adult population, e.g., older than 17 years of age or older than 18 years of age. In certain embodiments, the patient or patient population has a diagnosis of moderate to severe hidradenitis suppurativa for at least 6 months prior to baseline measurement of HS-PGA, and involved at least two distinct anatomic areas (e.g., left and right axilla; or left axilla and left inguinal-crural fold). In one embodiment, subjects have been unresponsive or intolerant to oral antibiotics for treatment for their hidradenitis suppurativa. In one embodiment, subjects have an HS-PGA score of 3 or greater.

In one embodiment, the methods of the invention is used to determine whether a TNFα inhibitor is an effective TNFα inhibitor (e.g., an anti-TNFα antibody, or an antigen-binding portion thereof) with respect to a patient population who has already been administered the TNFα inhibitor. Such a patient population may be pre-selected according to common characteristics, e.g., HS-PGA score, and may have already been given the TNFα inhibitor. Administration of the TNFα inhibitor (e.g., an anti-TNFα antibody, or an antigen-binding portion thereof) may or may not be performed by the same person of ordinary skill who is determining the efficacy of the TNFα inhibitor in accordance with the teachings of the specification.

In one embodiment, the methods of the invention comprise administering the TNFα inhibitor (e.g., an anti-TNFα antibody, or an antigen-binding portion thereof) to the subjects of a patient population and determining the efficacy of the TNFα inhibitor (e.g., an anti-TNFα antibody, or an antigen-binding portion thereof) by determining changes, improvements, measurements, etc., using HS-PGA scores of the patient population in comparison to the Examples set forth below.

In addition, while some methods are described in terms of patient populations, methods of efficacy described herein may also be applied to individual subjects. For example, a method for determining efficacy may comprise determining whether a subject who has hidradenitis suppurativa, and who is on a dosage regimen comprising a human TNFα antibody, is able to achieve a clinical response as defined herein, in order to determine if the human TNFα antibody is an effective human TNFα antibody. In one embodiment, if the subject is able to achieve a clinical response as defined herein for at least about 8, 12, 16, 20, 24, 30, 36, 42, 48, 52, 56 weeks or more, then the human TNFα antibody is effective at treating hidradenitis suppurativa.

The Examples and discoveries described herein are representative of a TNFα inhibitor, i.e., adalimumab, which is effective for treating hidradenitis suppurativa. As such, the studies and results described in the Examples section herein may be used as a guideline for determining the efficacy of a TNFα inhibitor, i.e., whether a TNFα inhibitor is an effective TNFα inhibitor for the treatment of hidradenitis suppurativa. In one embodiment, methods of determining efficacy described herein may be used to determine whether a TNFα inhibitor is bioequivalent to another TNFα inhibitor.

In one embodiment, the article of manufacture of the invention comprises instructions regarding how to determine the efficacy of the TNF inhibitor for the treatment of hidradenitis suppurativa.

The present invention is further illustrated by the following examples which should not be construed as limiting in any way.

EXAMPLES

Example 1

Safety and Efficacy of Adalimumab in Subjects with Moderate to Severe Chronic Hidradenitis Suppurativa (HS)

This example demonstrates that anti-TNFα antibodies, such as the fully human anti-TNFα antibody adalimumab, are efficacious and safe for treating human hidradenitis suppurativa (HS) patients, especially human patients with moderate to severe chronic hidradenitis suppurativa.

In this Phase II clinical trial study, qualified hidradenitis suppurativa patients were first randomized into three treatment groups in a 1:1:1 ratio: (1) weekly subcutaneous (s.c.) injections of about 40 mg adalimumab (40 mg qwk); (2) biweekly s.c. injection of about 40 mg adalimumab (40 mg eow); and (3) matching placebo with no adalimumab injection. More details regarding the three treatment arms are described below. Randomization was stratified by Hurley staging (III vs. I or II) for HS.

This period of the study (Period 1) was conducted over 16 weeks, as a double-blind, placebo-controlled treatment period to evaluate efficacy and safety. Patients were then invited to participate in a 36-week open-label follow-up period (Period 2), in which all patients receive open-label adalimumab (40 mg eow) s.c. injection for an evaluation of long-term safety and efficacy (see Example 2 below). Patients who had received placebo in Period 1 received an initial blinded 80 mg dose of adalimumab at Week 16, and patients who had received active therapy in Period 1 received blinded placebo at Week 16. Patients with HS-PGA scores ≥3 (moderate or worse) at Weeks 28 or 31 also had the option to dose escalate to 40 mg adalimumab weekly. Those whose dose escalated remained on ew dosing for the remainder of the study.

Study Treatment Arms

Arm A (Adalimumab 40 mg ew): subjects randomized to Arm A received a loading dose of adalimumab 160 mg at Week 0 and adalimumab 80 mg at Week 2, followed by adalimumab 40 mg weekly starting at Week 4 through Week 15. Arm B (Adalimumab 40 mg eow): subjects randomized to Arm B received a loading dose of adalimumab 80 mg at Week 0, followed by adalimumab 40 mg eow starting at Week 1 through Week 15.

Arm C (Placebo): subjects randomized to Arm C received matching placebo administered weekly, starting at Week 0 through Week 15.

In the event that a patient had an acutely painful lesion, investigators had the option to intervene with either an injection of intralesional triamcinolone acetonide suspension or performance of incision and drainage. Two protocol-allowed interventions were permitted during Period 1. Patients requiring more than two interventions during Period 1 were to be discontinued from the study.

Population

Qualified subjects were males and females ≥18 years old, had a diagnosis of moderate to severe hidradenitis suppurativa (HS-PGA score of moderate or worse; see Table 1 for HS-PGA Scoring System) for at least 6 months prior to Baseline that involved at least two distinct anatomic areas (e.g., left and right axilla; or left axilla and left inguinal-crural fold).

Subjects must have been unresponsive or intolerant to oral antibiotics for treatment for their hidradenitis suppurativa. In addition, qualified subjects were required to have a hidradenitis suppurativa-PGA score of 3 or greater. Patients who had prior treatment with any anti-TNF therapy, including adalimumab, infliximab or etanercept, were excluded from the study. Also excluded are patients who had used systemic non-biologic therapies (other than certain permitted oral antibiotics) for HS within 4 weeks prior to Baseline visit.

Use of the following oral and/or topical antibiotic therapy for HS was permitted if patients had received a stable dose for ≥4 weeks prior to Baseline visit and the dose remained stable during study: 1% topical clindamycin bid; Tetracycline (up to 500 mg po bid); Doxycycline (up to 100 mg po bid); or Minocycline (up to 100 mg po bid).

More specifically, patient inclusion criteria included adults with stable, moderate to severe hidradenitis suppurativa. Patients also had to have had a negative Chest X-ray and PPD test at Screening. If a participant had a past ulcerative reaction to PPD placement and/or chest X-ray consistent with prior tuberculosis exposure, the participant had to initiate, or have documented completion of, a course of anti-tuberculosis therapy. Participants had to have the ability to administer subcutaneous injections, and be in general good health otherwise.

Patient exclusion criteria included patients who had prior anti-TNF therapy and unstable antibiotic therapy for HS. The exclusion criteria also required medication washouts for other HS treatments. Patient exclusion criteria further included prior exposure to Tysabri® (natalizumab), recent infection requiring treatment, any significant medical events or conditions that may put patients at risk for participation, female subjects who were pregnant or breast-feeding or considering becoming pregnant during the study, a history of cancer, except successfully treated skin cancer, and any recent history of drug or alcohol abuse.

Participating sites were predominantly in the United States (Alabama, California, Florida, Georgia, Illinois, Indiana, Massachusetts, Missouri, Nebraska, New York, North Carolina, Pennsylvania, Texas, Virginia), with some sites located in the Netherlands, Denmark, and Germany.

One hundred ninety five patients were screened for entry in the study: 41 were screen failures, and 154 patients from 26 centers in four countries (Denmark, Germany, Netherlands, and the United States) were enrolled (FIG. 1). The most common reason for patients failing screening was not meeting screening criteria.

Efficacy Endpoint(s)

The assessed efficacy endpoints include: Hidradenitis Suppurativa Physician's Global Assessment (HS-PGA) response (scale below, definition of HS-PGA response described above); change in abscess, draining fistula, and inflammatory nodules; and QoL assessment, change in pain score. Specifically, at screening and study visits, physicians assessed counts of nodules (inflammatory and non-inflammatory), abscesses, and fistulas (draining and non-draining), and used these counts to assign patients to one of six ordinal categories (clear, minimal, mild, moderate, severe, very severe) of the HS-PGA scale according to Table 1 below.

TABLE 1

| HS-PGA Scoring System | | |
|---|---|---|
| Score | Rating | Description |
| 0 | Clear | No abscesses, no draining fistulas, no nodules |
| 1 | Minimal | No abscesses, no draining fistulas, no inflammatory nodules, presence of non-inflammatory nodules |
| 2 | Mild | No abscesses or draining fistulas, and less than 5 inflammatory nodules, or Single abscess or draining fistula, and no inflammatory nodules |
| 3 | Moderate | No abscesses or draining fistulas, and at least 5 inflammatory nodules, or Single abscess or draining fistula in the presence of inflammatory nodules, or Between 2 and 5 abscesses or draining fistulas with or without inflammatory nodules, up to 10 |
| 4 | Severe | Between 2 and 5 abscesses and draining fistulas with or without inflammatory nodules that are greater than 10 |
| 5 | Very severe | More than 5 abscesses or draining fistulas |

A clinical response to treatment was defined as an HS-PGA score of clear, minimal, or mild with at least a two-grade improvement relative to baseline score. Pain was assessed with a visual analogue score (VAS), ranging from 0 mm (no pain) to 100 mm (maximal pain). The following patient reported instruments were included in the study: the Dermatology Life Quality Index (DLQI) (measures dermatology-specific health-related quality of life ranging from 0-30 with 0 being no impairment), Work Productivity and Activity Impairment-Specific Health Problem: Psoriasis (WPAI-SHP) (ranges from 0-100 with 0 being no impairment), Patient Health Questionnaire (PHQ-9) (self-assessment for depression ranging 0-27 with 0 being no depressive symptoms). Blood samples were collected to measure levels of C-reactive protein (CRP) and other hematologic and biochemical markers and immunogenicity.

The primary endpoint of the study was the proportion of patients achieving clinical response at Week 16 (see Table 1 for HS-PGA Scale). Secondary efficacy measures included the proportion of patients achieving clinical response at Weeks 2, 4, 8, and 12, and all study visits during Period 2; the proportion of patients achieving at least a two-grade improvement in PGA scale at Week 16; the proportion of patients achieving a PGA score of clear, minimal or mild at Week 16; the proportion of patients achieving complete clearance of abscesses, draining fistulas, or inflammatory nodules at Week 16 and mean improvement in these counts from Baseline to Week 16; the proportion of patients achieving ≥30% reduction and 10 point absolute reduction in VAS score (among those patients with at least 10 mm VAS score at baseline); mean change in CRP levels from Baseline to Week 16; and, mean change in DLQI, total work productivity impairment (TWPI) outcome from the WPAI-SHP, and PHQ-9 scores from Baseline to Week 16.

More specifically, main secondary endpoints assessed included the following:

Percent Change From Baseline in Number of All Inflammatory Nodules and Plaques at Week 16. Specifically, the number of all inflammatory nodules and plaques includes inflammatory nodules that were tender, erythematous, and had diameters less than 5 cm and included plaques that had diameters greater than or equal to 5 cm. Range for percent change was negative infinity to infinity. Negative percent changes from Baseline indicated improvement;

Percentage of Participants Achieving Clinical Response at Week 2 from Baseline. Specifically, clinical response was defined as Hidradenitis Suppurativa-Physician's Global Assessment (HS-PGA) of clear, minimal, or mild (scores of 0, 1, or 2) with a minimum of 2 grades improvement (reduction)

from baseline. PGA is a physician's assessment of the severity of hidradenitis suppurativa based on a 6-point scale (score of 0=clear and 5=very severe);

Percentage of Participants Achieving Clinical Response at Week 4 from Baseline. Specifically, clinical response was defined as a Hidradenitis Suppurativa-Physician's Global Assessment (HS-PGA) score of clear, minimal, or mild (scores of 0, 1, or 2) with a minimum of 2 grades improvement (reduction) from baseline. PGA is a physician's assessment of the severity of hidradenitis suppurativa based on a 6-point scale (score of 0=clear and 5=very severe);

Percentage of Participants Achieving Clinical Response at Week 8 from Baseline. Specifically, clinical response was defined as a Hidradenitis Suppurativa-Physician's Global Assessment (HS-PGA) of clear, minimal, or mild (scores of 0, 1, or 2) with a minimum of 2 grades improvement (reduction) from baseline. HS-PGA is a physician's assessment of the severity of disease based on a 6-point scale (score of 0=clear and 5=very severe);

Percentage of Participants Achieving Clinical Response at Week 12 from Baseline. Specifically, clinical response was defined as a Hidradenitis Suppurativa-Physician's Global Assessment (HS-PGA) of clear, minimal, or mild (scores of 0, 1, or 2) with a minimum of 2 grades improvement (reduction) from baseline. HS-PGA is a physician's assessment of the severity of hidradenitis suppurativa based on a 6-point scale (score of 0=clear and 5=very severe);

Change From Baseline in Modified Sartorius Scale at Week 16. Specifically, the Modified Sartorius Scale reflects changes in hidradenitis suppurative symptoms, namely the number of lesions (abscesses, nodules, and fistulas) and the longest distance between lesions. A total score was derived based on assessments at up to 8 distinct anatomical regions and ranges from 5 to indefinite. Smaller numbers are better scores and indicate less lesion involvement, thus decreases (negative changes) from baseline indicate improvement in severity of disease;

Change From Baseline in Modified Sartorius Scale at Week 52. Specifically, the Modified Sartorius Scale reflects changes in hidradenitis suppurative symptoms, namely the number of lesions (abscesses, nodules, and fistulas) and the longest distance between lesions. A total score was derived based on assessments at up to 8 distinct anatomical regions and ranges from 5 to indefinite. Smaller numbers are better scores and indicate less lesion involvement, thus decreases (negative changes) from baseline indicate improvement in severity of disease;

Percent Change From Baseline in Number of All Inflammatory Nodules and Plaques at Week 52. Specifically, the number of all inflammatory nodules and plaques includes inflammatory nodules that were tender, erythematous, and had diameters less than 5 cm and included plaques that had diameters greater than or equal to 5 cm. Range for percent change was negative infinity to infinity. Negative percent changes from Baseline indicate improvement;

The proportion of patients achieving clinical success at Weeks 2, 4, 8, and 12;

The proportion of patients achieving an HS-PGA score of clear, minimal, or mild at Week 16; and The proportion of patients achieving ≥30% reduction and ≥10 point absolute reduction in VAS (Visual Analog Scale) (among patients with VAS pain score ≥10 at Baseline) at Weeks 2, 4, 8, 12, and 16.

Safety assessments included incidences of adverse events (AE) assessed throughout the study, and up to 70 days after last dose of study drug, or up to the date prior to the first dose in Period 2 for those who entered Period 2.

Statistical Methods

The study was planned to enroll 150 patients to have 80% power to detect a clinically relevant treatment difference, assuming a 10% clinical response rate for placebo-treated patients and a 35% response rate for adalimumab-treated patients.

Efficacy analyses were conducted on the intent-to-treat (ITT) populations in each period: for Period 1, the ITT population consisted of all patients randomized at Week 0; for Period 2, the integrated ITT population consisted of all patients randomized to adalimumab eow and adalimumab ew arms at Week 0, and patients randomized to the placebo arm at Week 0 who entered Period 2. Primary efficacy analysis was performed by Cochran-Mantel-Haenszel (CMH) test adjusting for baseline Hurley stage with non-responder imputation (NRI) as the primary approach and LOCF as sensitivity approach to impute missing data. To control for multiplicity, an initial overall test with all three treatment groups was performed and pair-wise comparison of each adalimumab dose group vs. placebo group were conducted only when the overall test was significant.

CMH and Analysis of Covariance (ANCOVA) with factors of treatment and Hurley stage were used for categorical and continuous secondary efficacy variables, respectively; NRI, last-observation-carried forward (LOCF), and as-observed approaches were used as appropriate. All statistical tests were two-sided with the significance level of 0.05.

All statistical tests were 2-sided with the significance level of 0.05. Pair-wise comparisons of adalimumab group vs. placebo group were conducted if overall comparison was significant.

The safety analyses were conducted in the safety population (patients in the ITT population receiving ≥1 dose of study drug); safety variables were summarized by treatment group.

Demographics and Clinical Characteristics

A total of 154 subjects were randomly assigned to one of the three treatment arms at Week 0: 51 to placebo (pbo), 52 to every other week (eow), and 51 to weekly (qw) therapy. Randomization was stratified by Hurley staging {III vs. (I or II)} for hidradenitis suppurativa (see Poli F, Jemec G B E, Revuz J., Clinical Presentation. In: Jemec G B E, Revuz J, Leyden J J, editors. Hidradenitis Suppurativa. Springer, New York, 2006, pp 11-24, incorporated herein by reference).

Hurley staging is a severity scale which assesses both current activity and past scarring, ranging from isolated abscesses in the primary stage to coalescing lesions with scarring and sinus tracts in the tertiary stage. Hurley stage III disease is the most severe stage of hidradenitis suppurativa, reflecting diffuse or near-diffuse involvement of affected areas. The percentage of enrolled subjects with Hurley stage III was not to exceed 50%.

TABLE 2

| Baseline Demographics and Clinical Characteristics | | | |
|---|---|---|---|
| | Placebo (n = 51) | ADA eow (n = 52) | ADA ew (n = 51) |
| Age (yrs), mean (SD) | 37.8 (12.10) | 36.1 (12.50) | 35.1 (10.69) |
| Female, n (%) | 36 (70.6) | 38 (73.1) | 36 (70.6) |
| White, n (%) | 37 (72.5) | 36 (69.2) | 37 (72.5) |
| Black | 8 (15.7) | 12 (23.1) | 9 (17.6) |

TABLE 2-continued

Baseline Demographics and Clinical Characteristics

|  | Placebo (n = 51) | ADA eow (n = 52) | ADA ew (n = 51) |
|---|---|---|---|
| Nicotine users, n (%) | 29 (56.9) | 26 (50.0) | 30 (58.8) |
| Body weight (kg), mean (SD) | 96.5 (24.80) | 99.8 (26.75) | 95.4 (22.94) |
| BMI, n (%) | | | |
| <25 | 9 (17.6) | 6 (11.5) | 9 (17.6) |
| ≥25-<30 | 6 (11.8) | 11 (21.2) | 12 (23.5) |
| ≥30 | 36 (70.6) | 35 (67.3) | 30 (58.8) |
| Disease duration (yrs), mean (SD) | 13.4 (10.4) | 10.9 (9.0) | 11.3 (9.1) |
| CRP (mg/L), mean (SD)[a] | 13.3 (15.0) | 17.8 (26.9) | 21.5 (33.1) |
| Hurley stage I or II, n (%) | 36 (70.6) | 37 (71.2) | 36 (70.6) |
| Hurley stage III, n (%) | 15 (29.4) | 15 (28.8) | 15 (29.4) |
| HS-PGA moderate, n (%) | 33 (64.7) | 35 (67.3) | 35 (68.6) |
| HS-PGA severe/very severe, n (%) | 17 (33.3) | 16 (30.8) | 16 (31.4) |
| Patients receiving p.o. doxycycline or minocycline, n (%) | 4 (7.8) | 6 (11.5) | 8 (15.7) |
| Prior topical therapy, n (%) | 27 (52.9) | 26 (50.0) | 23 (45.1) |
| Prior systemic therapy, n (%) | 49 (96.1) | 52 (100.0) | 50 (98.0) |
| Prior pain medication use, n (%) | 23 (45.1) | 17 (32.7) | 17 (33.3) |
| Prior opiod use, n (%) | 7 (13.7) | 7 (13.5) | 7 (13.7) |
| VAS skin pain, mean (SD) | 57.8 (28.51) | 53.0 (26.35) | 52.0 (24.51) |
| DLQI, mean (SD) | 15.4 (7.71) | 13.5 (7.65) | 16.4 (7.48) |
| PHQ-9, mean (SD) | 9.1 (6.8) | 8.1 (6.1) | 11.1 (7.0) |
| TWPI, mean (SD) | 31.4 (34.7) | 35.1 (29.5) | 45.5 (32.8) |
| HS-PGA Components | | | |
| Abscesses, median (IQR) | 1 (2.0) | 1 (2.0) | 1 (2.0) |
| Patients with abscess, n (%) | 29 (56.9) | 29 (55.8) | 20 (39.2) |
| Draining fistulas, mean (median) | 1 (3.0) | 1 (3.5) | 1 (3.0) |
| Patients with draining fistulas, n (%) | 33 (64.7) | 28 (53.8) | 30 (58.8) |
| Inflammatory nodules, mean (median) | 6 (10.0) | 7 (14.5) | 7 (10.0) |
| Patients with inflammatory nodules, n (%) | 49 (96.1) | 48 (92.3) | 50 (98.0) |

[a]Based on patients with non-missing values; placebo, n = 39; eow, n = 40; ew, n = 38.
ADA, adalimumab; BMI, body mass index; HS-PGA, Hidradenitis suppurativa physician's global assessment; VAS, visual analog scale; DLQI, dermatology life quality index; TWPI, total work productivity impairment; IQR, interquartile range.

It is apparent that baseline demographics were generally well-balanced across the treatment arms (see Table 2). The majority of all enrolled subjects were female (71.4%), white (71.4%), less than 40 years old (63.6% were less than 40 years old, with a mean age of 36.3 years), smokers (55.2%), and had a Hurley Stage II (55.2%). Mean weight for all enrolled subjects was 97.2 kg. Baseline characteristics were similar across treatment groups. Mean pain score was 54.3/100 and the percentages of patients with HS-PGA scores of moderate, severe, or very severe were 66.9%, 9.7%, and 22.1%, respectively (Table 3).

TABLE 3

Distribution of HS-PGA at Baseline (%)

| PGA Category | Placebo | Every Other Week | Weekly |
|---|---|---|---|
| Clear (0) | 0 | 0 | 0 |
| Minimal (1) | 2.0 | 0 | 0 |
| Mild (2) | 0 | 1.9 | 0 |
| Moderate (3) | 64.7 | 67.3 | 68.6 |
| Severe (4) | 9.8 | 9.6 | 9.8 |
| Very Severe (5) | 23.5 | 21.2 | 21.6 |

Mean DLQI scores at baseline indicated that HS had a large deleterious effect on patients' dermatology-specific quality of life. The mean baseline DLQI score of 15.1 was worse than the mean baseline DLQI score of 11.4 for patients enrolled in an adalimumab Phase III psoriasis trial (REVEAL, see Revicki et al., Dermatology 216: 260-270, 2008). Overall baseline demographics and clinical characteristics were similar across the three treatment arms.

Of the 154 subjects who enrolled, 11 discontinued during Period 1: 5 from the placebo group and 6 from the qw group. One of the discontinued subjects in the qw group withdrew for the primary reason of adverse event.

Overall, 90.2% of placebo patients, 100% of adalimumab (ADA) eow patients, and 88.2% of ADA ew patients completed Period 1. See Table 4 below. Of patients entering Period 2, 73.9% of placebo/eow patients, 74.5% of eow/eow patients, and 68.9% of ew/eow patients completed Period 2. Baseline demographics and clinical characteristics are summarized in Table 2. Of note, these patients were markedly obese, with average weights over 90 kg. Over 20% of the enrollees were African-American, suggesting that the epidemiology of the disease may be linked to the African-American population. They also had high entry levels of pain and substantial use of narcotics for this problem, with around 13% reporting opiod use. Prior systemic antibiotic usage for treatment of HS was reported by 144 patients (94%); of these, 104 (72%) reported no satisfactory response. Other systemic therapies that had been utilized included corticosteroids (29 patients, 19%) and retinoids (28 patients, 18%).

TABLE 4

Patient Disposition

|  | Placebo (n = 51) | ADA eow (n = 52) | ADA ew (n = 51) |
|---|---|---|---|
| Completed Period 1 | 46 (90.2%) | 52 (100%) | 45 (88.2%) |
| Primary reason for discontinuation | | | |
| Adverse event | 0 | 0 | 1 (2.0%) |
| Withdraw consent | 2 (3.9%) | 0 | 1 (2.0%) |

TABLE 4-continued

Patient Disposition

|  | Placebo (n = 51) | ADA eow (n = 52) | ADA ew (n = 51) |
|---|---|---|---|
| Lack of efficacy | 0 | 0 | 1 (2.0%) |
| Lost to follow-up | 2 (3.9%) | 0 | 1 (2.0%) |
| Exceeded protocol specified number of interventions[a] | 1 (2.0%) | 0 | 0 |
| other[b] | 0 | 0 | 2 (3.9%) |

[a]A maximum of 2 interventions were permitted during Period 1.
[b]One discontinued due to non-compliance and 1 per investigator discretion.

Efficacy Results

The primary endpoint for this study was the proportion of subjects achieving a clinical response, defined as achieving an HS-PGA of clear (0), minimal (1), or mild (2), with an improvement (i.e., reduction) from Baseline of at least 2 grades at Week 16.

All responders were in the Hurley Stage I/II stratum with the exception of one qw subject that was a responder in the Hurley Stage III stratum.

When evaluating the proportion of subjects in the eow arm and in the qw arm who improved at least two HS-PGA grades from Baseline to Week 16, both eow and qw treatment groups had response rates significantly higher than that of placebo: 3.9% for placebo subjects, 21.2% for eow subjects (p=0.009 vs. placebo), and 21.6% for qw subjects (p=0.008 vs. placebo).

Table 5 describes the proportion of patients achieving clinical response (defined as achieving an HS-PGA of clear, minimal, or mild, and at least 2 grade improvement relative to baseline) in each group. Specifically, a significantly greater proportion of patients allocated to the ew group achieved the primary endpoint, a clinical response at Week 16, compared with patients allocated to the placebo group (17.6% vs. 3.9%, p=0.03; FIGS. 1 and 7). For the primary endpoint, point estimates for number of patients needed to treat (NNT) were 18 for the eow group and 8 for the ew group. The clinical response rate at Week 16 with ew dosing was 22.2% (8/36) for patients with Hurley Stage I or II at baseline, compared with 6.7% (1/15) for patients with Hurley Stage III at baseline.

TABLE 5

Proportion (Percentage) of Patients Achieving Clinical Response

| Patient Group | Week 2 | Week 4 | Week 8 | Week 12 | Week 16 |
|---|---|---|---|---|---|
| Placebo | 2 | 2 | 7.8 | 5.9 | 3.9 |
| EOW | 9.6 | 5.8 | 5.8 | 7.7 | 9.6 |
| QWK | 2 | 11.8 | 7.8 | 21.6* | 17.6* |

*p = 0.005 at Week 12, or p = 0.006 at Week 16, qwk versus placebo.

Post-analysis also revealed that a higher proportion of current smokers receiving weekly therapy achieved a Clinical Response at Week 16 compared with current non-smokers receiving weekly therapy (23.3% vs. 9.5%). The percentage of subjects receiving concomitant oral antibiotics was too small to permit meaningful inferences about the effect of antibiotic usage on clinical response rates. Among patients receiving weekly therapy, a higher proportion of patients with BMI greater than or equal to the median BMI achieved a clinical response at Week 16 compared with patients below the median BMI (23% vs. 14%).

At Week 16, an HS-PGA score of clear, minimal, or mild was achieved by 49.0% of ew patients, 21.2% of eow patients, and 23.5% of placebo patients (p<0.01, ew vs. pbo).

Mean reduction (improvement) from baseline to Week 16 in the modified Sartorius scale was 33.0 for ew patients, 32.0 for eow patients, and 16.7 for placebo patients. Clinical photographs of the perineum of a patient receiving eow therapy showed marked improvement (data not shown).

Significant improvement was also seen when evaluating the proportion of subjects who improved at least one HS-PGA grade from Baseline to Week 16: 28.0% for placebo subjects, 40.4% for eow subjects, and 66.0% for ew subjects (p<0.001 vs. placebo). Upon further analysis, the proportion of subjects who improved at least one HS-PGA grade from Baseline to Week 16 is: 27.5% for placebo subjects, 40.4% for eow subjects, and 56.9% for ew subjects (p=0.002 vs. placebo).

Overall, at Week 16, a statistically significantly greater proportion of ADA ew patients (49.0%) achieved an HS-PGA of clear, minimal, or mild as compared with placebo patients (23.5%) (p<0.01, Table 6). This data also suggests that the tested adalimumab weekly dosing (ew) may be more effective in achieving an HS-PGA of clear, minimal or mild as compared to once-every-other week (eow or biweekly) dosing (21.2%) at Week 16.

TABLE 6

Proportion (Percentage) of Patients Achieving an HS-PGA of Clear, Minimal or mild at Week 16 of Treatment

| Patient Group | Week 16 |
|---|---|
| Placebo (n = 51) | 23.5 |
| EOW (n = 52) | 21.2 |
| EW (n = 51) | 49.0* |

*p < 0.01, placebo vs. ADA ew at Week 16

In fact, each of the individual components of the HS-PGA score improved at Week 16 for patients receiving ew therapy compared with placebo-treated patients; patients receiving eow therapy generally experienced less improvement than ew treated patients on each of these components (see below).

Adalimumab therapy, particularly ew dosing, was associated with significant improvement in various other patient-reported outcomes. Improvement in Pain VAS scores of ≥30% was considered to constitute a clinically relevant improvement in pain, and was thus a predefined secondary analysis. The proportion of subjects whose pain scores improved at least 30% from baseline to Week 16 was significantly higher than placebo in the qw arm only: 27.1% for placebo subjects, 36.2% for eow subjects, and 47.9% for qw subjects (p=0.037 vs. placebo). See Table 7.

Moreover, improvement in pain was rapid, with significantly more patients in both active treatment arms achieving at least 30% and at least 10 mm reduction in pain by Week 2. Specifically, by Week 2, 44.7% (p<0.01 vs. placebo) of subjects receiving adalimumab every other week (ADA eow) and 41.7% (p<0.05 vs. placebo) of subjects receiving adalimumab every week (ADA ew) experienced at least a 30% and at least a 10 mm reduction in pain when compared to placebo's 18.8%. By week 4, 58.3% (p<0.001 vs. placebo) of ADA ew subjects and 46.8% (p<0.05 vs. placebo) of ADA eow subjects showed a greater than 30% and greater than 10 mm reduction from baseline pain, compared to the 22.9% of the placebo group. At week 12, 60.4% (p<0.01 vs. placebo) of ADA ew subjects maintained statistically significant pain reduction over the placebo group (29.2%). See Table 7.

TABLE 7

Proportion (Percentage) of Patients Achieving a ≥30%
and ≥10 mm Reduction from Baseline in Pain
at Weeks 2, 4, 8, 12 and 16 of Treatment Among
Patients with ≥10 mm VAS Pain Score at Baseline

| Patient Group | Week 2 | Week 4 | Week 8 | Week 12 | Week 16 |
|---|---|---|---|---|---|
| Placebo (n = 48) | 18.8 | 22.9 | 29.2 | 29.2 | 27.1 |
| EOW (n = 47) | 44.7† | 46.8* | 40.4 | 42.6 | 36.2 |
| EW (n = 48) | 41.7** | 58.3§ | 43.8 | 60.4‡ | 47.9** |

*$p < 0.05$, ADA eow vs. placebo;
**$p < 0.05$, ADA ew vs. placebo;
†$p < 0.01$, ADA eow vs. placebo;
‡$p < 0.01$, ADA ew vs. placebo;
§$p < 0.001$, ADA ew vs. placebo Among patients with ≥10 mm VAS pain scores at baseline, the proportion with a clinically significant improvement in pain (at least 30% reduction and 10 mm reduction in pain) at Week 16 was significantly higher for patients in the ew group compared with the placebo group (47.9% vs. 27.1%, P<0.05); more than 40% of patients receiving ew or eow therapy crossed this threshold of pain reduction at Week 2.

Mean reduction (improvement) in DLQI scores was significantly greater for subjects in the qw arm only when compared to placebo: 1.9 for placebo subjects, 2.8 for eow subjects, and 6.0 for qw subjects (p<0.001 ew vs. placebo). Work productivity was significantly improved among patients in the ew group as compared with the placebo group: mean reduction (improvement) in TWPI scores between baseline and Week 16 were 17.4 for the ew group and 0.94 for the eow group; placebo patients experienced a 2.93 increase (deterioration) in TWPI score (p<0.001, ew vs. placebo). Mean reduction (improvement) in the PHQ-9 depression measure between baseline and Week 16 was 3.8 for the ew group, 1.4 for the eow group, and 1.2 for the placebo group (p<0.05, ew vs. placebo).

Raw counts of the abscesses, draining fistulas, and inflammatory nodules were the key clinical components of the PGA score. Table 8 below depicts the mean decrease in counts (positive value represents improvement) for these lesion types, from baseline to Week 16, for subjects in the three treatment arms:

TABLE 8

Mean Decrease in Counts for Abscesses, Draining
Fistulas and Inflammatory Nodules

| Patient Group | Abscesses | Draining Fistulas | Inflammatory Nodules |
|---|---|---|---|
| Placebo | 0.42 | −1.03 | 1.93 |
| EOW | 1.43 | 0.04 | 6.18* |
| QW | 1.85 | −4.93 | 5.66* |

*$p < 0.05$, qw vs. placebo

For inflammatory nodules, abscesses, and draining fistulas, Table 9 below provides the mean/median absolute change from baseline to Week 16, the mean/median percentage change from baseline to Week 16, and the proportion of patients achieving complete clearance at Week 16. The qwk dosing arm notably outperformed the eow dosing arm and placebo arm in mean/median percentage decrease in inflammatory nodules, mean/median percentage decrease in draining fistulas, and in the proportion of patients with complete clearance of draining fistulas. While the eow dosing arm outperformed the qwk dosing arm in mean absolute decrease in draining fistulas, the treatment effect for eow dosing relative to placebo was small with this endpoint (difference in mean change of less than 1 draining fistula per patient), and the mean increase in the qwk group was impacted by a single outlier.

TABLE 9

Percent Reduction, Absolute Reduction, Proportion of Patients with
Complete Clearance (%) Changes in Primary Lesions at Week 16

| | Placebo | Eow | Qwk |
|---|---|---|---|
| Percentage Reduction1 | | | |
| Inflammatory Nodules (mean) | 13.7 | 30.4 | 50.7 (p < 0.05 vs. placebo) |
| Inflammatory Nodules (median) | 17.86 | 48.39 | 66.67 |
| Abscesses (mean) | 25.0 | 46.2 | 51.8 |
| Abscesses (median) | 100.00 | 75.00 | 92.86 |
| Draining Fistulas (mean) | 7.5 | 7.7 | 44.4 (p < 0.05 vs. placebo) |
| Draining Fistulas (median) | 11.11 | 12.5 | 96.15 |
| Absolute Reduction1 | | | |
| Inflammatory Nodules (mean) | 1.93 | 6.18 (p < .01 vs. placebo) | 5.66 (p < 0.05 vs. placebo) |
| Inflammatory Nodules (median) | 1.0 | 3.5 | 4.0 |
| Abscesses (mean) | 0.42 | 1.43 | 1.85 |
| Abscesses (median) | 1.0 | 1.0 | 1.0 |
| Draining Fistulas (mean) | −1.03 | 0.04 | −4.93* |
| Draining Fistulas (median) | 1.0 | 0.5 | 1.5 |
| Proportion of patients with complete clearance1 (%) | | | |
| Inflammatory Nodules | 8.2 | 20.8 | 20.0 |
| Abscesses | 44.8 | 48.3 | 50.0 |
| Draining Fistulas | 27.3 | 25.0 | 43.3 |

1Among patients with any lesion at baseline. Positive value connotes patient improvement (reduction in counts).
*The mean increase in qwk group was heavily impacted by a single outlier: a patient for whom was reported an increase of 210 draining fistula (from 100 at baseline to 310 at Week 16), while the maximum increase in the other two groups was 14.

Table 10 below describes the proportion of patients achieving complete clearance of abscesses at Weeks 2, 4, 8, 12 and 16 among those with at least one lesion at baseline. The qwk dosing arm outperformed the eow dosing arm at every study visit except Week 2.

TABLE 10

Proportion (Percentage) of Patients Achieving Complete
Clearance of Abscesses at Weeks, 4, 8, 12 and 16

| Patient Group | Week 2 | Week 4 | Week 8 | Week 12 | Week 16 |
|---|---|---|---|---|---|
| Placebo | 37.9 | 37.9 | 44.8 | 44.8 | 44.8 |
| EOW | 41.4 | 48.3 | 51.7 | 58.6 | 48.3 |
| QWK | 35.0 | 50.0 | 55.0 | 60.0 | 50.0 |

Among patients with any abscesses at baseline. PBO=29; EOW=29; QWK=20.

For all of these components (except for complete clearance of abscesses), patients with Hurley Stage III disease at baseline who received weekly adalimumab dosing experienced better improvement relative to those receiving placebo (data not shown). For all patients receiving ew dosing, at least half of the mean percentage improvement noted at Week 16 was observed by Week 4: mean percentage improvement was 26% at Week 4 for inflammatory nodule count; 67% at Week 4 for abscess count; and 46% at Week 4 for draining fistula count. Between baseline and Week 16, mean serum CRP levels declined by 7.9 mg/L and 3.1 mg/L for the ew and eow groups, respectively, compared with an increase of 4.4 mg/L for the placebo group (p<0.05, ew vs. placebo).

In one particular example, at baseline, a 45 year old subject with hidradenitis suppurativa duration of 10 years, 8 months, had an HS-PGA and VAS pain score of 47. Following 16 weeks of adalimumab 40 mg administered every other week (eow), the subject achieved an HS-PGA of 3 and a VAS pain score of 33. Reduction in HS lesions in this patient following adalimumab 40 mg administered every other week (eow) for 16 weeks was a clinically relevant improvement (reduction in pain of 34%).

Among patients receiving weekly therapy, a higher proportion of patients with BMI greater than or equal to the median BMI achieved a clinical response at Week 16 compared with patients below the median BMI (22.7% vs. 13.8); among placebo-treated patients, the analogous Clinical Response ratio for those ≥median BMI: those <median BMI was 0% vs. 7.7%.

Safety Results

For safety assessment, the 3 treatment groups in Period 1 (Adalimumab 40 mg Qwk, Adalimumab 40 mg Eow, and Placebo) were assessed from Week 0 up to Week 16. For Open-label adalimumab (Period 2), patients were assessed from Week 16 through Week 52, plus 70 days after the last dose. Assessment and recording of adverse events (AE) and serious adverse events (SAE) was performed by the investigator at each study visit. Information on events that occurred 70-days after the last dose of study drug (Week 52 or early termination) was collected during a follow-up phone call.

The proportion of subjects with any adverse event (AE) was 54.9% for placebo arm, 63.5% for eow arm, and 70.6% for qw arm. Generally, the types and frequency of adverse events were consistent with results observed in the adalimumab safety database for other indications. Three subjects (all Hurley Stage III) developed serious infections: an eow subject with super infection of scrotal hidradenitis, an eow subject with a pilonidal cyst flare, and a qw subject with polymicrobial infection of the penis and scrotum. One subject in the qw arm developed a vocal cord benign neoplasm (granular cell tumor).

No fatalities, tuberculosis, opportunistic infections, demyelinating disease, congestive heart failure, lupus-like syndrome, lymphoma, or nonmelanoma skin cancer were reported during Period 1.

Nine patients experienced serious adverse events (SAE) were reported during Period 1: small intestinal obstruction and suicide attempt (1 each in the placebo group); hidradenitis, interstitial lung disease, and pilonidal cyst (1 each in the ADA eow group); anemia, non-cardiac chest pain, genital bacterial infection and *Escherichia* infection [same patient], and vocal cord neoplasm in ew group. See Tables 11 and 12 below.

TABLE 11

Treatment-Emergent Adverse Events During Period 1

| | Placebo (n = 51) | ADA eow (n = 52) | ADA ew (n = 51) |
|---|---|---|---|
| Any AE | 30 (58.8%) | 33 (63.5%) | 36 (70.6%) |
| Infectious AE | 18 (35.3%) | 22 (42.3%) | 17 (33.3%) |
| Serious AE | 2 (3.9%) | 3 (5.8%) | 4 (7.8%) |
| Serious Infectious AE | 0 | 1 (1.9%) | 1 (2.0%) |
| Malignancies | 0 | 0 | 0 |
| AE leading to withdrawal | 0 | 2 (3.8%) | 1 (2.0%) |

AE: adverse event.

A detailed break-down of different categories of AE is presented in Table 12:

TABLE 12

Treatment-emergent Adverse Events During Period 1

| | Adalimumab 40 mg Qwk DB | Adalimumab 40 mg Eow DB | Placebo DB |
|---|---|---|---|
| Total # participants affected/at risk | 36/51 (70.59%) | 33/52 (63.46%) | 30/51 (58.82%) |
| Gastrointestinal disorders | | | |
| Gastrooesophageal reflux disease [†,A] | | | |
| # participants affected/at risk Nausea [†,A] | 3/51 (5.88%) | 0/52 (0%) | 0/51 (0%) |
| # participants affected/at risk Vomiting [†,A] | 4/51 (7.84%) | 2/52 (3.85%) | 1/51 (1.96%) |
| # participants affected/at risk General disorders Fatigue [†,A] | 1/51 (1.96%) | 2/52 (3.85%) | 3/51 (5.88%) |
| # participants affected/at risk Infections and infestations Folliculitis [†,A] | 3/51 (5.88%) | 2/52 (3.85%) | 2/51 (3.92%) |
| # participants affected/at risk Nasopharyngitis [†,A] | 0/51 (0%) | 0/52 (0%) | 3/51 (5.88%) |
| # participants affected/at risk Upper respiratory tract infection [†,A] | 6/51 (11.76%) | 7/52 (13.46%) | 6/51 (11.76%) |
| # participants affected/at risk Musculoskeletal and connective tissue disorders Arthralgia [†,A] | 4/51 (7.84%) | 4/52 (7.69%) | 2/51 (3.92%) |
| # participants affected/at risk | 3/51 (5.88%) | 0/52 (0%) | 1/51 (1.96%) |

TABLE 12-continued

Treatment-emergent Adverse Events During Period 1

| | Adalimumab 40 mg Qwk DB | Adalimumab 40 mg Eow DB | Placebo DB |
|---|---|---|---|
| Nervous system disorders Headache [†,A] | | | |
| # participants affected/at risk Respiratory, thoracic and mediastinal disorders Cough [†,A] | 8/51 (15.69%) | 7/52 (13.46%) | 2/51 (3.92%) |
| # participants affected/at risk Oropharyngeal pain [†,A] | 3/51 (5.88%) | 1/52 (1.92%) | 0/51 (0%) |
| # participants affected/at risk Skin and subcutaneous tissue disorders Hidradenitis [†,A] | 1/51 (1.96%) | 3/52 (5.77%) | 1/51 (1.96%) |
| # participants affected/at risk Pruritus [†,A] | 4/51 (7.84%) | 6/52 (11.54%) | 6/51 (11.76%) |
| # participants affected/at risk Gastrointestinal disorders Abdominal pain upper [†,A] | 1/51 (1.96%) | 3/52 (5.77%) | 0/51 (0%) |
| # participants affected/at risk Diarrhoea [†,A] | 1/51 (1.96%) | 2/52 (3.85%) | 1/51 (1.96%) |
| # participants affected/at risk General disorders Injection site pruritus [†,A] | 0/51 (0%) | 2/52 (3.85%) | 2/51 (3.92%) |
| # participants affected/at risk Oedema peripheral [†,A] | 2/51 (3.92%) | 0/52 (0%) | 0/51 (0%) |
| # participants affected/at risk Pain [†,A] | 0/51 (0%) | 1/52 (1.92%) | 2/51 (3.92%) |
| # participants affected/at risk Pyrexia [†,A] | 0/51 (0%) | 2/52 (3.85%) | 0/51 (0%) |
| # participants affected/at risk Infections and infestations Bronchitis [†,A] | 0/51 (0%) | 2/52 (3.85%) | 1/51 (1.96%) |
| # participants affected/at risk Ear infection [†,A] | 1/51 (1.96%) | 0/52 (0%) | 2/51 (3.92%) |
| # participants affected/at risk Herpes simplex [†,A] | 0/51 (0%) | 0/52 (0%) | 2/51 (3.92%) |
| # participants affected/at risk Influenza [†,A] | 0/51 (0%) | 2/52 (3.85%) | 0/51 (0%) |
| # participants affected/at risk Sinusitis [†,A] | 2/51 (3.92%) | 1/52 (1.92%) | 0/51 (0%) |
| # participants affected/at risk Tonsillitis [†,A] | 2/51 (3.92%) | 0/52 (0%) | 1/51 (1.96%) |
| # participants affected/at risk Investigations Blood cholesterol increased [†,A] | 0/51 (0%) | 0/52 (0%) | 2/51 (3.92%) |
| # participants affected/at risk Metabolism and nutrition disorders Hypercholesterolaemia [†,A] | 0/51 (0%) | 0/52 (0%) | 2/51 (3.92%) |
| # participants affected/at risk Musculoskeletal and connective tissue disorders Myalgia [†,A] | 1/51 (1.96%) | 2/52 (3.85%) | 0/51 (0%) |
| # participants affected/at risk Nervous system disorders Dizziness [†,A] | 1/51 (1.96%) | 1/52 (1.92%) | 2/51 (3.92%) |
| # participants affected/at risk | 0/51 (0%) | 1/52 (1.92%) | 2/51 (3.92%) |

TABLE 12-continued

Treatment-emergent Adverse Events During Period 1

| | Adalimumab 40 mg Qwk DB | Adalimumab 40 mg Eow DB | Placebo DB |
|---|---|---|---|
| Respiratory, thoracic and mediastinal disorders Dyspnoea [†,A] | | | |
| # participants affected/at risk Sinus congestion [†,A] | 0/51 (0%) | 2/52 (3.85%) | 0/51 (0%) |
| # participants affected/at risk Skin and subcutaneous tissue disorders Dermatitis allergic [†,A] | 2/51 (3.92%) | 0/52 (0%) | 0/51 (0%) |
| # participants affected/at risk Pityriasis rosea [†,A] | 2/51 (3.92%) | 0/52 (0%) | 0/51 (0%) |
| # participants affected/at risk Psoriasis [†,A] | 2/51 (3.92%) | 0/52 (0%) | 0/51 (0%) |
| # participants affected/at risk Rash [†,A] | 0/51 (0%) | 0/52 (0%) | 2/51 (3.92%) |
| # participants affected/at risk Urticaria [†,A] | 2/51 (3.92%) | 0/52 (0%) | 0/51 (0%) |
| # participants affected/at risk | 2/51 (3.92%) | 0/52 (0%) | 0/51 (0%) |

[†] Indicates events were collected by systematic assessment.
[A] Term from vocabulary, MedDRA 13.1
Frequency Threshold Above Which Other Adverse Events are Reported: 3%

In summary, no deaths, malignancies, cases of tuberculosis or opportunistic infections occurred. During Period 1, the proportion of patients in each treatment arm experiencing adverse events (Tables 11 and 12) was higher for the eow and ew groups compared with the placebo group. Headaches, typically described as mild or moderate in severity, accounted for much of the numerical imbalance in adverse events among the treatment groups. A greater proportion of patients who started with weekly dosing in Period 1 and switched to eow dosing in Period 2 experienced any adverse event, any infectious adverse event, or any serious adverse event compared with patients who received eow dosing in Periods 1 and/or 2 (Tables 11 and 12 also see Table 13 below). Patients who underwent dose escalation in Period 2 had similar adverse event frequencies compared with patients who received eow dosing. Fifteen patients receiving adalimumab experienced one or more serious adverse events during the trial, with the most common types of serious adverse events being hidradenitis suppurativa (5 patients), infectious complications of hidradenitis suppurativa (4 patients), and anemia (2 patients; one patient had a history of intermittent GI bleeding from ulcerative colitis and one patient had low hemoglobin concentration at screening).

The proportion of patients experiencing treatment-emergent common toxicity criteria (CTC) grade 3 adverse events in clinical chemistry or hematology values was low and similar across the treatment groups in Period 1, and remained low during Period 2. The prevalence of anti-adalimumab antibodies for the 52 week study was 10.4% (16 of 154 subjects).

The types and frequencies of adverse events were generally consistent with what has been observed in clinical trials of adalimumab in other indications. However, super infection of hidradenitis suppurativa lesions and/or pilonidal cyst flare, though infrequent, was observed with active treatment but not with placebo treatment. While not wishing to be bound by any particular theory, it is possible that this is a safety signal associated with adalimumab-mediated immunosuppression of contaminated skin and soft tissue, although it cannot be ruled out at this stage that it is a spurious signal. That said, the types and frequency of adverse events were consistent with results observed in other studies for treatment of other indications with adalimumab.

In conclusion, the above study showed that human anti-TNFα antibodies, such as adalimumab, are efficacious and safe for treating subjects having human hidradenitis suppurativa (HS), including patients with moderate to severe forms of the disease.

Example 2

Safety and Efficacy of Adalimumab in Subjects with Moderate to Severe Chronic Hidradenitis Suppurativa (HS)

The following example is a continuation of the study described in Example 1. This example shows the partial maintenance of efficacy and continued safety of adalimumab 40 mg every other week (eow) administration for hidradenitis suppurativa patients over a period of at least several weeks (at least 8 weeks) after the initial 16-week, double-blind, placebo-controlled treatment period. The pharmacokinetics and immunogenicity of adalimumab following subcutaneous (s.c.) injection were also assessed.

Subjects who have received 16 weeks of either weekly or biweekly injections of adalimumab (or placebo) in the randomized, double-blind, placebo-controlled treatment period, as described in Example 1 above, receive open-label adalimumab (40 mg eow) s.c. injection for an additional 36 weeks for evaluating long-term safety and efficacy of adalimumab administration in this patient population (study design is described in FIG. 1). Patients having a sub-optimal response at Weeks 28 or 31 had the option of dose-escalating to ew dosing.

As described above in Example 1, 51 placebo (pbo), 52 every other week (eow), and 51 weekly (ew) patients were enrolled in Period 1. Week 16 Clinical Response rates were 3.9% for pbo, 9.6% for eow, 17.6% for ew patients (P=0.025, ew vs. pbo (n=46/51/45)).

Week 52 Clinical Response rates were 17.4% for pbo-> eow (n=46), 5.9% for eow->eow (n=51), and 8.9% for ew->eow (n=45) patients. 89 patients had sub-optimal responses at Weeks 28 or 31, and were dose-escalated to ew dosing; of these, 13 (15%) had a clinical response at Week 52. The percentage of patients with serious adverse events was 3.9% for pbo, 5.8% for eow, and 7.8% ew patients during Period 1; 2.2% for pbo->eow, 3.9% for eow->eow, and 4.4% for ew->eow patients during Period 2; and 5.6% for dose escalation patients.

Among patients who had received ew dosing in Period 1, the proportion of patients achieving clinical response was maintained for 8 weeks after switching to eow dosing in Period 2 (FIG. 3). However, with continued eow dosing, the proportion of patients achieving clinical response declined, and eventually became similar to the response rate for patients who had never received weekly dosing (but have received eow dosing since week 16). Of 24 ew-treated patients who had HS-PGA of mild or better response at the entry of Period 2, 12 (50%) retained this response at Week 28, 12 weeks following step-down to eow dosing. Eighty-nine patients (63% of those who entered Period 2) had a sub-optimal response at Weeks 28 or 31 and were dose-escalated to ew dosing; of these, 13 (15%) had a clinical response at Week 52. Thus it appears that ew dosing (for 40 mg ADA) was more effective than eow dosing, although eow dosing was sufficient for a proportion of the patients.

The safety profile was similar for patients receiving adalimumab weekly therapy compared to those receiving every other week therapy. Table 13 below compares AE between Period 1 and Period 2.

and health-related quality of life impairment and work productivity in patients with hidradenitis suppurativa, and confirmed that hidradenitis suppurativa is mediated, directly or indirectly, in part by pathogenically elevated levels of TNFα.

Significant, dose-dependent improvement in the global assessment of these patients was achieved at the Week 16 primary endpoint, with evidence of improvement in important secondary endpoints at earlier time points. Patients across the spectrum of severity benefited, and patients with less severe and more reversible (e.g., less scarring) disease at baseline (Hurley Stage I or II) were more likely to benefit. Results from the placebo-controlled portion of the study showed that benefit is more consistent and stable with weekly than every other week dosing; this finding was corroborated by the outcomes in the open-label portion of the study, in which the majority of patients escalated their dosing frequency to weekly because of sub-optimal response to every other week dosing and in which dose escalation improved treatment outcomes. A larger treatment effect was noted for improvement of inflammatory nodules and draining fistulas than for improvement of abscesses.

In addition to evaluating therapeutic effects, this study corroborated and expanded the knowledge of several important epidemiologic characteristics of the HS population. Consistent with previous epidemiologic studies of risk factors associated with HS, the majority of the study patient population was female, their average weight exceeded 90 kg, and the majority were smokers. The observation that approximately 20% of the study patients, who were mostly from the United States, were African American is important, as it supports the impression of an increased prevalence of this disease in this population that is subject to multiple health disparities. Moreover, the proportion of non-white patients in the study population may be an underestimate of the proportion in the general population, as numerous studies have demonstrated a reduced willingness by non-white patients to participate in clinical trials.

TABLE 13

Adverse Events (AE) During Period 1 and Period 2

| | Period 1 | | | Periods 1 and 2[a] | | |
|---|---|---|---|---|---|---|
| | Placebo n = 51 | ADA eow n = 52 | ADA ew n = 51 | PBO/eow + eow/eow N = 98 | ew/eow N = 51 | Dose Escalation N = 89 |
| n (%) | | | | | | |
| Any adverse event | 30 (58.8) | 33 (63.5) | 36 (70.6) | 60 (61.2) | 44 (86.3) | 50 (56.2) |
| Any infectious adverse event | 18 (35.3) | 22 (42.3) | 17 (33.3) | 41 (41.8) | 30 (58.8) | 24 (27.0) |
| Serious adverse event | 2 (3.9) | 3 (5.8) | 4 (7.8) | 5 (5.1) | 6 (11.8) | 5 (5.6) |
| Serious infectious adverse event | 0 | 1 (1.9) | 1 (2.0) | 1 (1.0) | 3 (5.9) | 3 (3.4) |
| Any adverse event leading to study drug discontinuation | 0 | 2 (3.8) | 2 (3.9) | 4 (4.1) | 5 (9.8) | 5 (5.6) |
| Malignancies | 0 | 0 | 0 | 0 | 0 | 0 |
| Adverse Events in >7% of patients | | | | | | |
| Nausea | 1 (2.0) | 2 (3.8) | 4 (7.8) | 2 (2.0) | 6 (11.8) | 1 (1.1) |
| Fatigue[b] | 2 (3.9) | 2 (3.8) | 3 (5.9) | 5 (5.1) | 5 (9.8) | 1 (1.1) |
| Influenza[b] | 0 | 1 (1.9) | 2 (3.9) | 2 (2.0) | 4 (7.8) | 1 (1.1) |
| Nasopharyngitis | 6 (11.8) | 7 (13.5) | 6 (11.8) | 13 (13.3) | 9 (17.6) | 5 (5.6) |
| Upper Respiratory Tract Infection | 2 (3.9) | 4 (7.7) | 4 (7.8) | 7 (7.1) | 6 (11.8) | 0 (0) |
| Arthralgia[b] | 1 (2.0) | 0 | 3 (5.9) | 5 (5.1) | 4 (7.8) | 0 (0) |
| Headache | 2 (3.9) | 7 (13.5) | 8 (15.7) | 9 (9.2) | 10 (19.6) | 5 (5.6) |
| Cough[b] | 0 | 1 (1.9) | 3 (5.9) | 1 (1.0) | 5 (9.8) | 2 (2.2) |
| Hidradenitis | 6 (11.8) | 7 (13.5) | 4 (7.8) | 17 (17.3) | 12 (23.5) | 6 (6.7) |
| Vomiting | 3 (5.9) | 2 (3.8) | 1 (2.0) | | | |

[a]AEs after dose escalation were not included in the eow groups.
[b]Occurred in <7% of patients in all treatment groups during Period 1.

This Phase 2 study demonstrated the efficacy and tolerability of adalimumab in treating the signs of inflammation, pain, Additionally, the substantial baseline level of pain medication used (particularly of opioid use by 10% of the enrollees), as well as the health-related quality of life and work productivity impairment for these patients, was striking, underscoring the debilitating nature of hidradenitis suppurativa and its significant unmet medical need. The mean baseline DLQI score of 15 in this study was 3.6 points higher (worse) than the mean baseline DLQI of moderate-severe psoriasis patients enrolled in an adalimumab Phase III psoriasis trial; the mean baseline total work productivity impairment was twice as great as that of moderate-severe psoriasis patients enrolled in an adalimumab Phase III trial; and the mean baseline PHQ-9 score of 9.5 indicated moderate depression. Conversely, treatment with weekly adalimumab resulted in significant and clinically relevant improvement in patient-reported outcomes: the 6-point mean improvement in DLQI between Weeks 0 and 16 exceeded the minimum clinically important difference (MCID) for DLQI (2.3-5.7 points); a significantly higher proportion of patients receiving weekly dosing achieved the clinically meaningful reduction in pain; the mean 3.8-point reduction (improvement) in PHQ-9 scores from Week 0 to 16 exceeded the MCID (½ of the baseline standard deviation for PHQ-9); and adalimumab ew patients achieved statistically significantly ($p<0.001$) greater improvement compared to placebo by 20.34 units in TWPI, exceeding the MCID (½ of the baseline standard deviation).

Adalimumab was well tolerated in this study. The proportion of patients with infectious adverse events were similar in both active-treatment groups and the placebo group during the 16-week double blind period, and the proportion of patients who experienced adverse events leading to study discontinuation or serious adverse events was low. The adverse event pattern did not change through 52 weeks of therapy. The safety profile was similar for patients receiving adalimumab weekly therapy compared to those receiving every other week therapy. Given the apparent increase in efficacy achieved with the higher dose, the risk-benefit balance appears to favor weekly dosing.

In conclusion, weekly adalimumab therapy was effective for improvement of moderate to severe HS for up to 52 weeks. A decline in response rate was seen following switch from ew to eow dosing during Period 2. Dose escalation to ew dosing resulted in improved efficacy. The proportion of patients experiencing serious adverse events was low through 52 weeks of treatment.

In summary, results described above show that adalimumab is the first systemic therapy to have demonstrated significant efficacy in patients with moderate to severe hidradenitis suppurativa in achieving control of objective signs of disease and in reducing pain. Serious adverse event rates associated with the treatment were low, and were similar across all treatment groups.

Example 3

Adalimumab is Effective at Treating Subpopulations with Hidradenitis Suppurativa (HS)

This example provides a subanalysis of the 52-week Phase II study described above in Examples 1 and 2. Specifically, the following example examines the adalimumab response across subgroups of patients with moderate to severe hidradenitis suppurativa.

The goal of this subanaylsis was to assess the relationship between age, sex, race, median weight, and current smoking status, and clinical efficacy in a clinical trial of adalimumab (ADA) in hidradenitis suppurativa (HS).

The methods of the study are described above in Examples 1 and 2, and are reiterated here. Moderate to severe HS patients (patients with HS-Physician's Global Assessment [HS-PGA]≥moderate) were randomized 1:1:1 to ADA 40 mg weekly (ew) (after 160 mg at Week 0, 80 mg at Week 2), ADA 40 mg every other week (eow) (after 80 mg at Week 0), or placebo (pbo) in a 52-week, Phase II clinical trial. The primary endpoint was the proportion of patients at Week 16 with a Clinical Response (defined as achieving an HS-PGA score of clear, minimal, or mild, with at least a two grade improvement relative to baseline) at Week 16.

For this analysis, data from subsets of the Intention-to-Treat population were grouped based on patient age, sex, race, median weight, and current smoking status, for a post hoc analysis of the effect of these factors on clinical efficacy. Non-responder imputation was used for missing data.

Overall Week 16 Clinical Response rates for pbo, eow, and ew patients were 3.9% (n=2/51), 9.6% (n=5/52), and 17.6% (n=9/51) (P=0.025, ew vs. pbo).

Age: At Week 16, Clinical Responses were achieved as follows in patients <40 years: pbo 5.9% (2/34), eow 6.5% (2/31) and ew 12.1% (4/33); for patients ≥40 years: pbo 0% (0/17), eow 15.0% (3/21) and ew 29.4% (5/18; P=0.047, ew vs. pbo).

Sex: At Week 16, Clinical Responses were achieved as follows: for males: pbo 0% (0/15), eow 14.3% (2/14), and ew 13.3% (2/15); for females: pbo 5.6% (2/36), eow 7.9% (3/38), and ew 19.4% (7/36).

Race: At Week 16, Clinical Responses were achieved as follows: for whites: pbo 2.6% (1/38), eow 7.9% (3/38), and ew 21.6% (8/37; P=0.016, ew vs. pbo); for non-whites: pbo 7.7% (1/13), eow 14.3% (2/14), and ew 7.1% (1/14).

Body weight: At Week 16, Clinical Responses were achieved as follows: for patients <96.5 kg: pbo 7.7% (2/26), eow 4.5% (1/30), and ew 17.2% (5/29); for patients >96.5 kg: pbo 0% (0/25), eow 13.3% (4/30; P=0.048, eow vs. pbo), and ew 18.2% (4/22; P=0.013, ew vs. pbo).

Current smoking status: At Week 16, Clinical Responses were achieved as follows: for current smokers: pbo 3.4% (1/29), eow 11.5% (3/26), and ew 23.3% (7/30; P=0.041, ew vs. pbo); and for current non-smokers: pbo 4.5% (1/22), eow 7.7% (2/26), and ew 9.5% (2/21).

The results show that weekly adalimumab therapy was effective for the treatment of moderate to severe HS at Week 16. In this post-hoc analysis, the greatest Clinical Response rates were seen in patients greater than 40 years old, females, whites, and current smokers. No apparent differences were seen between body weight subgroups in this analysis.

Example 4

Impact of Weight and Body Mass Index on High-sensitivity C-reactive Protein Response to Adalimumab in Hidradenitis Suppurativa Patients This example provides a subanalysis of the 52-week Phase II study described above in Examples 1 and 2. The goal of the subanalysis was to determine the impact of adalimumab treatment on high-sensitivity C-reactive protein (hs-CRP) in moderate to severe hidradenitis suppurativa (HS) patients, and to determine whether weight or BMI had an effect on hsCRP response to adalimumab.

The following example is based on data from a Phase II, 52-week (wk) trial, where the initial 16 wk portion was double-blind and placebo-controlled (see Examples 1 and 2). Patients with moderate to severe HS (HS-Physician's Global Assessment [HS-PGA]≥moderate) were randomized 1:1:1 to adalimumab 40 mg weekly (ew) (after 160 mg at Wk 0 and 80 mg at Wk 2), adalimumab 40 mg every other wk (eow) (after 80 mg at Wk 0), or placebo (pbo). The primary efficacy variable was the proportion of patients who achieved Clinical Response, defined as an HS-PGA score of clear, minimal, or mild, with at least a two grade improvement relative to baseline, at Wk 16.

This post-hoc analysis assessed mean change in hs-CRP concentration from baseline to Wk 16 by treatment group; patients were further grouped by weight ≤100 kg and >100 kg and BMI <25, ≥25-<30, and ≥30. Missing data were imputed as non-response.

154 patients were enrolled: 51 pbo/52 eow/51 ew. At Week 16, the proportion of patients achieving Clinical Response was 3.9%/9.6%/17.6% for pbo/eow/ew groups (P=0.025, ew vs. pbo). At baseline, mean hs-CRP concentrations were: 13.8/17.8/22.2 mg/L for pbo/eow/ew groups (n=36/40/35). At Week 16, mean change from baseline in hs-CRP was 5.5/−1.6/−3.2 mg/L for pbo/eow/ew patients (P=0.034, ew vs. pbo). For pbo/ew/eow patients ≤100 kg and >100 kg, mean change from baseline to Wk 16 was 8.3/−4.0/−4.4 mg/L (n=20/19/24; P=0.020, eow vs. pbo; P=0.011, ew vs. pbo) and 2.0/0.5/−0.7 mg/L (n=16/21/11). For pbo/eow/ew patients with BMI <25/≥25-<30/≥30, mean change from baseline to Wk 16 was 4.7/−1.0/−6.0 (n=6/4/6); 14.2/−11.6/4.8 (n=3/8/9; P=0.018, eow vs. pbo); 4.7/1.2/−6.0 (n=27/28/20).

The conclusion of the subanalysis was that weekly adalimumab therapy was effective in reducing hs-CRP concentrations in moderate to severe HS patients regardless of weight or BMI. For weight, the greatest hs-CRP reductions occurred in patients ≤100 kg receiving weekly dosing; for BMI, comparable hs-CRP reductions were seen in normal and obese patients receiving weekly dosing.

Example 5

HiSCR Scoring System for Treatment of Hidradenitis Suppurativa (HS)

The following example describes a new scoring system for assessing improvements in a subject having HS. The new scoring system, called Hidradenitis Suppurativa Clinical Response (HiSCR), was developed based on clinical trial data (described above) obtained using the anti-TNFα antibody adalimumab for the treatment of HS.

HiSCR is defined as at least a 50% reduction in the total inflammatory lesion (abscess and inflammatory nodule) count (AN count) relative to baseline, with no increase in abscess count and no increase in draining fistula count. Treated subjects are declared clinical responders only if they experience at least 50% reduction in total inflammatory lesion (abscess+inflammatory nodule) count, and also no increase in abscess count and no increase in draining fistula count.

HiSCR was applied to the raw clinical data from the Phase II clinical trial described in Examples 1-4 to assess the efficacy of adalimumab using HiSCR. The results from this analysis are shown in Table 14.

Table 14 shows the proportion of patients achieving HiSCR, i.e., at least 50% reduction in inflammatory lesion count with no increase in abscess count and no increase in draining fistula count, at Weeks 2, 4, 8, 12 and 16, among those patients who were Hurley Stage II or III, and who had more than two abscesses or inflammatory nodules, but less than 20 draining fistulas at baseline. The response rates observed at week 12 for HiSCR were about 61% and about 16% in the adalimumab qwk group and placebo group, respectively.

TABLE 14

Proportion (Percentage) of Patients Achieving HiSCR at Weeks 2, 4, 8, 12 and 16

| Patient Group | Week 2 | Week 4 | Week 8 | Week 12 | Week 16 |
|---|---|---|---|---|---|
| Placebo | 8.1 | 13.5 | 32.4 | 16.2 | 21.6 |
| EOW | 21.1 | 31.6$ | 31.6 | 28.9 | 31.6 |
| QWK | 41.7# | 47.2# | 50.0 | 61.1#,& | 55.6#,& |

Excluding subjects with ≤2 abscesses/inflammatory nodules and >20 draining fistulas at baseline; N = 37 for PRO, N = 38 for EOW, N = 36 for QWK, ITT, NRI.
p < 0.05, qwk vs. pbo;
$p < 0.05, eow vs. pbo;
&p < 0.05, qwk vs. eow.

HiSCR may be used to assess clinical efficacy, as the results described in Table 14 showed that improved efficacy would be seen at all study visits for patients treated with qwk dosing compared with those treated with eow dosing. At Week 12, the number of treatments needed to achieve clinical success is projected to be 2.2 with qwk dosing, compared with 7.9 with eow dosing.

REFERENCES

1. Esmann S, Jemec G B. Psychosocial Impact of Hidradenitis Suppurativa: A Qualitative Study. Acta Derm Venereol 2011.
2. Jemec G B, Wendelboe P. Topical clindamycin versus systemic tetracycline in the treatment of hidradenitis suppurativa. J Am Acad Dermatol 1998; 39:971-4.
3. Kurzen H, Kurokawa I, Jemec G B, et al. What causes hidradenitis suppurativa? Exp Dermatol 2008; 17:455-6; discussion 7-72.
4. Shah N. Hidradenitis suppurativa: a treatment challenge. Am Fam Physician 2005; 72:1547-52.
5. Fimmel S, Zouboulis C C. Comorbidities of hidradenitis suppurativa (acne inversa). Dermato-endocrinology 2010; 2:9-16.
6. van der Zee H H, van der Woude C J, Florencia E F, Prens E P. Hidradenitis suppurativa and inflammatory bowel disease: are they associated? Results of a pilot study. Br J Dermatol 2010; 162:195-7.
7. Revuz J E, Canoui-Poitrine F, Wolkenstein P, et al. Prevalence and factors associated with hidradenitis suppurativa: results from two case-control studies. J Am Acad Dermatol 2008; 59:596-601.
8. Jemec G B. Hidradenitis suppurativa. J Cutan Med Surg 2003; 7:47-56.
9. Zouboulis C C. Disorders of the Apocrine Sweat Glands. In: Wolff K, Goldsmith L A, Katz S I, Gilchrest B A, Paller A S, Leffell D J, eds. Fitzpatrick's Dermatology in General Medicine, New York City: McGraw Hill; 2010.
10. Konig A, Lehmann C, Rompel R, Happle R. Cigarette smoking as a triggering factor of hidradenitis suppurativa. Dermatology 1999; 198:261-4.
11. Sartorius K, Emtestam L, Jemec G B, Lapins J. Objective scoring of hidradenitis suppurativa reflecting the role of tobacco smoking and obesity. Br J Dermatol 2009; 161: 831-9.
12. von der Werth J M, Jemec G B. Morbidity in patients with hidradenitis suppurativa. Br J Dermatol 2001; 144:809-13.
13. Wolkenstein P, Loundou A, Barrau K, Auquier P, Revuz J. Quality of life impairment in hidradenitis suppurativa: a study of 61 cases. J Am Acad Dermatol 2007; 56:621-3.
14. Using PHQ-9 Diagnosis and Score for Initial Treatment Selection. (Accessed Feb. 22, 2010, at http://www.depression-primarycare.org/clinicians/toolkits/materials/forms/phq9/score_table.)

15. Matusiak L, Bieniek A, Szepietowski J C. Psychophysical aspects of hidradenitis suppurativa. Acta Derm Venereol 2010; 90:264-8.
16. Alikhan A, Lynch P J, Eisen D B. Hidradenitis suppurativa: a comprehensive review. J Am Acad Dermatol 2009; 60:539-61; quiz 62-3.
17. Plewig G. Acne and Rosacea. In: Burgdorf W H C, Plewig G, Wolff H H, Landthaler M, eds. Braun-Falco's Dermatology, 3rd ed. Heidelberg: Springer Medlzin Verlag 2009: 1002-4.
18. Clemmensen O J. Topical treatment of hidradenitis suppurativa with clindamycin. Int J Dermatol 1983; 22:325-8.
19. Mortimer P S, Dawber R P, Gales M A, Moore R A. A double-blind controlled cross-over trial of cyproterone acetate in females with hidradenitis suppurativa. Br J Dermatol 1986; 115:263-8.
20. van der Zee H H, de Ruiter L, van den Broecke D G, Dik W A, Laman J D, Prens E P. Elevated levels of TNF-alpha, IL-1beta and IL-10 in hidradenitis suppurativa skin; a rationale for targeting TNF-alpha and IL-1beta. Br J Dermatol 2011.
21. Lebwohl B, Sapadin A N. Infliximab for the treatment of hidradenitis suppurativa. J Am Acad Dermatol 2003; 49:5275-6.
22. Rosi Y L, Lowe L, Kang S. Treatment of hidradenitis suppurativa with infliximab in a patient with Crohn's disease. J Dermatolog Treat 2005; 16:58-61.
23. Haslund P, Lee R A, Jemec G B. Treatment of hidradenitis suppurativa with tumour necrosis factor-alpha inhibitors. Acta Derm Venereol 2009; 89:595-600.
24. Harde V, Mrowietz U. Treatment of severe recalcitrant hidradenitis suppurativa with adalimumab. J Dtsch Dermatol Ges 2009; 7:139-41.
25. Adams D R, Yankura J A, Fogelberg A C, Anderson B E. Treatment of hidradenitis suppurativa with etanercept injection. Arch Dermatol 2010; 146:501-4.
26. Grant A, Gonzalez T, Montgomery M O, Cardenas V, Kerdel F A. Infliximab therapy for patients with moderate to severe hidradenitis suppurativa: a randomized, double-blind, placebo-controlled crossover trial. J Am Acad Dermatol 2010; 62:205-17.
27. Miller I, Lynggaard C D, Lophaven S, Zachariae C, Dufour D N, Jemec G B. A double blind Placebo Controlled randomised Trial of Adalimumab in the treatment of Hidradenitis Suppurativa. Br J Dermatol 2011.
28. Hurley H J. Axillary hyperhidrosis, apocrine bromhidrosis, hidradenitis suppurativa, and familial benign pemphigus: surgical approach. In: Roenigk R K, Roenigk H H, eds. Dermatologic Surgery. New York: Dekker; 1989:729.
29. Manton K G, Patrick C H, Johnson K W. Health differentials between blacks and whites: recent trends in mortality and morbidity. Milbank Q 1987; 65 Suppl 1:129-99.
30. Corbie-Smith G, Thomas S B, Williams M V, Moody-Ayers S. Attitudes and beliefs of African Americans toward participation in medical research. J Gen Intern Med 1999; 14:537-46.
31. Shavers V L, Lynch C F, Burmeister L F. Racial differences in factors that influence the willingness to participate in medical research studies. Ann Epidemiol 2002; 12:248-56.
32. Revicki D A, Willian M K, Menter A, Saurat J H, Harnam N, Kaul M. Relationship between clinical response to therapy and health-related quality of life outcomes in patients with moderate to severe plaque psoriasis. Dermatology 2008; 216:260-70.
33. Kimball A B, Yu A P, Signorovitch J, et al. The effects of adalimumab treatment and psoriasis severity on self-reported work productivity and activity impairment for patients with moderate to severe psoriasis, accepted.
34. Shikiar R, Willian M K, Okun M M, Thompson C S, Revicki D A. The validity and responsiveness of three quality of life measures in the assessment of psoriasis patients: results of a phase II study. Health Qual Life Outcomes 2006; 4:71.
35. Farrar J T, Berlin J A, Strom B L. Clinically important changes in acute pain outcome measures: a validation study. J Pain Symptom Manage 2003; 25:406-11.
36. Norman G R, Sloan J A, Wyrwich K W. Interpretation of changes in health-related quality of life: the remarkable universality of half a standard deviation. Med Care 2003; 41:582-92.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

The invention claimed is:

1. A method for treating a subject having moderate to severe hidradenitis suppurativa (HS), the method comprising:
   at week 0 administering a first loading dose of 160 mg of an isolated human anti-TNFα antibody, or antigen binding portion thereof, to the subject, wherein the first loading dose is administered as four 40 mg doses in one day or two 40 mg doses per day over two consecutive days;
   at week 2 administering a second loading dose of 80 mg of the human anti-TNFα antibody, or antigen binding portion thereof, to the subject, wherein the second loading dose is administered as two 40 mg doses in one day; and
   starting at week 4 administering a treatment dose of 40 mg of the human anti-TNFα antibody, or antigen binding portion thereof, to the subject weekly,
   wherein the anti-TNFα antibody, or antigen binding portion thereof, comprises a variable light chain comprising a CDR3 domain comprising the amino acid sequence of SEQ ID NO: 3; a CDR2 domain comprising the amino acid sequence of SEQ ID NO: 5, and a CDR1 domain comprising the amino acid sequence of SEQ ID NO: 7; and comprises a variable heavy chain comprising a CDR3 domain comprising the amino acid sequence of SEQ ID NO: 4, a CDR2 domain comprising the amino acid sequence of SEQ ID NO: 6, and a CDR1 domain comprising the amino acid sequence of SEQ ID NO: 8.

2. The method of claim 1, wherein the subject has HS lesions in at least two distinct anatomic areas prior to treatment.

3. The method of claim 1, wherein the subject had an inadequate response to, contraindication to, or was intolerant to oral antibiotics for treatment of their HS.

4. The method of claim 1, wherein the anti-TNFα antibody, or antigen binding portion thereof, is administered subcutaneously.

5. The method of claim 1, wherein the anti-TNFα antibody, or antigen binding portion thereof, dissociates from human TNFα with a $K_d$ of $1\times10^{-8}$ M or less and a $k_{off}$ rate constant of $1\times10^{-3}$ $s^{-1}$ or less, both determined by surface plasmon resonance, and neutralizes human TNFα cytotoxicity in a standard in vitro L929 assay with an $IC_{50}$ of $1\times10^{-7}$ M or less.

6. The method of claim 1, wherein the anti-TNFα antibody, or antigen binding portion thereof, has a light chain variable region (LCVR) comprising the amino acid sequence of SEQ ID NO: 1 and a heavy chain variable region (HCVR) comprising the amino acid sequence of SEQ ID NO: 2.

7. The method of claim 1, wherein the anti-TNFα antibody, or antigen binding portion thereof, is adalimumab.

8. The method of claim 1, wherein anti-TNFα antibody, or antigen binding portion thereof, is administered with at least one additional therapeutic agent.

9. The method of claim 1, wherein the subject is selected from the group consisting of a subject having HS at Hurley Stage II or III, a subject having an AN count of greater than or equal to 3 at baseline, a subject who is female, a subject who is over 40 years old, a subject who is a smoker, or any combination thereof.

10. The method of claim 1, wherein the subject achieves an HiSCR at week 12 of the treatment.

11. The method of claim 1, wherein the subject achieves at least a 30% reduction in skin pain at week 12 of the treatment.

12. A method for decreasing the number of inflammatory lesions (AN count) in a subject having moderate to severe hidradenitis suppurativa (HS), said method comprising systemically
   at week 0 administering a first loading dose of 160 mg of an isolated human anti-TNFα antibody, or antigen binding portion thereof, to the subject, wherein the first loading dose is administered as four 40 mg doses in one day or two 40 mg doses per day over two consecutive days;
   at week 2 administering a second loading dose of 80 mg of the human anti-TNFα antibody, or antigen binding portion thereof, to the subject, wherein the second loading dose is administered as two 40 mg doses in one day; and
   starting at week 4 administering a treatment dose of 40 mg of the human anti-TNFα antibody, or antigen binding portion thereof, to the subject weekly,
   wherein the anti-TNFα antibody, or antigen binding portion thereof, comprises a variable light chain comprising a CDR3 domain comprising the amino acid sequence of SEQ ID NO: 3; a CDR2 domain comprising the amino acid sequence of SEQ ID NO: 5, and a CDR1 domain comprising the amino acid sequence of SEQ ID NO: 7; and comprises a variable heavy chain comprising a CDR3 domain comprising the amino acid sequence of SEQ ID NO: 4, a CDR2 domain comprising the amino acid sequence of SEQ ID NO: 6, and a CDR1 domain comprising the amino acid sequence of SEQ ID NO: 8.

13. The method of claim 12, wherein the AN count is reduced by at least 50% reduction in the subject relative to baseline AN count.

14. The method of claim 13, wherein the subject has no increase in an abscess count and/or no increase in a draining fistula count following administration with the anti-TNFα antibody, or antigen binding portion thereof.

15. The method of claim 12, wherein the subject has no increase in an abscess count and/or no increase in a draining fistula count following administration with the anti-TNFα antibody, or antigen binding portion thereof.

16. The method of claim 12, wherein the subject has HS lesions in at least two distinct anatomic areas prior to treatment.

17. The method of claim 12, wherein the subject had an inadequate response to, contraindication to, or was intolerant to oral antibiotics for treatment of their HS.

18. The method of claim 12, wherein the anti-TNFα antibody, or antigen binding portion thereof, is administered subcutaneously.

19. The method of claim 12, wherein the anti-TNFα antibody, or antigen binding portion thereof, dissociates from human TNFα with a $K_d$ of $1 \times 10^{-8}$ M or less and a $k_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less.

20. The method of claim 12, wherein the anti-TNFα antibody, or antigen binding portion thereof, has a light chain variable region (LCVR) comprising the amino acid sequence of SEQ ID NO: 1 and a heavy chain variable region (HCVR) comprising the amino acid sequence of SEQ ID NO: 2.

21. The method of claim 12, wherein the anti-TNFα antibody, or antigen binding portion thereof, is adalimumab.

22. The method of claim 12, wherein anti-TNFα antibody, or antigen binding portion thereof, is administered with at least one additional therapeutic agent.

23. The method of claim 12, wherein the subject is selected from the group consisting of a subject having HS at Hurley Stage II or III, a subject having an AN count of greater than or equal to 3 at baseline, a subject who is female, a subject who is over 40 years old, a subject who is a smoker, or any combination thereof.

24. The method of claim 12, wherein the subject achieves an HiSCR at week 12 of the treatment.

25. The method of claim 12, wherein the subject achieves at least a 30% reduction in skin pain at week 12 of the treatment.

26. A method for treating a subject having moderate to severe hidradenitis suppurativa (HS), the method comprising:
    at week 0 subcutaneously administering a first loading dose of 160 mg of adalimumab to the subject, wherein the first loading dose of adalimumab is administered as four 40 mg doses in one day or two 40 mg doses per day over two consecutive days;
    at week 2 subcutaneously administering a second loading dose of 80 mg of adalimumab to the subject, wherein the second loading dose of adalimumab is administered as two 40 mg doses in one day; and
    starting at week 4 subcutaneously administering a maintenance dose of 40 mg of adalimumab to the subject weekly.

27. The method of claim 26, further comprising subcutaneously administering to the subject 40 mg of adalimumab biweekly following a weekly maintenance dosing regimen.

28. The method of claim 26, wherein the subject has HS lesions in at least two distinct anatomic areas prior to treatment.

29. The method of claim 26, wherein the subject had an inadequate response to, contraindication to, or was intolerant to oral antibiotics for treatment of their HS.

30. The method of claim 26, wherein the subject is selected from the group consisting of a subject having HS at Hurley Stage II or III, a subject having an AN count of greater than or equal to 3 at baseline, a subject who is female, a subject who is over 40 years old, a subject who is a smoker, or any combination thereof.

31. The method of claim 26, wherein the subject achieves an HiSCR at week 12 of the treatment.

32. The method of claim 26, wherein the subject achieves at least a 30% reduction in skin pain at week 12 of the treatment.

33. The method of claim 26, wherein when a group of patients having moderate to severe HS are treated according to the treatment method of claim 26, statistically significantly more patients in said group achieve at least 30% reduction in pain relative to baseline at week 12 of said treatment, as compared to a group of patients having moderate to severe HS but treated with placebo under the same dosing scheme as in claim 26.

34. The method of claim 26, wherein when a group of patients having moderate to severe HS are treated according to the treatment method of claim 26, statistically significantly more patients in said group achieve HiSCR at week 12 of said treatment, as compared to a group of patients having moderate to severe HS but treated with placebo under the same dosing scheme as in claim 26.

* * * * *

SEQUENCE LISTING

```
<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: mutated human antibody

<400> SEQUENCE: 1

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45
```

```
Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys
            100                 105
```

<210> SEQ ID NO 2
<211> LENGTH: 121
<212> TYPE: PRT
<213> ORGANISM: Artificial Sequence
<220> FEATURE:
<223> OTHER INFORMATION: mutated human antibody

<400> SEQUENCE: 2

```
Glu Val Gln Leu Val Glu Ser Gly Gly Gly Leu Val Gln Pro Gly Arg
 1               5                   10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120
```

<210> SEQ ID NO 3
<211> LENGTH: 9
<212> TYPE: PRT
<213> ORGANISM: Artificial Sequence
<220> FEATURE:
<223> OTHER INFORMATION: mutated human antibody
<220> FEATURE:
<221> NAME/KEY: VARIANT
<222> LOCATION: (9)
<223> OTHER INFORMATION: Xaa = Thr or Ala

<400> SEQUENCE: 3

```
Gln Arg Tyr Asn Arg Ala Pro Tyr Xaa
 1               5
```

<210> SEQ ID NO 4
<211> LENGTH: 12
<212> TYPE: PRT
<213> ORGANISM: Artificial Sequence
<220> FEATURE:
<223> OTHER INFORMATION: mutated human antibody
<220> FEATURE:
<221> NAME/KEY: VARIANT
<222> LOCATION: (12)
<223> OTHER INFORMATION: Xaa = Tyr or Asn

<400> SEQUENCE: 4

```
Val Ser Tyr Leu Ser Thr Ala Ser Ser Leu Asp Xaa
 1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: mutated human antibody

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: mutated human antibody

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: mutated human antibody

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: mutated human antibody

<400> SEQUENCE: 8

Asp Tyr Ala Met His
1               5

<210> SEQ ID NO 9
<211> LENGTH: 107
<212> TYPE: PRT
<213> ORGANISM: Artificial Sequence
<220> FEATURE:
<223> OTHER INFORMATION: mutated human antibody

<400> SEQUENCE: 9

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: mutated human antibody

<400> SEQUENCE: 10

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
    50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial Sequence
<220> FEATURE:
<223> OTHER INFORMATION: mutated human antibody

<400> SEQUENCE: 11

Gln Lys Tyr Asn Ser Ala Pro Tyr Ala
1               5

<210> SEQ ID NO 12
<211> LENGTH: 9
<212> TYPE: PRT
<213> ORGANISM: Artificial Sequence
<220> FEATURE:
<223> OTHER INFORMATION: mutated human antibody

<400> SEQUENCE: 12

Gln Lys Tyr Asn Arg Ala Pro Tyr Ala
1               5

<210> SEQ ID NO 13
<211> LENGTH: 9
<212> TYPE: PRT
<213> ORGANISM: Artificial Sequence
<220> FEATURE:
<223> OTHER INFORMATION: mutated human antibody

<400> SEQUENCE: 13

Gln Lys Tyr Gln Arg Ala Pro Tyr Thr
1               5

```
<210> SEQ ID NO 14
<211> LENGTH: 9
<212> TYPE: PRT
<213> ORGANISM: Artificial Sequence
<220> FEATURE:
<223> OTHER INFORMATION: mutated human antibody

<400> SEQUENCE: 14

Gln Lys Tyr Ser Ser Ala Pro Tyr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: mutated human antibody

<400> SEQUENCE: 15

Gln Lys Tyr Asn Ser Ala Pro Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: mutated human antibody

<400> SEQUENCE: 16

Gln Lys Tyr Asn Arg Ala Pro Tyr Thr
1               5

<210> SEQ ID NO 17
<211> LENGTH: 9
<212> TYPE: PRT
<213> ORGANISM: Artificial Sequence
<220> FEATURE:
<223> OTHER INFORMATION: mutated human antibody

<400> SEQUENCE: 17

Gln Lys Tyr Asn Ser Ala Pro Tyr Tyr
1               5

<210> SEQ ID NO 18
<211> LENGTH: 9
<212> TYPE: PRT
<213> ORGANISM: Artificial Sequence
<220> FEATURE:
<223> OTHER INFORMATION: mutated human antibody

<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial Sequence
<220> FEATURE:
<223> OTHER INFORMATION: mutated human antibody

<400> SEQUENCE: 19

Gln Lys Tyr Thr Ser Ala Pro Tyr Thr
1               5
```

```
<210> SEQ ID NO 20
<211> LENGTH: 9
<212> TYPE: PRT
<213> ORGANISM: Artificial Sequence
<220> FEATURE:
<223> OTHER INFORMATION: mutated human antibody

<400> SEQUENCE: 20

Gln Lys Tyr Asn Arg Ala Pro Tyr Asn
 1               5

<210> SEQ ID NO 21
<211> LENGTH: 9
<212> TYPE: PRT
<213> ORGANISM: Artificial Sequence
<220> FEATURE:
<223> OTHER INFORMATION: mutated human antibody

<400> SEQUENCE: 21

Gln Lys Tyr Asn Ser Ala Ala Tyr Ser
 1               5

<210> SEQ ID NO 22
<211> LENGTH: 9
<212> TYPE: PRT
<213> ORGANISM: Artificial Sequence
<220> FEATURE:
<223> OTHER INFORMATION: mutated human antibody

<400> SEQUENCE: 22

Gln Gln Tyr Asn Ser Ala Pro Asp Thr
 1               5

<210> SEQ ID NO 23
<211> LENGTH: 9
<212> TYPE: PRT
<213> ORGANISM: Artificial Sequence
<220> FEATURE:
<223> OTHER INFORMATION: mutated human antibody

<400> SEQUENCE: 23

Gln Lys Tyr Asn Ser Asp Pro Tyr Thr
 1               5

<210> SEQ ID NO 24
<211> LENGTH: 9
<212> TYPE: PRT
<213> ORGANISM: Artificial Sequence
<220> FEATURE:
<223> OTHER INFORMATION: mutated human antibody

<400> SEQUENCE: 24

Gln Lys Tyr Ile Ser Ala Pro Tyr Thr
 1               5

<210> SEQ ID NO 25
<211> LENGTH: 9
<212> TYPE: PRT
<213> ORGANISM: Artificial Sequence
<220> FEATURE:
<223> OTHER INFORMATION: mutated human antibody

<400> SEQUENCE: 25

Gln Lys Tyr Asn Arg Pro Pro Tyr Thr
 1               5
```

<210> SEQ ID NO 26
<211> LENGTH: 9
<212> TYPE: PRT
<213> ORGANISM: Artificial Sequence
<220> FEATURE:
<223> OTHER INFORMATION: mutated human antibody

<400> SEQUENCE: 26

Gln Arg Tyr Asn Arg Ala Pro Tyr Ala
1               5

<210> SEQ ID NO 27
<211> LENGTH: 12
<212> TYPE: PRT
<213> ORGANISM: Artificial Sequence
<220> FEATURE:
<223> OTHER INFORMATION: mutated human antibody

<400> SEQUENCE: 27

Ala Ser Tyr Leu Ser Thr Ser Ser Ser Leu Asp Asn
1               5                   10

<210> SEQ ID NO 28
<211> LENGTH: 12
<212> TYPE: PRT
<213> ORGANISM: Artificial Sequence
<220> FEATURE:
<223> OTHER INFORMATION: mutated human antibody

<400> SEQUENCE: 28

Ala Ser Tyr Leu Ser Thr Ser Ser Ser Leu Asp Lys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: mutated human antibody

<400> SEQUENCE: 29

Ala Ser Tyr Leu Ser Thr Ser Ser Ser Leu Asp Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: mutated human antibody

<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: mutated human antibody

<400> SEQUENCE: 31

Ala Ser Tyr Leu Ser Thr Ser Phe Ser Leu Asp Tyr
1               5                   10

<210> SEQ ID NO 32

<211> LENGTH: 12
<212> TYPE: PRT
<213> ORGANISM: Artificial Sequence
<220> FEATURE:
<223> OTHER INFORMATION: mutated human antibody

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: mutated human antibody

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: mutated human antibody

<400> SEQUENCE: 34

Ala Ser Tyr Leu Ser Thr Ala Ser Ser Leu Glu Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: mutated human antibody

<400> SEQUENCE: 35

Val Ser Tyr Leu Ser Thr Ala Ser Ser Leu Asp Asn
1               5                   10

<210> SEQ ID NO 36
<211> LENGTH: 321
<212> TYPE: DNA
<213> ORGANISM: Artificial Sequence
<220> FEATURE:
<223> OTHER INFORMATION: mutated human antibody

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                                321

<210> SEQ ID NO 37
<211> LENGTH: 363
<212> TYPE: DNA
<213> ORGANISM: Artificial Sequence
<220> FEATURE:
<223> OTHER INFORMATION: mutated human antibody

```
<400> SEQUENCE: 37
gaggtgcagc tggtggagtc tgggggaggc ttggtacagc ccggcaggtc cctgagactc        60
tcctgtgcgg cctctggatt cacctttgat gattatgcca tgcactgggt ccggcaagct       120
ccagggaagg gcctggaatg ggtctcagct atcacttgga atagtggtca catagactat       180
gcggactctg tggagggccg attcaccatc tccagagaca acgccaagaa ctccctgtat       240
ctgcaaatga acagtctgag agctgaggat acggccgtat attactgtgc gaaagtctcg       300
taccttagca ccgcgtcctc ccttgactat tggggccaag gtaccctggt caccgtctcg       360
agt                                                                     363
```